(12) United States Patent
Luttrull et al.

(10) Patent No.: US 10,596,389 B2
(45) Date of Patent: Mar. 24, 2020

(54) PROCESS AND SYSTEM FOR UTILIZING ENERGY TO TREAT BIOLOGICAL TISSUE

(71) Applicant: Ojai Retinal Technology, LLC, Ojai, CA (US)

(72) Inventors: Jeffrey K. Luttrull, Ojai, CA (US); David B. Chang, Tustin, CA (US); Benjamin W. L. Margolis, Oakland, CA (US)

(73) Assignee: Ojai Retinal Technology, LLC, Ojai, CA (US)

( * ) Notice: Subject to any disclaimer, the term of this patent is extended or adjusted under 35 U.S.C. 154(b) by 0 days.

(21) Appl. No.: 16/038,561

(22) Filed: Jul. 18, 2018

(65) Prior Publication Data

US 2018/0339170 A1  Nov. 29, 2018

Related U.S. Application Data

(63) Continuation-in-part of application No. 15/918,487, filed on Mar. 12, 2018, which is a
(Continued)

(51) Int. Cl.
*A61N 5/06* (2006.01)
*A61N 5/02* (2006.01)
(Continued)

(52) U.S. Cl.
CPC ........ *A61N 5/0625* (2013.01); *A61F 9/00821* (2013.01); *A61N 5/025* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 3,408,593 A | 10/1968 | Hurwitz, Jr. | |
| 4,048,011 A | 9/1977 | Kovin et al. | |

(Continued)

FOREIGN PATENT DOCUMENTS

| | | | |
|---|---|---|---|
| DE | 10 2010 022 760 A1 | 12/2011 | |
| WO | 1997/017011 A1 | 5/1997 | |

(Continued)

OTHER PUBLICATIONS

Luttrull, Jeffrey K and Charles J Spink. "Serial optical coherence tomography of subthreshold diode laser micropulse photocoagulation for diabetic macular edema." Ophthalmic surgery, lasers & imaging : (Year: 2006).*

(Continued)

*Primary Examiner* — Joseph A Stoklosa
*Assistant Examiner* — Adam J Avigan
(74) *Attorney, Agent, or Firm* — Kelly & Kelley, LLP

(57) ABSTRACT

A process for heat treating biological tissue includes generating treatment radiation having a predetermined wavelength and average power. The treatment radiation is applied to biological tissue, such as retinal tissue, such that at least one treatment spot is formed on the biological tissue and the biological tissue is heat stimulated sufficiently to create a therapeutic effect without destroying the tissue.

17 Claims, 29 Drawing Sheets

Related U.S. Application Data continuation-in-part of application No. 15/629,002, filed on Jun. 21, 2017, now Pat. No. 10,278,863, and a continuation-in-part of application No. 15/583,096, filed on May 1, 2017, and a continuation-in-part of application No. 15/460,821, filed on Mar. 16, 2017, now abandoned, and a continuation-in-part of application No. 15/232,320, filed on Aug. 9, 2016, now Pat. No. 9,962,291, and a continuation-in-part of application No. 15/214,726, filed on Jul. 20, 2016, now Pat. No. 10,531,908, and a continuation-in-part of application No. 15/178,842, filed on Jun. 10, 2016, now Pat. No. 9,626,445, and a continuation-in-part of application No. 14/922,885, filed on Oct. 26, 2015, now Pat. No. 9,427,602, and a continuation-in-part of application No. 14/921,890, filed on Oct. 23, 2015, now Pat. No. 9,381,116, and a continuation-in-part of application No. 14/607,959, filed on Jan. 28, 2015, now Pat. No. 9,168,174, and a continuation-in-part of application No. 13/798,523, filed on Mar. 13, 2013, now Pat. No. 10,219,947, and a continuation-in-part of application No. 13/481,124, filed on May 25, 2012, now Pat. No. 9,381,115, application No. 16/038,561, which is a continuation-in-part of application No. 15/813,645, filed on Nov. 15, 2017, now Pat. No. 10,357,398, and a continuation-in-part of application No. 15/629,002, filed on Jun. 21, 2017, now Pat. No. 10,278,863, and a continuation-in-part of application No. 15/460,821, filed on Mar. 16, 2017, now abandoned.

(51) Int. Cl.
  *A61F 9/008* (2006.01)
  *A61N 5/067* (2006.01)
  *A61N 7/00* (2006.01)

(52) U.S. Cl.
  CPC .............. *A61F 2009/00863* (2013.01); *A61F 2009/00897* (2013.01); *A61N 2005/063* (2013.01); *A61N 2005/067* (2013.01); *A61N 2005/0659* (2013.01); *A61N 2005/0662* (2013.01); *A61N 2007/0043* (2013.01)

(56) References Cited

U.S. PATENT DOCUMENTS

| | | |
|---|---|---|
| 4,176,325 A | 11/1979 | Kajimura et al. |
| 4,194,114 A | 3/1980 | Pankratov et al. |
| 4,410,365 A | 10/1983 | Glukhovsky et al. |
| 4,556,051 A | 12/1985 | Maurer |
| 4,695,733 A | 9/1987 | Pesavento |
| 4,730,335 A | 3/1988 | Clark et al. |
| 4,791,634 A | 12/1988 | Miyake |
| 4,825,880 A | 5/1989 | Stauffer et al. |
| 4,865,029 A | 9/1989 | Pankratov et al. |
| 4,879,722 A | 11/1989 | Dixon et al. |
| 4,930,504 A | 6/1990 | Diamantopoulos et al. |
| 4,933,944 A | 6/1990 | McGraw |
| 4,935,931 A | 6/1990 | McGraw |
| 4,961,079 A | 10/1990 | Owens et al. |
| 4,967,416 A | 10/1990 | Esterowitz et al. |
| 5,037,421 A | 8/1991 | Boutacoff et al. |
| 5,067,951 A | 11/1991 | Greve |
| 5,085,492 A | 2/1992 | Kelsoe et al. |
| 5,088,803 A | 2/1992 | Buzawa |
| 5,147,354 A | 9/1992 | Boutacoff et al. |
| 5,348,002 A | 9/1994 | Caro |
| 5,372,595 A | 12/1994 | Gaasterland et al. |
| 5,394,199 A | 2/1995 | Flower |
| 5,430,756 A | 7/1995 | Hanihara |
| 5,520,680 A | 5/1996 | Shapshay et al. |
| 5,651,019 A | 7/1997 | Goldberg et al. |
| 5,982,789 A | 11/1999 | Marshall et al. |
| 6,047,216 A | 4/2000 | Carl et al. |
| 6,050,990 A | 4/2000 | Tankovich et al. |
| 6,066,128 A | 5/2000 | Bahmanyar et al. |
| 6,129,722 A | 10/2000 | Ruiz |
| 6,156,028 A | 12/2000 | Prescott |
| 6,208,769 B1 | 3/2001 | Pankratov |
| 6,222,869 B1 | 4/2001 | Marshall et al. |
| 6,259,952 B1 | 7/2001 | Sluijter et al. |
| 6,327,291 B1 | 12/2001 | Marshall |
| 6,377,599 B1 | 4/2002 | Marshall |
| 6,540,391 B2 | 4/2003 | Lanzetta et al. |
| 6,599,246 B1 | 7/2003 | Coffey et al. |
| 6,681,185 B1 | 1/2004 | Young et al. |
| 6,715,877 B2 | 4/2004 | Molebny |
| 6,733,490 B1 | 5/2004 | Falsini et al. |
| 6,813,942 B1 | 11/2004 | Vozhdaev et al. |
| 6,889,695 B2 | 5/2005 | Pankratov et al. |
| 6,942,655 B2 | 9/2005 | Peyman |
| 7,227,196 B2 | 6/2007 | Burgener, II et al. |
| 7,229,435 B2 | 6/2007 | Nakamura |
| 7,387,785 B1 | 6/2008 | Rudin et al. |
| 7,452,081 B2 | 11/2008 | Wiltberger et al. |
| 7,645,276 B2 | 1/2010 | Pankratov et al. |
| 7,763,828 B2 | 7/2010 | Talwar et al. |
| 7,766,903 B2 | 8/2010 | Blumenkranz et al. |
| 7,766,904 B2 | 8/2010 | McGowan, Sr. et al. |
| 7,771,417 B2 | 8/2010 | Telfair et al. |
| 7,909,816 B2 | 3/2011 | Buzawa |
| 8,007,702 B2 | 8/2011 | Gellman |
| 8,454,161 B2 | 6/2013 | Su et al. |
| 9,333,371 B2 | 5/2016 | Bean et al. |
| 2002/0099363 A1 | 7/2002 | Woodward et al. |
| 2002/0120255 A1 | 8/2002 | Sotiropoulos et al. |
| 2002/0165525 A1 | 11/2002 | Nakamura |
| 2003/0078567 A1 | 4/2003 | Dorin et al. |
| 2004/0098070 A1 | 5/2004 | Mohr et al. |
| 2005/0049582 A1 | 3/2005 | DeBenedictis et al. |
| 2005/0069531 A1 | 3/2005 | Karageozian et al. |
| 2005/0176662 A1 | 8/2005 | Inana et al. |
| 2006/0173512 A1 | 8/2006 | Barolet et al. |
| 2007/0173793 A1 | 7/2007 | Rathjen |
| 2007/0213693 A1 | 9/2007 | Plunkett |
| 2008/0015553 A1 | 1/2008 | Zacharias |
| 2008/0076958 A1 | 3/2008 | Britva et al. |
| 2009/0048586 A1 | 2/2009 | Krueger et al. |
| 2009/0093798 A1 | 4/2009 | Charles |
| 2009/0198309 A1 | 8/2009 | Gowda et al. |
| 2009/0276019 A1 | 11/2009 | Perez et al. |
| 2010/0049180 A1 | 2/2010 | Wells et al. |
| 2010/0068141 A1 | 3/2010 | Kaushal et al. |
| 2010/0082024 A1 | 4/2010 | Brannan et al. |
| 2010/0092424 A1 | 4/2010 | Sanghvi et al. |
| 2010/0100162 A1 | 4/2010 | Peyman |
| 2010/0152716 A1 | 6/2010 | Previn et al. |
| 2010/0168724 A1 | 7/2010 | Sramek et al. |
| 2010/0204093 A1* | 8/2010 | Kaushal .............. A61K 31/395 514/6.9 |
| 2010/0249760 A1 | 9/2010 | Blumenkranz et al. |
| 2010/0290007 A1 | 11/2010 | Van de Velde |
| 2011/0196350 A1 | 8/2011 | Friedman et al. |
| 2012/0226268 A1* | 9/2012 | Liu ...................... A61B 18/203 606/9 |
| 2013/0085481 A1 | 4/2013 | Dick et al. |
| 2013/0110095 A1 | 5/2013 | Boxer Wachler |
| 2013/0110206 A1 | 5/2013 | Yee et al. |
| 2013/0116672 A1* | 5/2013 | Yee ..................... A61F 9/00821 606/4 |
| 2013/0231721 A1 | 9/2013 | DeCharms |
| 2013/0317487 A1 | 11/2013 | Luttrull et al. |
| 2013/0317570 A1* | 11/2013 | Luttrull .............. A61F 9/00821 607/89 |
| 2014/0121631 A1 | 5/2014 | Bean et al. |
| 2014/0148735 A1 | 5/2014 | Nau, Jr. |
| 2014/0194958 A1 | 7/2014 | Chabal et al. |
| 2014/0228824 A1 | 8/2014 | Yee et al. |
| 2014/0364927 A1 | 12/2014 | Fuller |

(56) References Cited

U.S. PATENT DOCUMENTS

| | | |
|---|---|---|
| 2015/0058204 A1 | 2/2015 | Dunleavy et al. |
| 2015/0157498 A1 | 6/2015 | Luttrull et al. |
| 2015/0217125 A1 | 8/2015 | Chornenky et al. |
| 2016/0082294 A1 | 3/2016 | Luttrull et al. |
| 2016/0220834 A1 | 8/2016 | Schwarz |
| 2016/0296374 A1 | 10/2016 | Luttrull et al. |
| 2016/0338757 A1 | 11/2016 | Luttrull et al. |
| 2016/0346126 A1 | 12/2016 | Luttrull et al. |
| 2016/0361572 A1 | 12/2016 | Slayton |
| 2017/0232269 A1 | 8/2017 | Luttrull et al. |
| 2017/0319383 A1 | 11/2017 | Luttrull et al. |

FOREIGN PATENT DOCUMENTS

| | | |
|---|---|---|
| WO | 2004/043234 A2 | 5/2004 |
| WO | 2006002949 A2 | 1/2006 |
| WO | 2006005038 A2 | 1/2006 |
| WO | 2007035855 A2 | 3/2007 |
| WO | 2007106521 A2 | 9/2007 |
| WO | 2011/050056 A2 | 4/2011 |
| WO | 2012/018385 A2 | 2/2012 |

OTHER PUBLICATIONS

International Search Report for the International Application No. PCT/US2018/042833 dated Sep. 21, 2018.

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Luttrull, J K et al.; Subthreshold diode micropulse photocoagulation for the treatment of clinically significant diabetic macular oedema; Eye (2009) Macmillan Publishers Limited 2009.

Luttrull et al. Subthreshold diode micropulse panretinal photocoagulation for proliferative diabetic retinopathy. Eye (2007), 1-6 © 2007 Nature Publishing Group, www.nature.com/eye.

Small Beam Diameter Scanning Galvo Mirror Systems; Thorlabs; 1999-2013, 4 pgs.

Keller, Matthew D. et al.; Raman Spectroscopy for Cancer Diagnosis; www.spectroscopyonline.com; Nov. 2006 21(11); pp. 33-41 (including Reference (21) thereof).

International Search Report for PCT/US2015/0060836 dated Jan. 29, 2016.

Allingham RR, Damji KF, Freedman S, et al. Shields Textbook of Glaucoma, 6th Ed., 2010, Wolters Kluwer / Lippincott Williams & Wilkins, Philadelphia. ISBN-13: 978-0-7817-9585-2.

Danesh-Meyer HV, Levin LA. Glaucoma as a neurodegenerative disease. J Neuroophthalmol. Sep. 2015; 35 Suppl 1: S22-8.

Tian K, Shibata-Germanos S, Pahlitzsch M, Cordeiro MF. Current perspective of neuroprotection and glaucoma. Clin Ophthalmol. Nov. 11, 2015; 9: 2109-18.

Vujosevic S, Bottega E, Casciano M, et al. Microperimetry and fundus autofluorescence in diabetic macular edema. Subthreshold micropulse diode laser versus modified Early Treatment Diabetic Retinopathy Study Laser photocoagulation. Retina 2010; 30:908-16.

Lavinsky D, Cardillo JA, Melo, et al. Randomized clinical trial evaluating mETDRS versus normal or high-density micropulsephotocoagulation for diabetic macular edema. Invest Ophthalmol Vis Sci. Jun. 17, 2011; 52 (7): 4314-23.

Luttrull JK, Spink CJ, Musch DA. Subthreshold diode micropulse panretinal photocoagulation for proliferative diabetic retinopathy. Eye, May 2008; 22 (5): 607-12.

Luttrull JK, Sramek C, Palanker D, Spink CJ, Musch DC. Long-term safety, high-resolution imaging, and tissue temperature modeling of subvisible diode micropulse photocoagulation for retinovascular macular edema. Retina 2012; 32 (2): 375-86.

Malik KJ1, Sampat KM, Mansouri A, Steiner JN, Glaser BM. Low-intensity/high-density subthreshold microPulse diode laser for chronic central serous chorioretinopathy. Retina Mar. 2015;35(3):532-6.

Luttrull, JK. Low-Intensity/High-Density Subthreshold diode micropulse laser (SDM) for central serous chorioretinopathy. Retina, Jan. 2016 (in press).

Luttrull JK, Dorin G. Subthreshold diode micropulse photocoagulation as invisible retinal phototherapy for diabetic macular edema. A review. Current Diabetes Reviews, 2012, 8, 274-284.

Luttrull JK, Chang DB, Margolis BWL, Dorin G, Luttrull DK. Laser re-sensitization of medically unresponsive neovascular age-related macular degeneration: Efficacy and implications. Retina Jun. 2015; 35(6): 1184-1194.

Luttrull JK, Margolis BWL. Functionally guided retinal protective therapy as prophylaxis for age-related and inherited retinal degenerations. A pilot study. Invest Ophthalmol Vis Sci. Jan. 1, 2016;57(1):265-75. doi: 10.1167/iovs.15-18163.

McCulloch DL, Marmor MF, Brigell MG, et al. ISCEV Standard for full-field clinical electroretinography (2015 update). Doc Ophthalmol. Feb. 2015; 130 (1): 1-12.

Porciatti V, Ventura LM. Normative Data for a User-friendly Paradigm for Pattern Electroretinogram Recording. Ophthalmology, 2004; 111(1): 161-168.

Gutstein W, Sinclair SH, Presti P, North RV. Interactive thresholding of central acuity under contrast and luminance conditions mimicking real world environments: 1. Evaluation against LogMAR charts. J Comput Sci Sys Bio, 20125; 8(4) 225-232.

Parisi V, Centofanti M, Ziccardi L, et al. Treatment with citicoline drops enhances retinal function and neural conduction along the visual pathways in open angle glaucoma. Graefes Arch Clin Exp Ophthamol, May 2015; DOI 10.1007/s00417-015-3044-9.

Miller NR, ed. Walsh and Hoyt's Clinical Neurophthalmology. 4th Ed, 1985; Chapter 3: 41-60.Williams and Wilkins, Baltimore Maryland.

Salomão SR, Berezovsky A, Andrade RE, et al. Visual electrophysiologic findings in patients from an extensive Brazilian family with Leber'shereditary optic neuropathy. Doc Ophthalmol. Mar. 2004;108(2):147-55.

Kolomeyer AM, Zarbin MA. Trophic factors in the pathogenesis and therapy for retinal degenerative diseases. Surv Ophthalmol. Mar.-Apr. 2014;59 (2)134-65.

Kenealey J, Subramanian P, Comitato A, et al. Small Retinoprotective Peptides Reveal a Receptor-binding Region on Pigment Epithelium-derived Factor. J Biol Chem. Oct. 16, 2015;290(42):25241-53.

Yu PK1, Cringle SJ, McAllister IL, Yu DY. Low power laser treatment of the retina ameliorates neovascularisation in a transgenic mouse model of retinalneovascularisation. Exp Eye Res. Nov. 2009;89(5):791-800.

Flaxel C1, Bradle J, Acott T, Samples JR. Retinal pigment epithelium produces matrix metalloproteinases after laser treatment. Retina. Jun. 2007;27 (5):629-34.

Sramek C, Mackanos M, Spitler R, et al. Non-damaging retinal phototherapy: dynamic range of heat shock protein expression. Invest Ophthalmol Vis Sci. Mar. 28, 2011; 52 (3):1780-7.

Ventura LM, Feuer WJ, Porciatti V. Progressive loss of retinal ganglion cell function is hindered with IOP-lowering treatment in early glaucoma. IOVS, Feb. 2012 53 (2): 659-663.

Ventura LM, Porciatti V. Restoration of retinal ganglion cell function in early glaucoma after intraocular pressure reduction. A pilot study. Ophthalmology 2005, 112 (1): 20-27.

Yap GH, Chen LY, Png R, et al. Clinical value of electrophysiology in determining the diagnosis of visual dysfunction in neuro-ophthalmology patients. Doc Ophthalmol. Dec. 2015;131(3):189-96.

(56) References Cited

OTHER PUBLICATIONS

Waisbourd M, Ahmed OM, Molineaux J, et al. Reversible structural and functional changes after intraocular pressure reduction in patients with glaucoma. Graefes Arch Clin Exp Ophthalmol. Mar. 19, 2016. [Epub ahead of print] PMID: 26995555.

Banitt MR, Ventura LM, Feuer WJ, Savatovsky E, et al. Progressive loss of retinal ganglion cell function precedes structural loss by several years in glaucoma suspects. IOVS, Mar. 2013; 54 (3): 2346-2352.

Karu T. Photobiology of low-power laser effects. Review. Health Phys. May 1989; 56 (5): 691-704.

Gao X, Xing D. Molecular mechanisms of cell proliferation induced by low power laser irradiation. J Biomed Sci. Jan. 12, 2009;16:4.

Dorin G, Luttrull JK, Samples JR. Chapter 21: Laser alteration of collector channel ostia. Pivotal paradigm shift from photocoagulation to photostimulation. Glaucoma Research and Clinical Advances: 2016 to 2018. Knepper and Samples, Eds. Kugler Pub. Jan. 1, 2016, Amsterdam, Netherlands. ISBN: 9789062992478.

Van Teijlingen ER1, Rennie AM, Hundley V, Graham W. The importance of conducting and reporting pilot studies: the example of the Scottish Births Survey. J Adv Nurs. May 2001; 34 (3): 289-95.

Luttrull JK, Sinclair SH. Safety of transfoveal subthreshold diode micropulse laser (SDM) for fovea-involving diabetic macular edema in eyes with good visual acuity. Retina. Oct. 2014; 34 (10): 2010-20.

Luttrull, JK and Margolis BWL. improved retinal function following SDM laser for chronic disease. American Society of Retina Specialists Annual Meeting Vienna, Austria. Jul. 11, 2015 [online]. [retrieved on Jan. 11, 2017] <URL: http://www.diopsys.com/wp-content/uploads/2015/07/Luttrutl_Improved-retinal-function-following-SDM-laser-for-chronic-disease_ASRS2015.pdf>.

International Search Report for the International application No. PCT/US2016/46043 dated Dec. 27, 2016.

International Search Report for International Application No. PCT/US2016/62421 dated Feb. 7, 2017.

International Search Report for the International Application No. PCT/US2017/44337 dated Jan. 9, 2018.

International Search Report for the International Application No. PCT/US2015/60893, dated Mar. 18, 2016.

Westerheide, Sandy D. et al.; Heat Shock Response Modulators as Therapeutic Tools for Diseases of Protein Conformation; Minireview; Journal of Biological Chemistry; vol. 280, No. 39, pp. 33097-33100, Sep. 30, 2005.

Najarzadegan, Mohammad Reza et al.; The Role of Heat Shock Proteins in Alzheimer Disease: A Systematic Review; Avens Publishing Group; J Syndromes; vol. 3, Issue 1; 6 pgs.; May 2016.

International Search Report for the International Application No. PCT/US2017/064708, dated Feb. 9, 2018.

International Search Report for the International Application No. PCT/US2017/044319, dated Jan. 11, 2018.

International Search Report for the International Application No. PCT/US2018/22201, dated Jun. 1, 2018.

* cited by examiner

PROCESS AND SYSTEM FOR UTILIZING ENERGY TO TREAT BIOLOGICAL TISSUE

RELATED APPLICATIONS

This application is a continuation-in-part of U.S. application Ser. No. 15/918,487 filed Mar. 12, 2018, which is a continuation-in-part of U.S. application Ser. No. 15/629,002 filed Jun. 21, 2017, Ser. No. 15/583,096 filed May 1, 2017, Ser. No. 15/460,821 filed Mar. 16, 2017, Ser. No. 15/232,320 filed Aug. 9, 2016 (now U.S. Pat. No. 9,962,291), Ser. No. 15/214,726 filed Jul. 20, 2016, Ser. No. 15/178,842 filed Jun. 10, 2016 (now U.S. Pat. No. 9,626,445), Ser. No. 14/922,885 filed Oct. 26, 2015 (now U.S. Pat. No. 9,427,602), Ser. No. 14/921,890 filed Oct. 23, 2015 (now U.S. Pat. No. 9,381,116), Ser. No. 14/607,959 filed Jan. 28, 2015 (now U.S. Pat. No. 9,168,174), Ser. No. 13/798,523 filed Mar. 13, 2013, and Ser. No. 13/481,124 filed May 25, 2012. This application is also a continuation-in-part of U.S. application Ser. No. 15/460,821, filed Mar. 16, 2017 and Ser. No. 15/629,002, filed Jun. 21, 2017 and Ser. No. 15/813,645, filed Nov. 15, 2017.

BACKGROUND OF THE INVENTION

The present invention is generally directed to systems and processes for treating biological tissue, and particularly retinal tissue. More particularly, the present invention is directed to a process for heat treating retinal or other biological tissue using radiation, such as light beams, which create a therapeutic effect to a target tissue without destroying or permanently damaging the target tissue.

Retinal photocoagulation is a commonly used procedure for treating retinal diseases, including diabetic retinopathy. Retinal photocoagulation involves the use of light to create thermal burns in the retinal tissue. These thermal burns are believed to seal the retina and stop blood vessels from growing and leaking. Typically, the retinal laser burns are full-thickness in the areas of retinal pathology and visible at the time of treatment as white or gray retinal lesions. With time, these lesions develop into focal areas of chorioretinal scarring and progressive atrophy.

There are different exposure thresholds for retinal lesions that are haemorrhagic, ophthalmoscopically apparent, or angiographically demonstrable. A "threshold" lesion is one that is barely visible ophthalmoscopically at treatment time. A "subthreshold" lesion is one that is not visible at treatment time, but is detectable ophthalmoscopically or angiographically. "Suprathreshold" laser therapy is retinal photocoagulation performed to readily visible end point. In all cases, however, it is believed that actual tissue damage and scarring are necessary in order to create the benefits of the procedure. Photocoagulation has been found to be an effective means of producing retinal scars and has become the technical standard for macular photocoagulation for diabetic macular edema and other retinal diseases for many years.

Although providing a clear advantage compared to no treatment, current retinal photocoagulation treatments, which create retinal burns and scarring, have disadvantages and drawbacks. Conventional photocoagulation is often painful. This may require local anesthesia, which has its own attendant risks, or alternatively, treatment may be divided into stages over an extended period of time to minimize treatment pain and post-operative inflammation. Moreover, transient reduction in visual acuity is common following conventional photocoagulation.

In fact, thermal tissue damage may be the sole source of many potential complications of conventional photocoagulation which may lead to immediate and late visual loss. Such complications include sub-retinal fibrosis, choroidal neovascularization, and progressive expansion of laser scars. Inflammation resulting from the tissue destruction may cause or exacerbate macular edema, induced precipitous contraction of fibrovascular proliferation with retinal detachment and vitreous hemorrhage, and cause uveitis, serous choroidal detachment, angle closure or hypotony. While some of these complications are rare, others, including treatment pain, progressive scar expansion, visual field loss, decreased night vision, etc. are so common so as to be accepted as inevitable side effects of conventional laser retinal photocoagulation. Due to the inherent retinal damage in conventional photocoagulation treatment, treatment of the fovea and other sensitive areas of the retina is strictly forbidden, notwithstanding the most visually disabling diabetic macular edema occurs in these areas.

Another problem is that the treatment requires the application of a large number of laser doses to the area of the retina to be treated. This can be tedious and time-consuming as it is not uncommon for hundreds or even in excess of one thousand laser spots to be necessary in order to provide a full treatment. The physician is responsible for ensuring that each laser beam spot is properly positioned away from sensitive areas of the eye, such as the fovea, that could result in permanent damage. Point-by-point treatment of a large number of locations, using a single laser beam sequentially, tends to be a lengthy procedure, which frequently results in physician fatigue and patient discomfort.

The inventors have discovered that radiation, such as in the form of various wavelengths of light, can be applied to retinal tissue in a manner that does not destroy or permanently damage the retinal tissue, but achieves the beneficial effects on the eye diseases. The inventors have found that one or more light beams can be generated and applied to the retinal tissue such that it is therapeutic, yet sublethal to the retinal tissue, and avoids damaging photocoagulation in the retinal tissue, yet provides preventative and protective treatment of the retinal tissue of the eye. It is believed that the process raises the tissue temperature such in a controlled manner to selectively stimulate heat shock protein activation and/or production and facilitation of protein repair, which serves as a mechanism for therapeutically treating the tissue. It is believed that these activated heat shock proteins may reset the diseased retina to its healthy condition by removing and repairing damaged proteins. This then results in improved RPE function, improves retinal function and autoregulation, restorative acute inflammation, reduced chronic inflammation, and systematic immunodulation. The effects of the present invention may slow, stop or even reverse retinal diseases and improve visual function and reduce the risk of visual loss. It is believed that raising tissue temperature in such a controlled manner to selectively stimulate heat shock protein activation without damaging or destroying the tissue has benefits in other tissues as well.

SUMMARY OF THE INVENTION

The present Invention resides in a process for heat treating biological tissue. In accordance with the Invention, treatment radiation is generated and applied to the biological tissue in such a manner so as to heat stimulate the biological tissue sufficiently to create a therapeutic effect without destroying the tissue.

More particularly, treatment radiation is generated having a wavelength between 570 nm and 1300 nm and an average power of between 0.0000069 to 37.5 watts. Treatment radiation may be generated which has a wavelength between 600 nm-1100 nm and an average power of between 0.00015 and 6.94 watts.

The treatment radiation is applied to the biological tissue such that at least one treatment spot having a diameter between 10-700 microns Is formed on the biological tissue. At least one treatment spot having a diameter of between 100-500 microns may also be formed. The treatment radiation may be pulsed and applied to the tissue for a duration of between 30-800 milliseconds.

The treatment radiation may be applied to retinal tissue of an eye. The treatment radiation may be applied to at least a portion of the fovea of the eye.

The tissue may be heated to between six and eleven degrees Celsius during the application of the treatment radiation to the tissue. However, the average temperature rise of the tissue over several minutes is maintained at approximately one degree Celsius or less. This may stimulate heat shock protein activation in a tissue, and thus create a therapeutic effect, without destroying the tissue.

A plurality of spaced apart beams of treatment radiation may be generated and simultaneously applied to the tissue to form a plurality of spaced apart treatment spots in a first treatment area. During an interval of time, comprising less than one second, between pulses of treatment radiation applied to the first treatment area of the tissue, the treatment radiation beams may be moved and applied to a second treatment area of the tissue sufficiently spaced apart from the first treatment area of the tissue to avoid thermal tissue damage of the target tissue. The treatment radiation beams may be repeatedly applied, in an alternating manner during the same treatment session, to each of the first and second treatment areas of the tissue until a predetermined number of applications to each of the first and second treatment areas of the tissue has been achieved.

The treatment radiation may be applied to the tissue for a first period of time, such as less than one second, to stimulate heat shock protein activation in the tissue. The application of the treatment radiation is halted for an interval of time that exceeds the first period of time, such as several seconds to several minutes. The treatment radiation is then reapplied to the tissue after the interval of time, within a single treatment session, so as to controllably raise the temperature of the tissue without destroying the tissue to increase the level of heat shock protein activation in the tissue.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
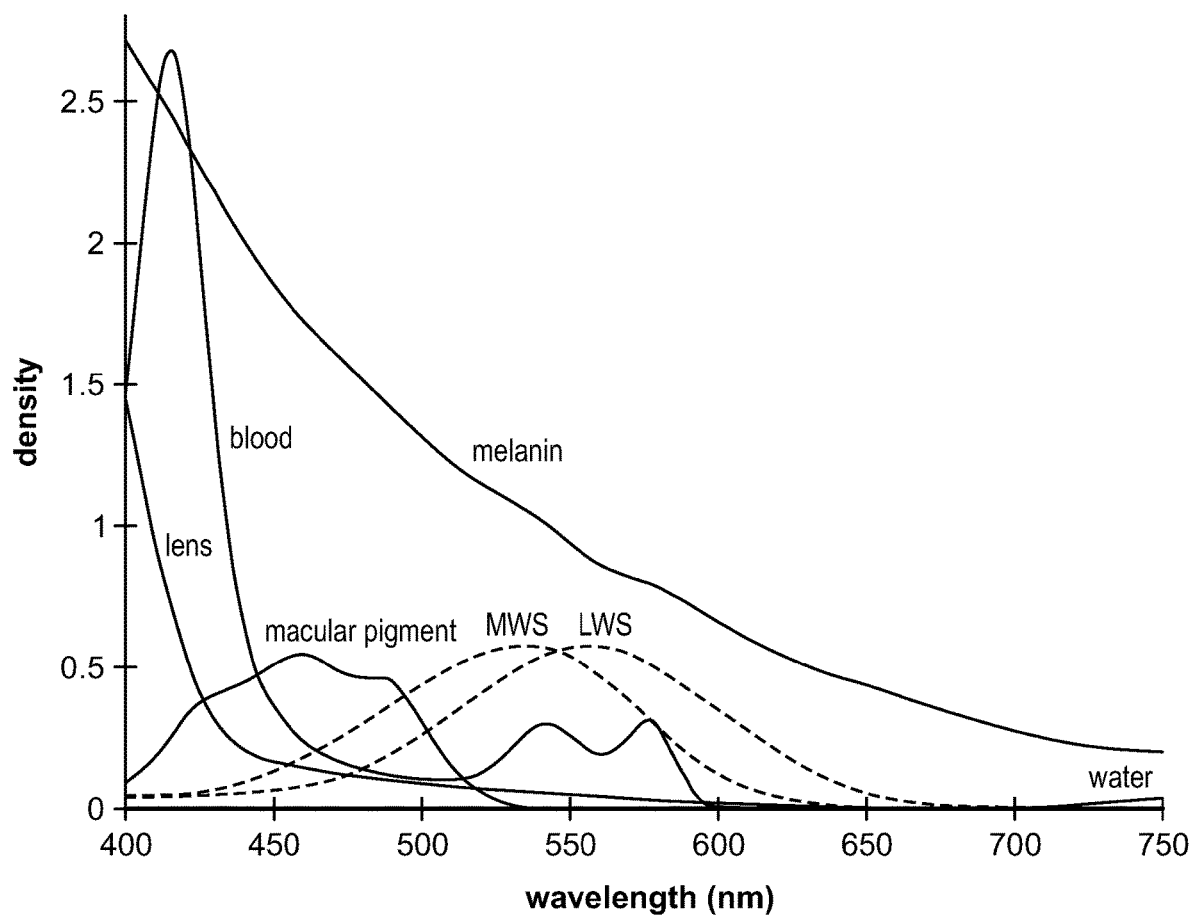
FIG. 1 is a graph illustrating absorption of radiation at given wavelengths by blood and ocular tissues.

As shown in the accompanying drawings, and as more fully described herein, the present invention is directed to a system and method for heat treating biological tissue. This may be done by delivering radiation, such as one or more light beams or the like, having energy and application parameters selected to cause a thermal time-course in tissue to raise the tissue temperature over a short period of time to a sufficient level to achieve a therapeutic effect while maintaining an average tissue temperature over a prolonged period of time below a predetermined level so as to avoid permanent tissue damage. It is believed that the creation of the thermal time-course stimulates heat shock protein activation or production and facilitates protein repair without causing any damage.

The inventors have discovered that electromagnetic radiation can be applied to retinal tissue in a manner that does not destroy or damage the retinal tissue while achieving beneficial effects on eye diseases. More particularly, a laser light beam can be generated that is therapeutic, yet sublethal to retinal tissue cells and thus avoids damaging photocoagulation in the retinal tissue which provides preventative and protective treatment of the retinal tissue of the eye. It is believed that this may be due, at least in part, to the stimulation and activation of heat shock proteins and the facilitation of protein repair in the retinal tissue.

Various parameters of the light beam must be taken into account and selected so that the combination of the selected parameters achieve the therapeutic effect while not permanently damaging the tissue. These parameters include radiation wavelength, radius of the radiation source or spot size formed on the retina, radiation power, application duration, and duty cycle of the pulse train. In particular, radiation wavelength, average radiation power, spot size formed on the retina by the radiation source, and application duration, such as the train duration of a pulsed radiation source are particularly important parameters when generating and applying the treatment radiation to the retina in order to achieve therapeutic effect without destroying or permanently damaging the tissue.

The selection of these parameters may be determined by requiring that the Arrhenius integral for HSP activation be greater than 1 or unity. At the same time, the selected parameters must not permanently damage the tissue. Thus, the Arrhenius integral for damage may also be used, wherein the solved Arrhenius integral is less than 1 or unity. Alternatively, the FDA/FCC constraints on energy deposition per unit gram of tissue and temperature rise as measured over periods of minutes be satisfied so as to avoid permanent tissue damage. The FDA/FCC requirements on energy deposition and temperature rise are widely used and can be referenced, for example, at www.fda.gov/medicaldevices/deviceregulationandguidance/guidancedocuments/ucm073817.htm#attacha for electromagnetic sources. Generally speaking, tissue temperature rises of between 6° C. and 11° C. can create therapeutic effect, such as by activating heat shock proteins, whereas maintaining the average tissue temperature over a prolonged period of time, such as over several minutes, such as six minutes, below a predetermined temperature, such as 1° C. or less, will not permanently damage the tissue.

As mentioned above, wavelength of the treatment radiation is one of the parameters which must be determined and selected. The possible wavelength range is determined at the increased absorption by the tissue, such as the retina's visual pigments, at the lower end and by the decreased melanin absorption coupled with the increased water absorption at the upper end. Although the process of the present invention can be used to treat a variety of tissues, it has been found to be particularly suitable for treating ocular disorders and diseases, and particularly retinal disorders. Thus, the parameters described herein are particularly suited for treatment of such retinal disorders.

With reference to FIG. 1, which illustrates the absorption of radiation along a spectrum of wavelengths by blood, RPE melanin, macular pigments, the lens, water, and long wavelength sensitive (LWS) and medium wavelength sensitive (MWS) visual pigments. FIG. 1 displays the optical density, or the product of the absorption-per-unit length times the absorption length as a function of wavelength between 400 nm and 750 nm wavelength of the radiation, such as within the light spectrum. FIG. 1 shows that above 650 nm, the absorption is practically all due to the melanin in the RPE. At approximately 570 nm, the sum of the optical densities of the LWS and the MWS pigments and the blood exceeds the optical density of the melanin. This is not desirable as the patient will experience visual effects during the treatment due to the absorption of the visual pigments below 450 nm, the absorption is primarily due to the RPE melanin, blood and the lens. However, absorption by the lens is not desirable as that causes heating of the lens that might result in denaturation of the proteins comprising the lens. Thus, the lower wavelength limit realistically usable by the process of the present invention is determined by undesirable absorption by the visual pigments and other absorbers. Consequently, a lower extreme wavelength limit would be approximately 570 nm where the melanin and sum of the visual pigment optical densities are comparable. A preferable lower wavelength limit, however, would be 600 nm, where the absorption is dominated by the melanin with no visual pigment absorption, and thus avoiding the patient experiencing visual disturbances during treatment.

Figure 2:
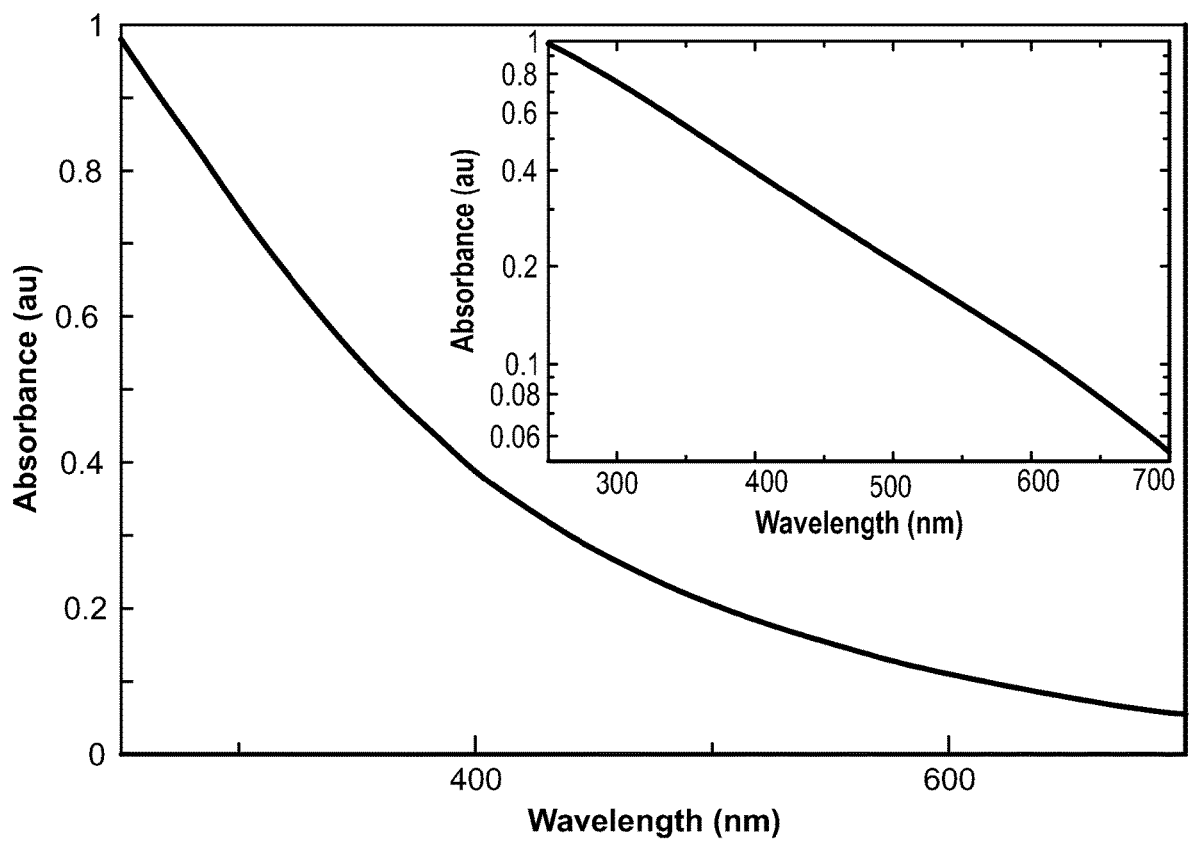
FIG. 2 is a graph depicting properties of melanin and absorbance of RPE melanin as a function of wavelength.

It is believed that the therapeutic effect of the radiation treatment is due to the activation of HSPs in the RPE due to the laser-induced elevation of RPE temperature. In the desired operating range of wavelengths, this temperature elevation is due primarily to the absorption of radiation by the thin layer (approximately 6 microns of melanin in the anterior portion of the RPE). FIG. 2 shows the absorbance of the RPE melanin as a function of wavelength between 250 nm and 700 nm in arbitrary units (AU). It has been found that the plot could be fit by an exponential: $\exp[-0.0062 \lambda(nm)]$. The absorption coefficient has been found to be 104 $cm^{-1}$ at $\lambda=810$ nm, so that $\alpha_{melanin}(\lambda)=104 \exp[-0.0062(\lambda(nm)-810)]$. Thus, the absorbance drops off quite rapidly as wavelength increases. At 1300 nm, for instance, the melanin absorbance is only 0.048 what it is at 810 nm. At 810 nm, the fraction of the incident radiation that is absorbed by the melanin is 6%. At 1300 nm, this drops to only 0.3%. This means that at 1300 nm, the radiation power due to this effect alone would have to be increased by a factor of 20 compared to the power at 810 nm to achieve the same temperature increase.

Figure 3:
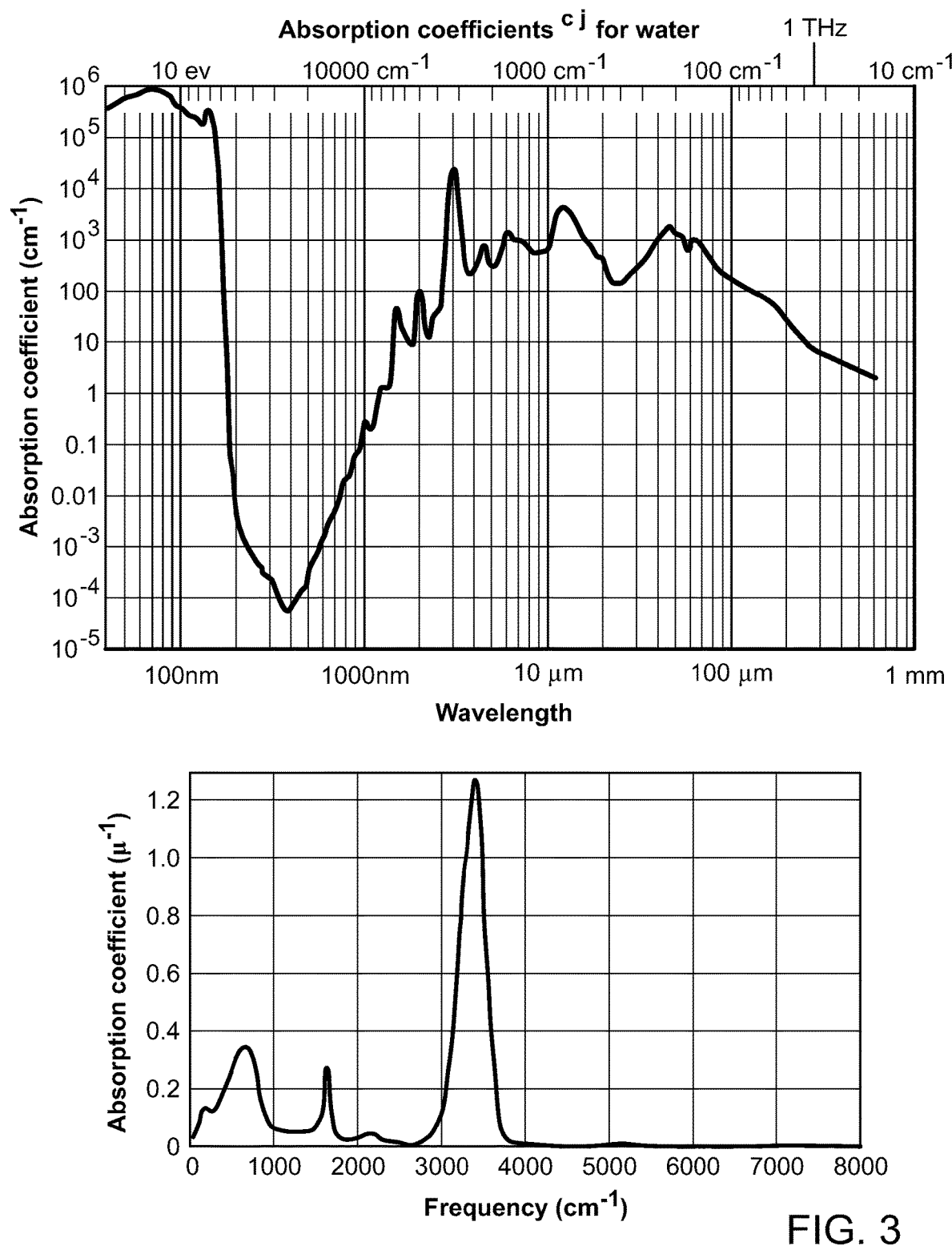
FIG. 3 is a graph depicting absorption coefficients of water at various wavelengths.

In addition to the decrease in melanin absorption with increasing wavelength, the absorption by water in the vitreous increases. The absorption coefficient of water is a function of wavelength (between 49 nm and 1 mm) is shown in FIG. 3. As can be seen in FIG. 3, the absorption coefficient of water to radiation increases from 0.03 cm$^{-1}$ at 810 nm to 0.3 cm$^{-1}$ at 1300 nm. This means that as the wavelength increases above 810 nm, the temperature of the eye lens and of the vitreous will increase more for a given input laser power. Between 400 nm and 1500 nm, it appears from FIG. 3 that $\alpha_{water}(\lambda)/\alpha(810) \approx (\lambda/810)^5$, i.e., $\alpha_{water}(\lambda) \approx 0.03 [\lambda((nm)/810]^5$.

Figure 4A:
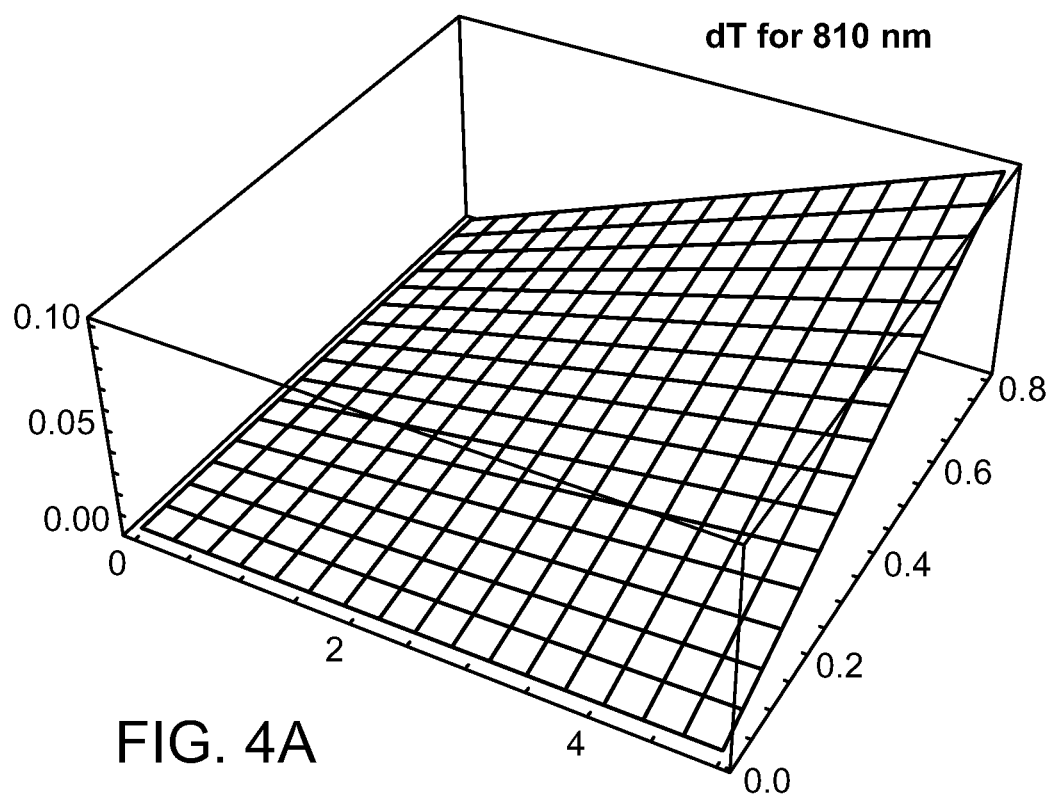
FIGS. 4A and 4B are graphs depicting radiation-induced temperature rise in the lens of an eye as a function of the average radiation power and time of irradiation.
Figure 4B:
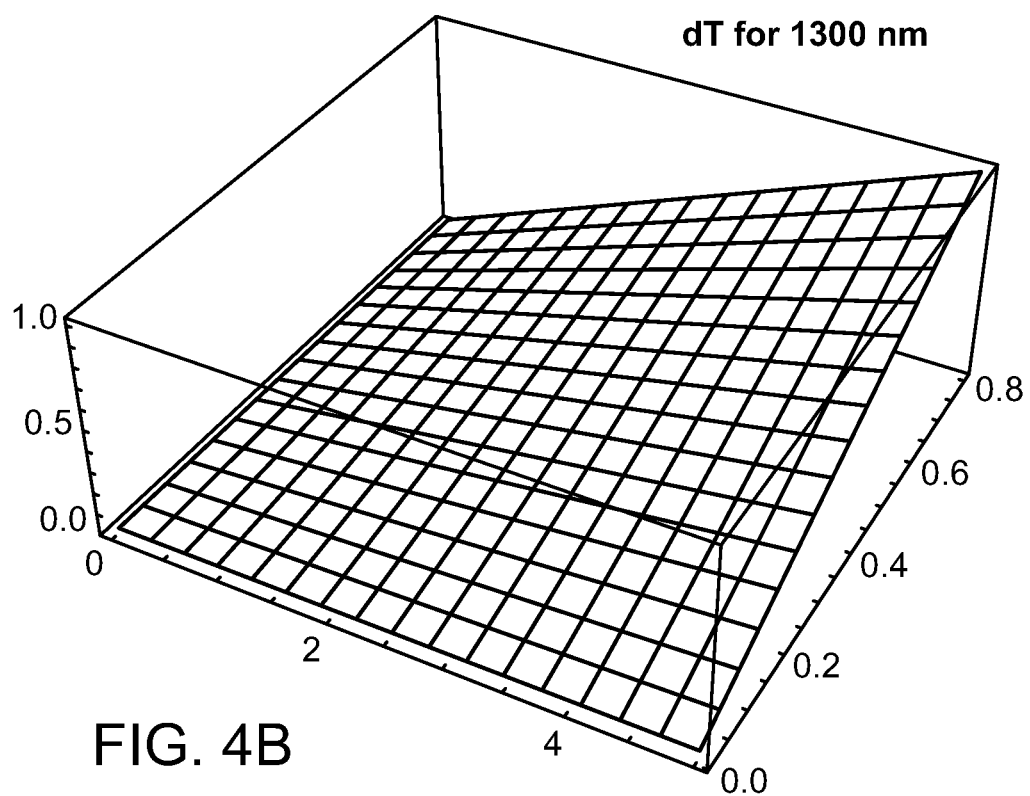

With reference now to FIGS. 4A and 4B, the radiation-induced temperature rise in the lens of the eye as a function of the average radiation power and time of irradiation for wavelengths of 810 nm and 1300 nm are shown. The plot is for powers in the range of 0 to 5 watts and for irradiation times in the range of 0 to 0.8 seconds. It can be seen from FIGS. 4A and 4B that increasing the wavelength from 810 nm to 1300 nm results in an order of magnitude increase in the temperature rise of the lens. At the same time, the resulting temperature rises in the lens for the powers and irradiation times would not result in denaturation of the lens proteins for either wavelength and thus while 810 nm would be a preferable wavelength, it is unlikely that an increase in the wavelength to the order of 1300 nm would cause damage to the lens.

The magnitude and effect of temperature increase at the longer wavelengths near the retina can be larger, however. The reason for this is that near the lens, the radius of the radiation is of the same order as that of the lens, approximately 3 mm. Near the retina, however, the radiation is focused to a much smaller radius. The difference in radii results in a much larger temperature rise near the retina, in spite of the fact that near the lens thermal diffusion distances during the irradiation time are much less than the radius, whereas near the retina the temperature rise is diminished by thermal diffusion. Due to the thermal diffusion near the lens, the water-absorption-induced temperature rise there is essentially independent of the spot size.

Figure 5:
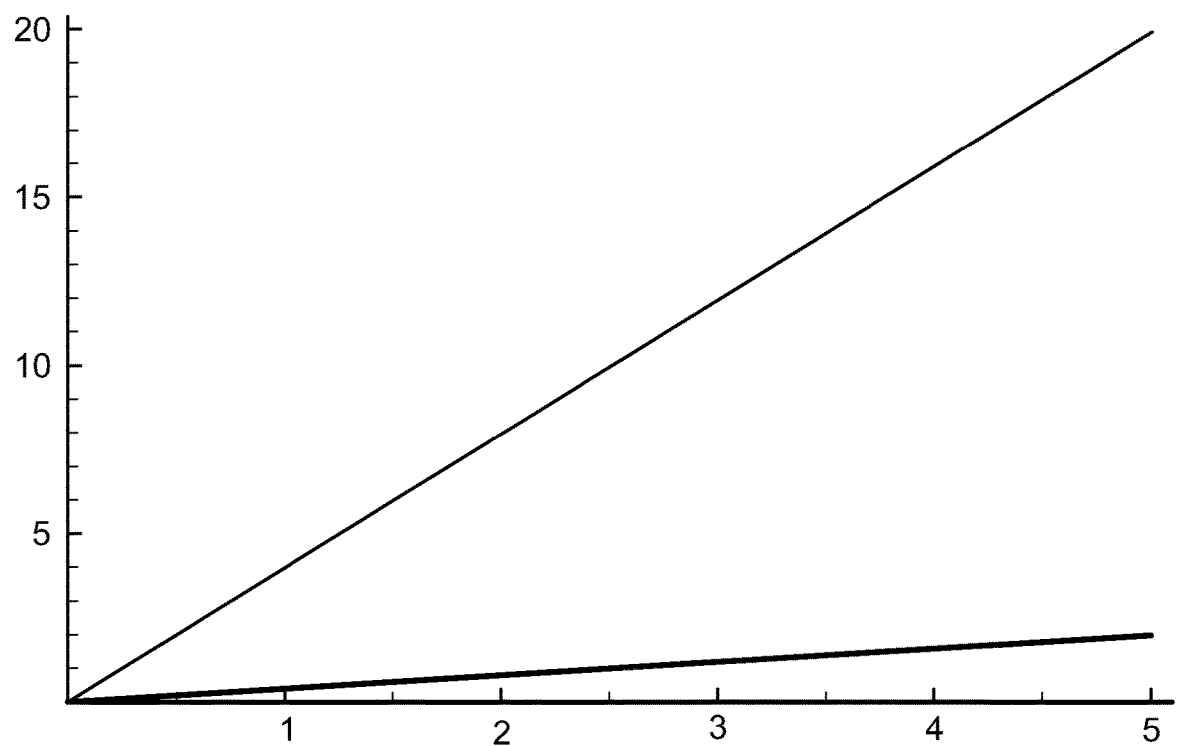
FIG. 5 is a graph depicting the increase in water temperature near the retina as a function of average radiation power for different wavelengths.

FIG. 5 illustrates increase in water temperature near the retina as a function of average radiation power, the top curve being at a wavelength of 1300 nm and the bottom curve for 810 nm radiation wavelengths. The power ranges from 0 to 5 watts. FIG. 5 shows that at the 810 nm wavelength, the temperature rise is small and should not damage the retina. At the 1300 nm wavelength, the temperature rise can be quite appreciable as the average power increases. As can be seen in FIG. 5, the temperature rise is 8 K for a power of 2 watts. Nevertheless, as will be shown more fully below, it is unlikely that the average power levels at this magnitude will be needed. Accordingly, it is unlikely that for average powers of interest in the invention that increasing the radiation wavelength to the order of 1300 nm should raise the water temperature near the retina to the point where damage is inflicted.

Another consideration is the amount of radiation power attenuation in the water before the RPE is reached. The power at the retina is obtained from the power incident on the eye by the factor $\exp[-\alpha L]$, where $\alpha$ is the absorption coefficient of water and L is the distance through the eye:

$\alpha(810 \text{ nm}) = 0.03 \text{ cm}^{-1}$
$\alpha(1300 \text{ nm}) = 0.3 \text{ cm}^{-1}$
$L = 2.5 \text{ cm}$ Thus, at 810 nm, $\exp[-0.03 \times 2.5] = 0.93$ of the incident radiation arrives at the retina, whereas at 1300 nm, only $\exp[-0.3 \times 2.5] = 0.47$ of the incident radiation arrives at the retina.

Accordingly, as the wavelength increases to the order of 1300 nm, the efficiency of the treatment decreases appreciably. To obtain the same temperature increase in the RPE, twice as powerful a radiation source would have to be employed as at 810 nm if the absorption coefficient of the RPE melanin were the same at the two wavelengths. However, the melanin absorption coefficient is smaller by a factor of 20. The two effects combined mean that the radiation power would have to be increased by about 40 times to achieve the same temperature rise.

From the foregoing, it is apparent that there are two main consequences of using longer wavelengths, namely, a decrease in the melanin absorption and an increase in the amount of attenuation in the vitreous due to the increased water absorption. To estimate the impact of the decrease in melanin absorption on the required radiation power, it is enough to recognize that the temperature increase that activates the HSPs is proportional to $P\alpha_{melanin}$, where P is the power incident on the retina. To estimate the impact of the increased attenuation in the vitreous, we simply note that the power incident on the retina is related to the power incident on the eye by $\exp[-\alpha_{water}L]$. So if we designate the required radiation power incident on the eye at 810 nm by p(810), the required power at any other wavelength can be approximately written as $p(\lambda) = p(810) \text{Exp}[0.0062(\lambda_{nm}-810)]\text{Exp}[0.075 \{\lambda_{nm}/810\}^5]$.

Figure 6:
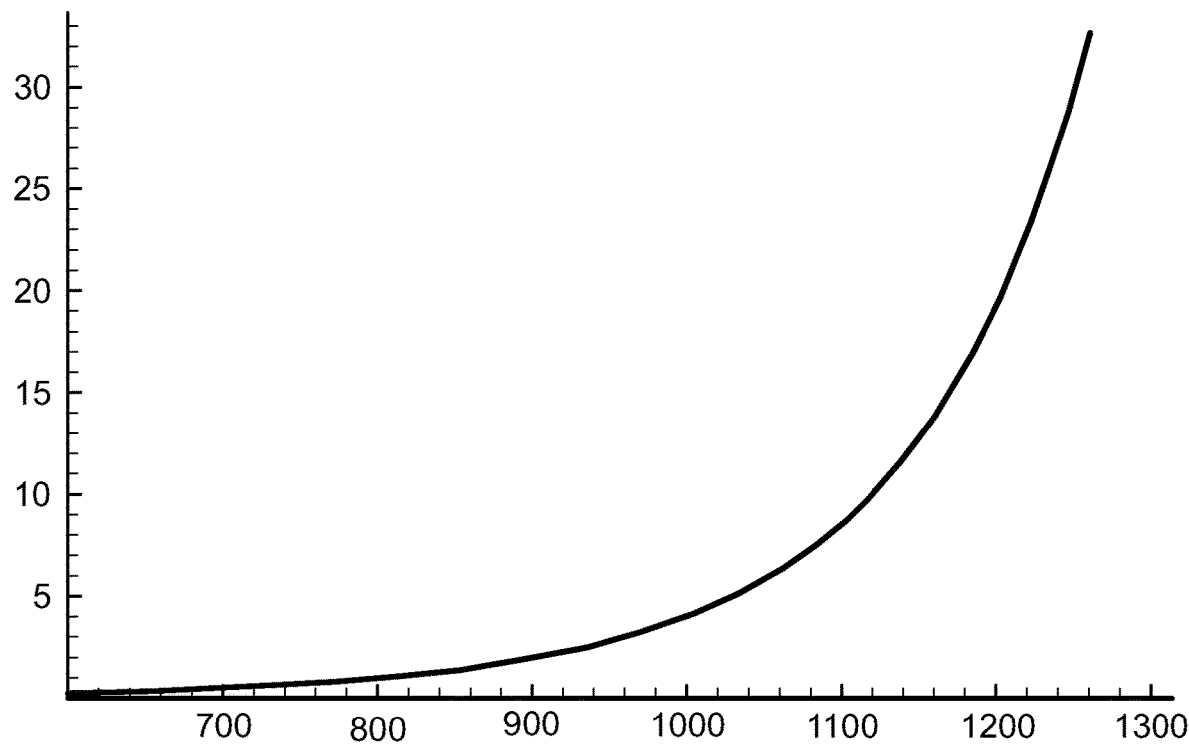
FIG. 6 is a graph depicting the increase in required power as the radiation wavelength increases for melanin absorption and heat shock protein activation.

The ratio $p(\lambda)/p(810)$ between 600 nm and 1300 nm wavelengths is plotted in FIG. 6. It can be seen from FIG. 6 that as the radiation wavelength increases, the required power for HSP activation increases greatly due to both the increased water absorption and decreased melanin absorption. It can be seen from the foregoing that due to the very large increase in required radiation power for HSP activation as the wavelength is increased, a reasonable upper limit on the usable wavelength for the process of the present invention is 1300 nm. However, a more preferable upper limit on wavelength is 1100 nm, where although the power required is still larger than its shorter wavelengths, it is not nearly as much as higher wavelengths.

From the foregoing, the present invention can be performed in a broad range of wavelengths between 570 nm to 1300 nm. However, a more preferable range of wavelengths is 600 nm to 1100 nm. An even more preferable range of wavelengths is 700 nm to 900 nm, with a particularly preferred operating wavelength at approximately 810 nm. At these wavelengths, the melanin absorption is dominant with the heating primarily in the desired RPE and the wavelength is at a safe distance from the wavelengths where appreciable absorption occurs in the visual pigments at shorter wavelengths or water at longer wavelengths.

In addition to wavelength, the other parameters that need to be specified in order for one to be able to practice the invention are the duration of the irradiation at a single spot, the single spot radius of the radiation at the retina, and the average power P at the retina.

Alternatively, the average radiation power P can be replaced by the average radiation power density $P_1$ at the retina, where the two quantities are related simply by $P_1 = P/(\pi R^2)$, where R designates the radius of the radiation spot on the retina.

For a repetitive micropulse system of the type used in the invention, the average radiation power density (fluence) $P_1$ at the retina is related to the peak radiation power density at the retina multiplied by the duty cycle dc of the micropulse train. The peak radiation power delivered to the retina is equal to the peak radiation "dial power" for a single spot times the efficiency of transmission q of the optical system. The efficiency is typically about 80%. If the laser illuminates a grid of N spots and has a total peak dial power of $P_{peak}$, then $P_1 = \eta(\text{dc } P_{peak}/N)/(\pi R^2)$.

Figure 7A:
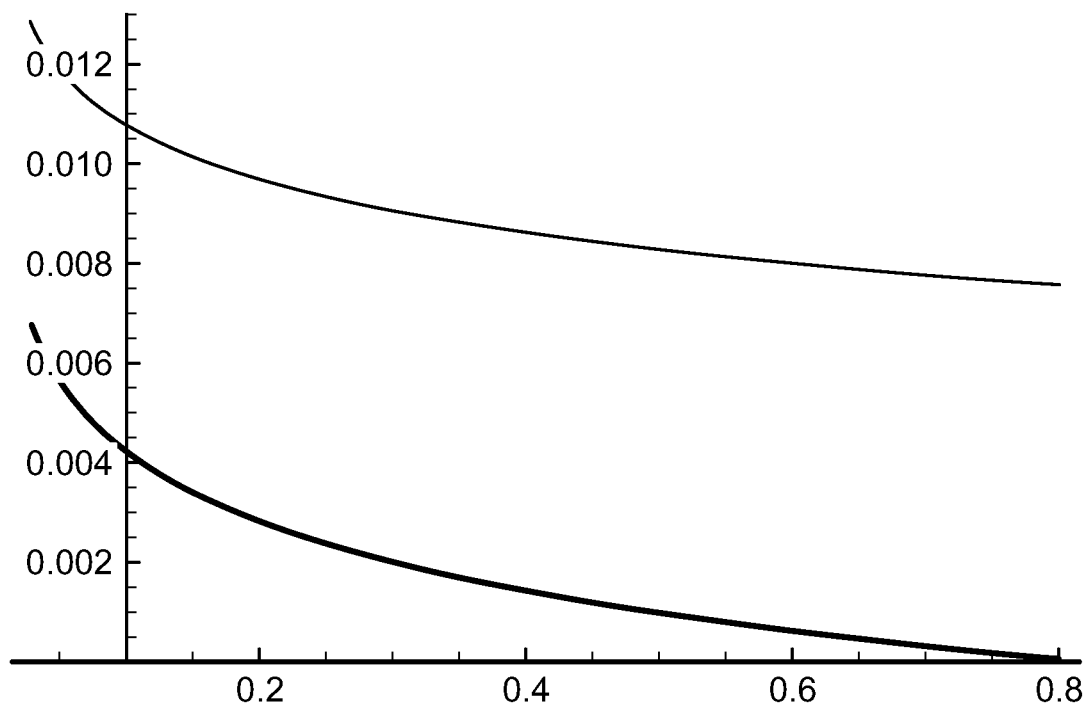
FIGS. 7A-7C are graphs depicting average power at retinal spots of varying diameters as a function of the radiation duration for average required treatment power and maximum allowable average treatment power, in accordance with the present invention.
Figure 7B:
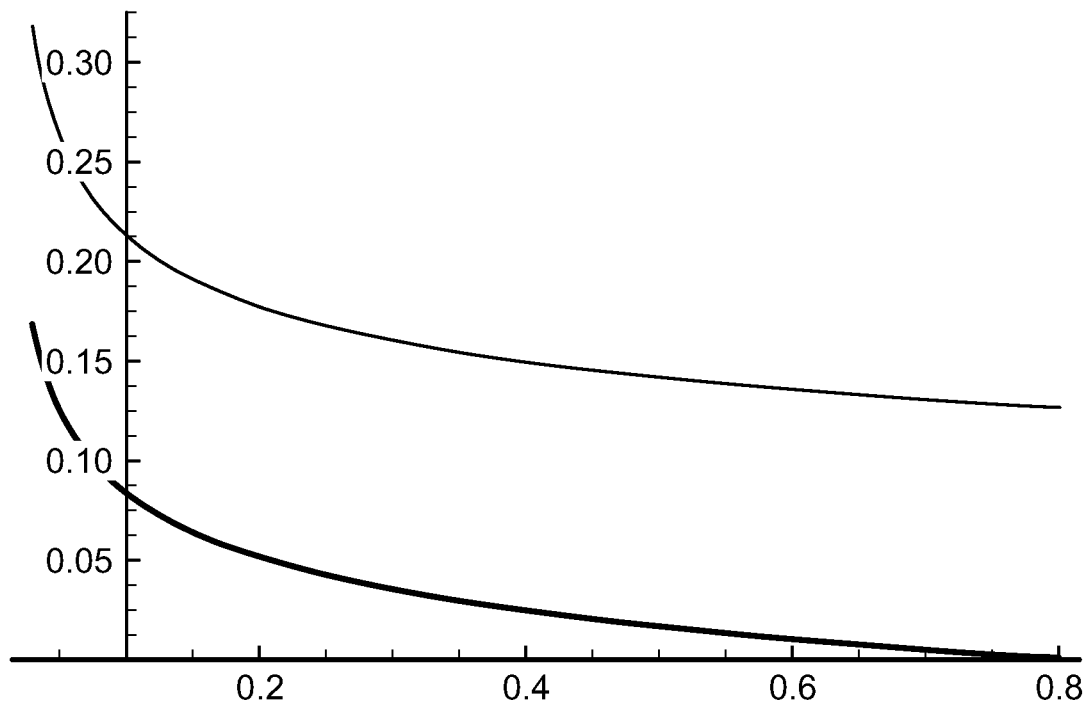
Figure 7C:
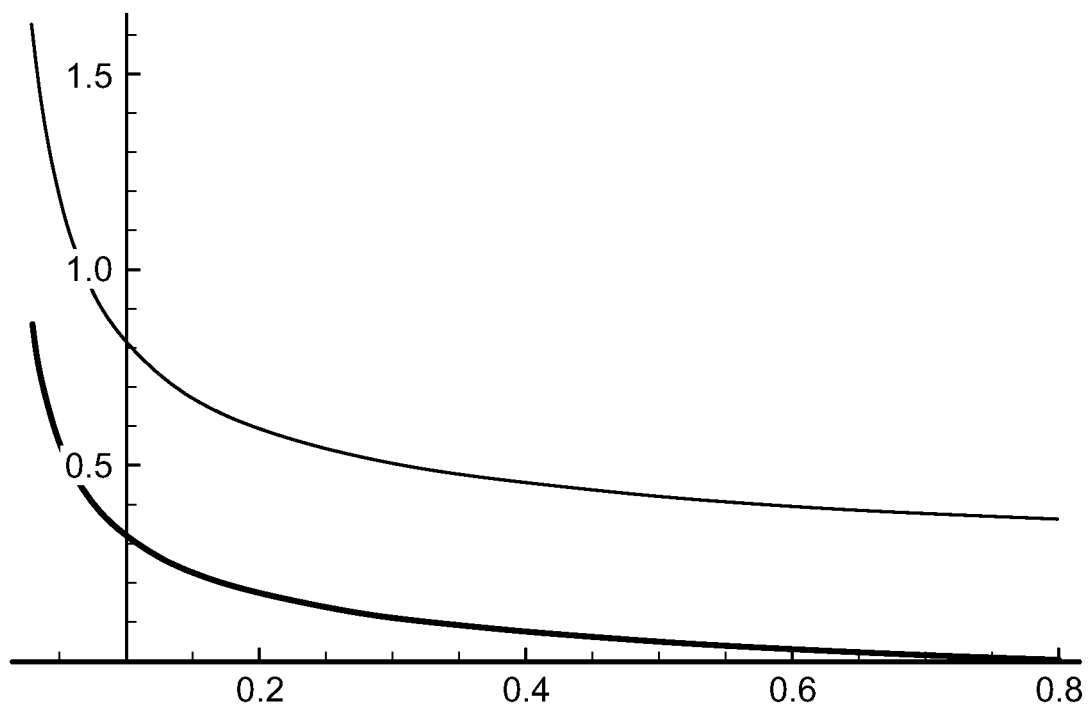

FIGS. 7A-7C show the dependence of the required average radiation power on spot size and radiation duration. For each figure, two powers are shown, namely, $P_{reset}$, the average required treatment power (bottom curve), and $P_{damage}$, the maximum allowable average treatment power above which appreciable damage can occur (top curve). The lower curve shows the power which gives a reset Arrhenius integral of 1. The top curve gives a damage threshold Arrhenius integral of 1. The radiation durations range from 0.03 seconds to 0.8 seconds. A radiation wavelength of 810 nm is assumed. FIG. 7A illustrates the average power in watts at a retinal spot of diameter 10 microns as a function of the radiation duration. FIG. 7B illustrates the average power in watts at a retinal spot diameter of 200 microns as a function of the radiation duration. FIG. 7C illustrates the average power in watts at a retinal spot diameter of 500 microns as a function of the radiation duration.

Figure 8A:
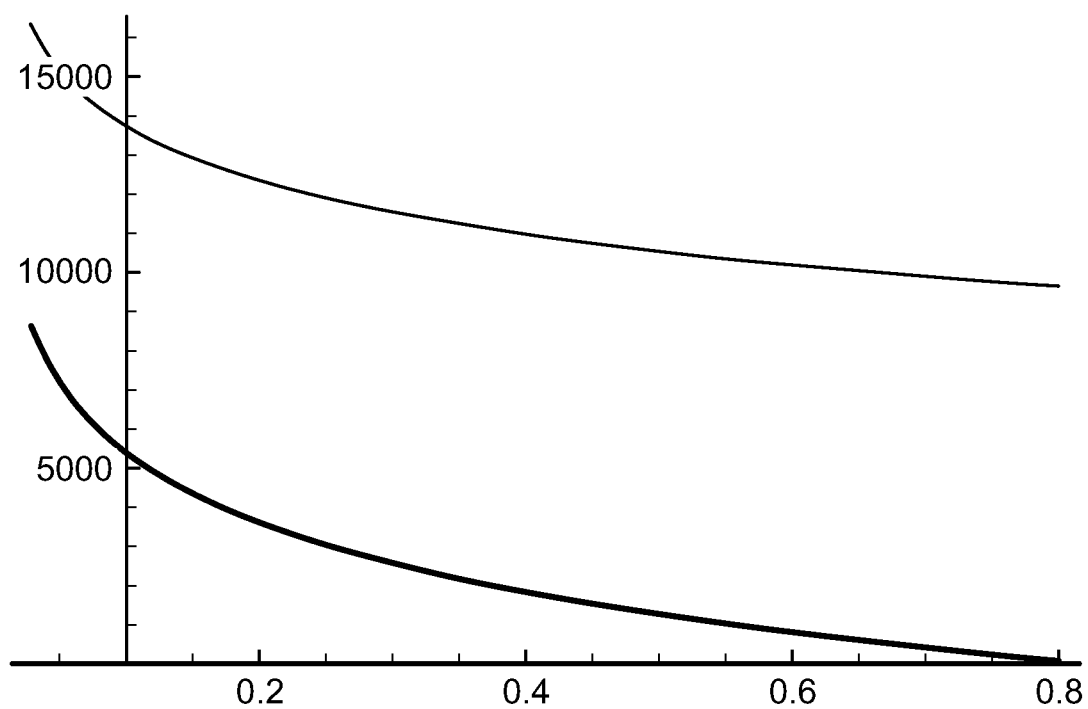
FIGS. 8A-8C are graphs depicting the average power density required for treatment and maximum allowable average treatment power at varying retinal spot diameters, in accordance with the present invention.
Figure 8B:
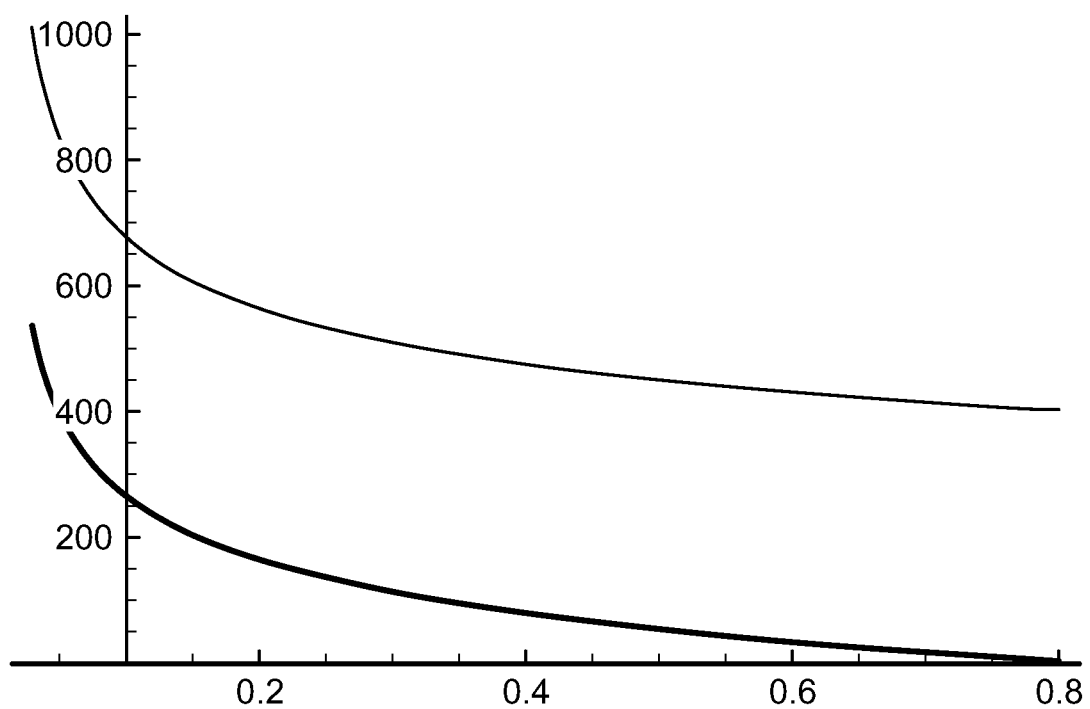
Figure 8C:
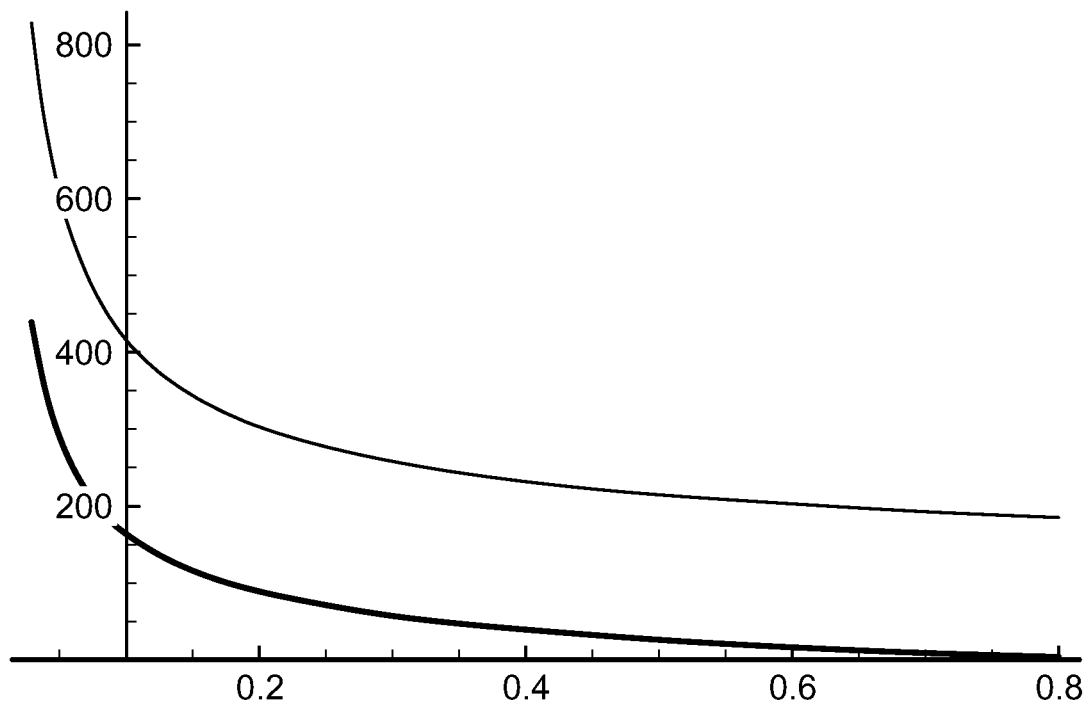

FIGS. 8A-8C illustrate the dependence of the required radiation power density (fluence) at the retina, on spot size and micro train duration. Accordingly, FIG. 8A has a retinal spot diameter of 10 microns, 8B a retinal spot diameter of 200 microns, and 8C a retinal spot diameter of 500 microns. Once again, a radiation wavelength of 810 nm is used. Although FIGS. 8A-8C could be obtained directly from FIGS. 7A-7C simply by dividing the powers of FIGS. 7A-7C by the areas of the spots, they are included for ease of reference.

FIGS. 7 and 8 show that as the treatment duration decreases, the required powers and power densities increase dramatically. Moreover, the larger the retinal spot treated, the larger is the required average power. Furthermore, the larger the retinal spot treated, the smaller is the required average power density. Although the power at a 500 micron spot is of the order of 75 times larger than the power at a 10 micron spot, the average power does not appear to be excessive. Similarly, for a 10 micron spot, the required power density is of the order of 34 times that for a 500 micron spot, but the higher power densities do not seem to be excessive. However, these treatment spot sizes represent an approximate upper and lower end of the sizes used in accordance with the present invention.

It should be noted, however, that the smaller the treatment spot, the more spots will be required to treat a given area of the retina. This will require a longer total treatment time, which is undesirable. Also, the longer treatment time for a spot, the longer will be the total time required for treating a given desired area of the retina.

There are also safety limits which must be taken into account in order to avoid destroying or permanently damaging the retinal tissue. There are limits on how short the radiation duration with associated increase in power density can be. For nanosecond or picosecond pulses of $10^{10}$-$10^{12}$ watts/cm$^2$ of near infrared lasers, such short pulses have been shown to create plasma in tissue which generates destructive shock waves. Photothermolysis with exploding tissue has been shown to occur with a 585 nm pulsed laser of 0.0005 seconds duration. Studies with an argon laser (514 nm) have been done to see when damage to the RPE occurs because of thermal effect and the shockwave/bubble generation effect. It was found that for a 5 microsecond pulse, RPE cell damage was always associated with microbubble formation. For a 50 microsecond pulse, the damage was due mostly to thermal denaturation effects, but there are also some microbubbles formed. For pulses longer than 500 microseconds, the damage was due to thermal effects. The damage mechanism changes from a purely thermal mechanism at longer pulses to a thermomechanical mechanism at short pulses, with the transition occurring at approximately 18 microseconds. It has also been found that short duration red or longer wavelength continuous wavelength laser applications (see the CW) are known to have an increased risk of rupturing Bruch's membrane by thermal explosion/bubble formation, and that can lead to choroidal neovascularation and visual loss.

From the foregoing, we can conclude about retinal spots and treatment times that in order to avoid long total treatment times and large radiation powers and power density, for a wavelength radiation of approximately 810 nm, a broad range of treatment times of 0.03 seconds to 0.8 seconds may be used, with a preferred range of treatment times of 0.1 seconds to 0.5 seconds. A broad range of retinal spot sizes usable in accordance with the present invention is 10 microns to 700 microns in diameter. However, a more preferable range of retinal spot sizes is 100-500 microns in diameter.

The below Tables 1-5 show the required treatment (reset) powers, damage powers, treatment (reset) power densities, and damage power densities at the extremes of the ranges for different wavelengths within the range of wavelengths usable in order to practice the present invention.

TABLE 1

Treatment power $P_{reset}$, damage power $P_{damage}$, treatment power densities at retina $P1_{reset}$, and threshold damage power densities at retina $P1_{damage}$ as a function of irradiation treatment time $t_F$ at a retinal radiation spot diameter, for $\lambda = 570$ nm. The powers are in watts, the power densities in watts/cm$^2$, time is in seconds, and spot diameters are in microns. The values of $t_F$ are those at the extremes of the suggested treatment ranges.

| tF sec seconds | Diameter μm | Preset watts | Pdamage watts | P1reset watts/sqcm | P1damage watts/sqcm |
|---|---|---|---|---|---|
| 0.03 | 10 | 0.001541 | 0.002944 | 1974 | 3737 |
|  | 200 | 0.03864 | 0.07291 | 122 | 232 |
|  | 500 | 0.19734 | 0.3726 | 100 | 190 |
| 0.1 | 10 | 0.000966 | 0.002484 | 1237 | 3156 |
|  | 200 | 0.019159 | 0.04876 | 60 | 155 |
|  | 500 | 0.0736 | 0.18768 | 37 | 95 |
| 0.5 | 10 | 0.00023 | 0.001909 | 284 | 2423 |
|  | 100 | 0.003818 | 0.032522 | 12 | 103 |
|  | 500 | 0.011362 | 0.096761 | 5 | 49 |
| 0.8 | 10 | 6.9E-06 | 0.001748 | 9.8 | 2213 |
|  | 100 | 0.000129 | 0.029026 | 0.41 | 94 |
|  | 500 | 0.000368 | 0.082846 | 0.18 | 42 |

TABLE 2

Treatment power $P_{reset}$, damage power $P_{damage}$, treatment power densities at retina $P1_{reset}$, and threshold damage power densities at retina $P1_{damage}$ as a function of irradiation treatment time $t_F$ at a retinal radiation spot diameter, for $\lambda = 600$ nm. The powers are in watts, the power densities in watts/cm$^2$, time is in seconds, and spot diameters are in microns. The values of $t_F$ are those at the extremes of the suggested treatment ranges.

| tF sec seconds | Diameter μm | Preset watts | Pdamage watts | P1reset watts/sqcm | P1damage watts/sqcm |
|---|---|---|---|---|---|
| 0.03 | 10 | 0.001809 | 0.003456 | 2317 | 4387 |
|  | 200 | 0.04536 | 0.08559 | 143 | 272 |
|  | 500 | 0.23166 | 0.4374 | 117 | 223 |
| 0.1 | 10 | 0.001134 | 0.002916 | 1452 | 3705 |
|  | 200 | 0.022491 | 0.05724 | 71 | 182 |
|  | 500 | 0.0864 | 0.22032 | 44 | 112 |
| 0.5 | 10 | 0.00027 | 0.002241 | 334 | 2844 |
|  | 100 | 0.004482 | 0.038178 | 14 | 121 |
|  | 500 | 0.013338 | 0.113589 | 6.8 | 57 |
| 0.8 | 10 | 8.1E-06 | 0.002052 | 11 | 2599 |
|  | 100 | 0.000151 | 0.034074 | 0.48 | 111 |

TABLE 2-continued

Treatment power $P_{reset}$, damage power $P_{damage}$, treatment power densities at retina $P_{1reset}$, and threshold damage power densities at retina $P_{1damage}$ as a function of irradiation treatment time $t_F$ at a retinal radiation spot diameter, for $\lambda = 600$ nm. The powers are in watts, the power densities in watts/cm$^2$, time is in seconds, and spot diameters are in microns. The values of $t_F$ are those at the extremes of the suggested treatment ranges.

| tF sec seconds | Diameter μm | Preset watts | Pdamage watts | P1reset watts/sqcm | P1damage watts/sqcm |
|---|---|---|---|---|---|
| | 500 | 0.000432 | 0.097254 | 0.21 | 49 |

TABLE 3

Treatment power $P_{reset}$, damage power $P_{damage}$, treatment power densities at retina $P_{1reset}$, and threshold damage power densities at retina $P_{1damage}$ as a function of irradiation treatment time $t_F$ at a retinal radiation spot diameter, for $\lambda = 810$ nm. The powers are in watts, the power densities in watts/cm$^2$, time is in seconds, and spot diameters are in microns. The values of $t_F$ are those at the extremes of the suggested treatment ranges.

| tFsec seconds | Diameter μm | Preset watts | Pdamage watts | P1reset watts/sqcm | P1damage watts/sqcm |
|---|---|---|---|---|---|
| 0.03 | 10 | 0.0067 | 0.0128 | 8583 | 16251 |
| | 200 | 0.168 | 0.317 | 533 | 1009 |
| | 500 | 0.858 | 1.62 | 437 | 828 |
| 0.1 | 10 | 0.0042 | 0.0108 | 5381 | 13723 |
| | 200 | 0.0833 | 0.212 | 265 | 677 |
| | 500 | 0.32 | 0.816 | 163 | 416 |
| 0.5 | 10 | 0.001 | 0.0083 | 1239 | 10536 |
| | 100 | 0.0166 | 0.1414 | 52 | 450 |
| | 500 | 0.0494 | 0.4207 | 25 | 214 |
| 0.8 | 10 | 0.00003 | 0.0076 | 42 | 9626 |
| | 100 | 0.00056 | 0.1262 | 1.7 | 412 |
| | 500 | 0.0016 | 0.3602 | 0.81 | 183 |

TABLE 4

Treatment power $P_{reset}$, damage power $P_{damage}$, treatment power densities at retina $P_{1reset}$, and threshold damage power densities at retina $P_{1damage}$ as a function of irradiation treatment time $t_F$ at a retinal radiation spot diameter, for $\lambda = 1100$ nm. The powers are in watts, the power densities in watts/cm$^2$, time is in seconds, and spot diameters are in microns. The values of $t_F$ are those at the extremes of the suggested treatment ranges.

| tFsec seconds | Diameter μm | Preset watts | Pdamage watts | P1reset watts/sqcm | P1damage watts/sqcm |
|---|---|---|---|---|---|
| 0.03 | 10 | 0.05695 | 0.1088 | 72955 | 138133 |
| | 200 | 1.428 | 2.6945 | 4530 | 8576 |
| | 500 | 7.293 | 13.77 | 3714 | 7038 |
| 0.1 | 10 | 0.0357 | 0.0918 | 45738 | 116645 |
| | 200 | 0.70805 | 1.802 | 2252 | 5754 |
| | 500 | 2.72 | 6.936 | 1385 | 3536 |
| 0.5 | 10 | 0.0085 | 0.07055 | 10531 | 89556 |
| | 100 | 0.1411 | 1.2019 | 449 | 3825 |
| | 500 | 0.4199 | 3.57595 | 214 | 1819 |
| 0.8 | 10 | 0.000255 | 0.0646 | 363 | 81821 |
| | 100 | 0.00476 | 1.0727 | 15 | 3502 |
| | 500 | 0.0136 | 3.0617 | 6.9 | 1555 |

TABLE 5

Treatment power $P_{reset}$, damage power $P_{damage}$, treatment power densities at retina $P_{1reset}$, and threshold damage power densities at retina $P_{1damage}$ as a function of irradiation treatment time $t_F$ at a retinal radiation spot diameter, for $\lambda = 1300$ nm. The powers are in watts, the power densities in watts/cm$^2$, time is in seconds, and spot diameters are in microns. The values of $t_F$ are those at the extremes of the suggested treatment ranges.

| tFsec seconds | Diameter μm | Preset watts | Pdamage watts | P1reset watts/sqcm | P1damage watts/sqcm |
|---|---|---|---|---|---|
| 0.03 | 10 | 0.3082 | 0.5888 | 394818 | 747546 |
| | 200 | 7.728 | 14.582 | 24518 | 46414 |
| | 500 | 39.468 | 74.52 | 20102 | 38088 |
| 0.1 | 10 | 0.1932 | 0.4968 | 247526 | 631258 |
| | 200 | 3.8318 | 9.752 | 12190 | 31142 |
| | 500 | 14.72 | 37.536 | 7498 | 19136 |
| 0.5 | 10 | 0.046 | 0.3818 | 56994 | 484656 |
| | 100 | 0.7636 | 6.5044 | 2433 | 20700 |
| | 500 | 2.2724 | 19.3522 | 1159 | 9844 |
| 0.8 | 10 | 0.00138 | 0.3496 | 1966 | 442796 |
| | 100 | 0.02576 | 5.8052 | 82 | 18952 |
| | 500 | 0.0736 | 16.5692 | 37 | 8418 |

The inventors have discovered that generating one or more radiation beams, such as coherent (laser) or non-coherent light beams within the range indicated above, with a corresponding appropriate duration, treatment spot size, and average radiation power or average radiation power density at the retina creates desirable retinal photostimulation without any visible burn areas or tissue destruction. Appropriate selection of the radiation generation and energy application parameters raises the retinal tissue at least up to a therapeutic level but below a cellular or tissue lethal level so as to avoid destroying, burning or otherwise damaging the retinal tissue. The appropriate combination of these parameters generates a subthreshold, sublethal micropulsed radiation light beam(s) which when appropriately applied to the retinal or other biological tissue heat stimulates the tissue sufficiently to create a therapeutic effect without destroying the tissue. The term "subthreshold" as used herein in connection with the invention means not only that no visible burn areas or tissue destruction is formed, but that the treated areas show no signs of burns, lesions or tissue damage ophthalmoscopically or angiographically, and thus is termed by the inventors as "true subthreshold" retinal photostimulation. Thus, the present invention can be used to treat the entire retina, including sensitive areas such as the fovea, without the risk of damage or vision loss. This is referred to herein as "subthreshold diode micropulse laser treatment" (SDM).

SDM does not produce laser-induced retinal damage (photocoagulation), and has no known adverse treatment effect, and has been reported to be an effective treatment in a number of retinal disorders (including diabetic macular edema (DME) proliferative diabetic retinopathy (PDR), macular edema due to branch retinal vein occlusion (BRVO), central serous chorioretinopathy (CSR), reversal of drug tolerance, and prophylactic treatment of progressive degenerative retinopathies such as dry age-related macular degeneration, Stargardts' disease, cone dystrophies, and retinitis pigmentosa. The safety of SDM is such that it may be used transfoveally in eyes with 20/20 visual acuity to reduce the risk of visual loss due to early fovea-involving DME.

A mechanism through which SDM might work is the generation or activation of heat shock proteins (HSPs). Despite a near infinite variety of possible cellular abnormalities, cells of all types share a common and highly conserved mechanism of repair: heat shock proteins (HSPs). HSPs are elicited almost immediately, in seconds to minutes, by almost any type of cell stress or injury. In the absence of lethal cell injury, HSPs are extremely effective at repairing and returning the viable cell toward a more normal functional state. Although HSPs are transient, generally peaking in hours and persisting for a few days, their effects may be long lasting. HSPs reduce inflammation, a common factor in many disorders.

Laser or other radiation treatment can induce HSP production or activation and alter cytokine expression. The more sudden and severe the non-lethal cellular stress (such as laser irradiation), the more rapid and robust HSP activation. Thus, a burst of repetitive low temperature thermal spikes at a very steep rate of change (~7° C. elevation with each 1001 μs micropulse, or 70,000° C./sec) produced by each SDM exposure is especially effective in stimulating activation of HSPs, particularly compared to non-lethal exposure to subthreshold treatment with continuous wave lasers, which can duplicate only the low average tissue temperature rise.

Laser or other radiation wavelengths below 550 nm produce increasingly cytotoxic photochemical effects. At 810 nm, SDM produces photothermal, rather than photochemical, cellular stress. Thus, SDM is able to affect the tissue without damaging it. The clinical benefits of SDM are thus primarily produced by sub-morbid photothermal cellular HSP activation. In dysfunctional cells, HSP stimulation by SDM results in normalized cytokine expression, and consequently improved structure and function. The therapeutic effects of this "low-intensity" laser/tissue interaction are then amplified by "high-density" laser application, recruiting all the dysfunctional cells in the targeted tissue area by densely/confluently treating a large tissue area, including all areas of pathology, thereby maximizing the treatment effect. These principles define the treatment strategy of SDM described herein.

Because normally functioning cells are not in need of repair, HSP stimulation in normal cells would tend to have no notable clinical effect. The "patho-selectivity" of near infrared laser effects, such as SDM, affecting sick cells but not affecting normal ones, on various cell types is consistent with clinical observations of SDM. SDM has been reported to have a clinically broad therapeutic range, unique among retinal laser modalities, consistent with American National Standards Institute "Maximum Permissible Exposure" predictions. While SDM may cause direct photothermal effects such as entropic protein unfolding and disaggregation, SDM appears optimized for clinically safe and effective stimulation of HSP-mediated repair.

As noted above, while SDM stimulation of HSPs is non-specific with regard to the disease process, the result of HSP mediated repair is by its nature specific to the state of the dysfunction. HSPs tend to fix what is wrong, whatever that might be. Thus, the observed effectiveness of SDM in retinal conditions as widely disparate as BRVO, DME, PDR, CSR, age-related and genetic retinopathies, and drug-tolerant NAMD. Conceptually, this facility can be considered a sort of "Reset to Default" mode of SDM action. For the wide range of disorders in which cellular function is critical, SDM normalizes cellular function by triggering a "reset" (to the "factory default settings") via HSP-mediated cellular repair.

The inventors have found that SDM treatment of patients suffering from age-related macular degeneration (AMD) can slow the progress or even stop the progression of AMD. Most of the patients have seen significant improvement in dynamic functional log MAR mesoptic visual acuity and mesoptic contrast visual acuity after the SDM treatment. It is believed that SDM works by targeting, preserving, and "normalizing" (moving toward normal) function of the retinal pigment epithelium (RPE).

SDM has also been shown to stop or reverse the manifestations of the diabetic retinopathy disease state without treatment-associated damage or adverse effects, despite the persistence of systemic diabetes mellitus. On this basis it is hypothesized that SDM might work by inducing a return to more normal cell function and cytokine expression in diabetes-affected RPE cells, analogous to hitting the "reset" button of an electronic device to restore the factory default settings. Based on the above information and studies, SDM treatment may directly affect cytokine expression via heat shock protein (HSP) activation in the targeted tissue. As heat shock proteins play a role in responding to a large number of abnormal conditions in body tissue other than eye tissue, it is believed that similar systems and methodologies can be advantageously used in treating such abnormal conditions, infections, etc.

As indicated above, subthreshold diode micropulse light (SDM) photostimulation has been effective in stimulating direct repair of slightly misfolded proteins in eye tissue. Besides HSP activation, another way this may occur is because the spikes in temperature caused by the micropulses in the form of a thermal time-course allows diffusion of water inside proteins, and this allows breakage of the peptide-peptide hydrogen bonds that prevent the protein from returning to its native state. The diffusion of water into proteins results in an increase in the number of restraining hydrogen bonds by a factor on the order of a thousand. Thus, it is believed that this process could be applied to other tissues and diseases advantageously as well.

As explained above, the energy source to be applied to the target tissue will have energy and operating parameters which must be determined and selected so as to achieve the therapeutic effect while not permanently damaging the tissue. Using a light beam energy source, such as a laser light beam, as an example, the laser wavelength, the radius of the laser treatment spot, the average laser power and total pulse train duration parameters must be taken into account. Adjusting or selecting one of these parameters can have an effect on at least one other parameter.

Figure 9A:
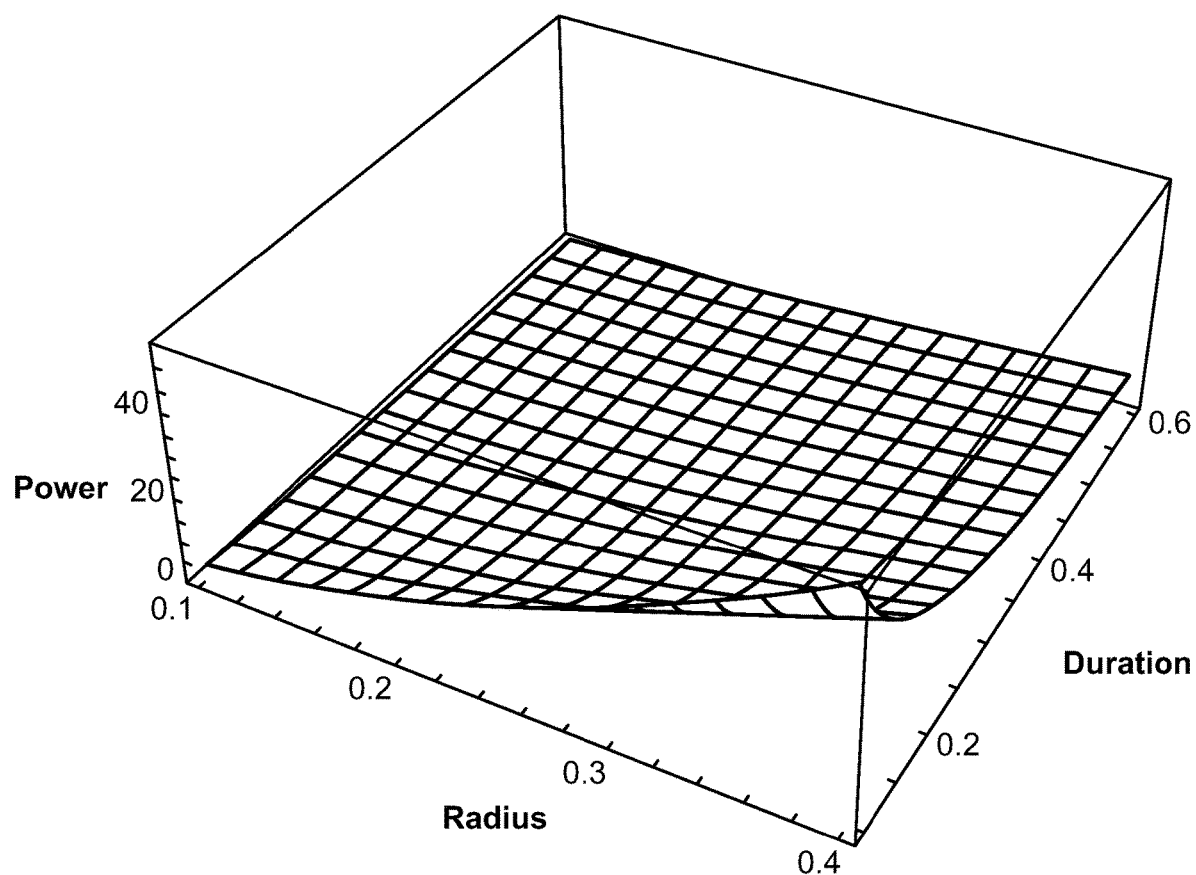
FIGS. 9A and 9B are graphs illustrating the average power of a laser source compared to a source radius and pulse train duration of the laser.
Figure 9B:
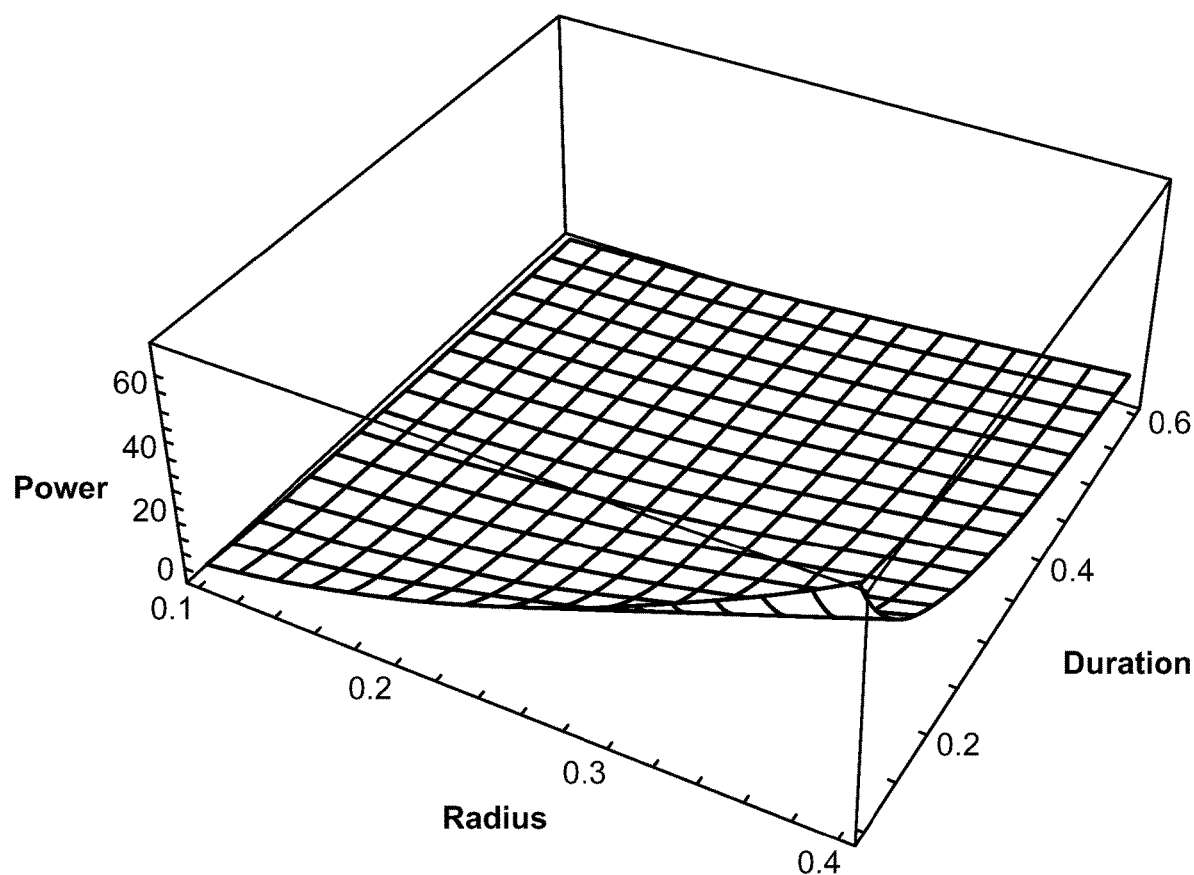

FIGS. 9A and 9B illustrate graphs showing the average power in watts as compared to the laser source radius (between 0.1 cm and 0.4 cm) and pulse train duration (between 0.1 and 0.6 seconds). FIG. 9A shows a wavelength of 880 nm, whereas FIG. 10B has a wavelength of 1000 nm. It can be seen in these figures that the required power decreases monotonically as the radius of the source decreases, as the total train duration increases, and as the wavelength decreases. The preferred parameters for the radius of the laser source is 1 mm-4 mm. For a wavelength of 880 nm, the minimum value of power is 0.55 watts, with a radius of the laser source being 1 mm, and the total pulse train duration being 600 milliseconds. The maximum value of power for the 880 nm wavelength is 52.6 watts when the laser source radius is 4 mm and the total pulse drain duration is 100 milliseconds. However, when selecting a laser having a wavelength of 1000 nm, the minimum power value is 0.77 watts with a laser source radius of 1 mm and a total pulse train duration of 600 milliseconds, and a maximum power value of 73.6 watts when the laser source radius is 4 mm and the total pulse duration is 100 milliseconds. The corresponding peak powers, during an individual pulse, are obtained from the average powers by dividing by the duty cycle.

The volume of the tissue region to be heated is determined by the wavelength, the absorption length in the relevant tissue, and by the beam width. The total pulse duration and the average laser power determine the total energy delivered to heat up the tissue, or power density per area of tissue, and the duty cycle of the pulse train gives the associated spike, or peak, power associated with the average laser power. Preferably, the pulsed energy source energy parameters are selected so that approximately 20 to 40 joules of energy is absorbed by each cubic centimeter of the target tissue.

The absorption length is very small in the thin melanin layer in the retinal pigmented epithelium. In other parts of the body, the absorption length is not generally that small. In wavelengths ranging from 400 nm to 2000 nm, the penetration depth and skin is in the range of 0.5 mm to 3.5 mm. The penetration depth into human mucous tissues is in the range of 0.5 mm to 6.8 mm. Accordingly, the heated volume will be limited to the exterior or interior surface where the radiation source is placed, with a depth equal to the penetration depth, and a transverse dimension equal to the transverse dimension of the radiation source. Since the light beam energy source is used to treat diseased tissues near external surfaces or near internal accessible surfaces, a source radii of between 1 mm to 4 mm and operating a wavelength of 880 nm yields a penetration depth of approximately 2.5 mm and a wavelength of 1000 nm yields a penetration depth of approximately 3.5 mm.

Figure 10A:
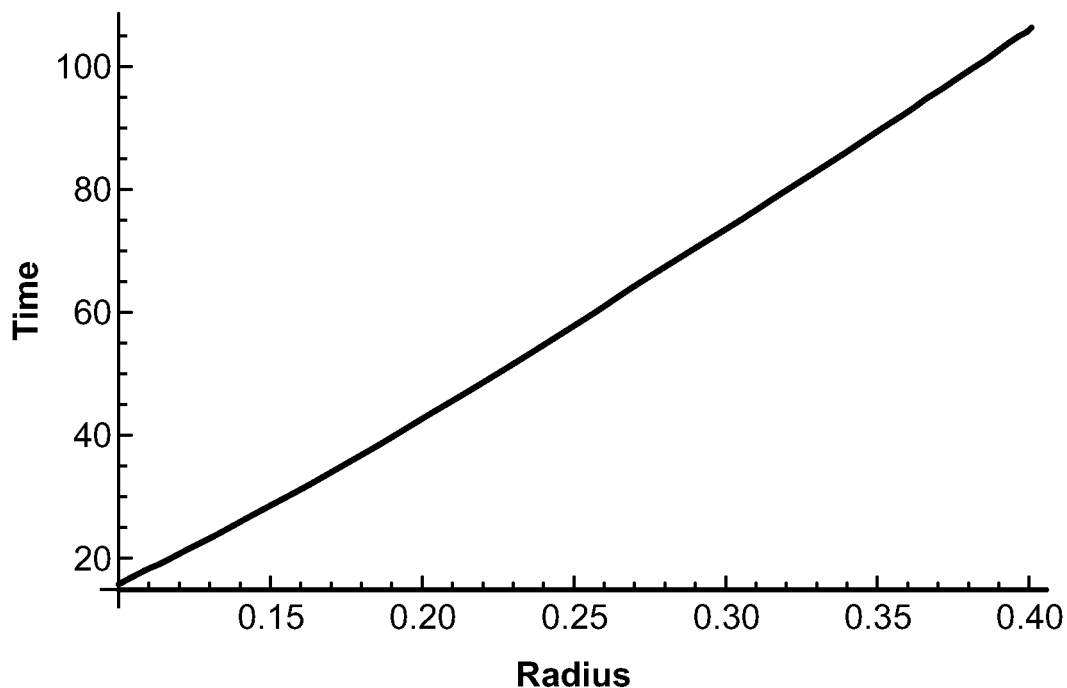
FIGS. 10A and 10B are graphs illustrating the time for the temperature to decay depending upon the laser source radius and wavelength.
Figure 10B:
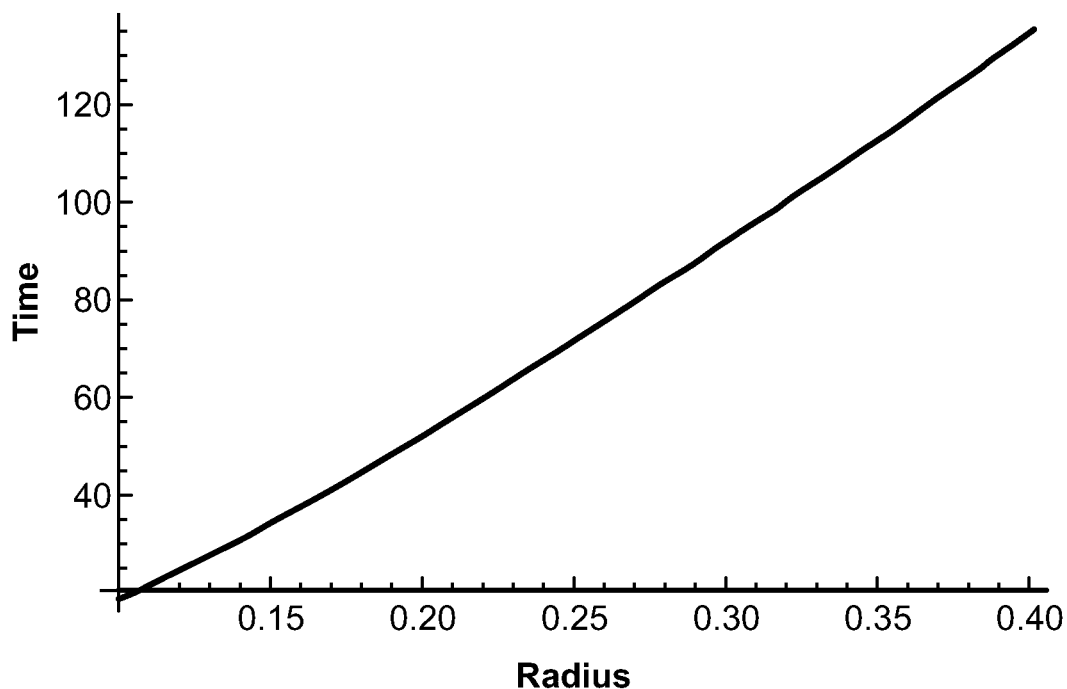

It has been determined that the target tissue can be heated to up to approximately 11° C. for a short period of time, such as less than one second, to create the therapeutic effect of the invention while maintaining the target tissue average temperature to a lower temperature range, such as less than 6° C. or even 1° C. or less over a prolonged period of time, such as several minutes. The selection of the duty cycle and the total pulse train duration provide time intervals in which the heat can dissipate. A duty cycle of less than 10%, and preferably between 2.5% and 5%, with a total pulse duration of between 100 milliseconds and 600 milliseconds has been found to be effective. FIGS. 10A and 10B illustrate the time to decay from 10° C. to 1° C. for a laser source having a radius of between 0.1 cm and 0.4 cm with the wavelength being 880 nm in FIG. 10A and 1000 nm in FIG. 10B. It can be seen that the time to decay is less when using a wavelength of 880 nm, but either wavelength falls within the acceptable requirements and operating parameters to achieve the benefits of the present invention while not causing permanent tissue damage.

It has been found that the average temperature rise of the desired target region increasing at least 6° C. and up to 11° C., and preferably approximately 10° C., during the total irradiation period results in HSP activation. The control of the target tissue temperature is determined by choosing source and target parameters such that the Arrhenius integral for HSP activation is larger than 1, while at the same time assuring compliance with the conservative FDA/FCC requirements for avoiding damage or a damage Arrhenius integral being less than 1.

In order to meet the conservative FDA/FCC constraints to avoid permanent tissue damage, for light beams and other electromagnetic radiation sources, the average temperature rise of the target tissue over any six-minute period is 1° C. or less. FIGS. 10A and 10B above illustrate the typical decay times required for the temperature in the heated target region to decrease by thermal diffusion from a temperature rise of approximately 10° C. to 1° C. as can be seen in FIG. 10A when the wavelength is 880 nm and the source diameter is 1 millimeter, the temperature decay time is 16 seconds. The temperature decay time is 107 seconds when the source diameter is 4 mm. As shown in FIG. 10B, when the wavelength is 1000 nm, the temperature decay time is 18 seconds when the source diameter is 1 mm and 136 seconds when the source diameter is 4 mm. This is well within the time of the average temperature rise being maintained over the course of several minutes, such as 6 minutes or less. While the target tissue's temperature is raised, such as to approximately 10° C., very quickly, such as in a fraction of a second during the application of the energy source to the tissue, the relatively low duty cycle provides relatively long periods of time between the pulses of energy applied to the tissue and the relatively short pulse train duration ensure sufficient temperature diffusion and decay within a relatively short period of time comprising several minutes, such as 6 minutes or less, that there is no permanent tissue damage.

The absorption properties of tissues differ. The tissue water content can vary from one tissue type to another, however, there is an observed uniformity of the properties of tissues at normal or near normal conditions which has allowed publication of tissue parameters that are widely used by clinicians in designing treatments. Below are tables illustrating the properties of electromagnetic waves in biological media, with Table 6 relating to muscle, skin and tissues with high water content, and Table 7 relating to fat, bone and tissues with low water content.

TABLE 6

Properties of Electromagnetic Waves in Biological Media:
Muscle, Skin, and Tissues with High Water Content

| Frequency (MHz) | Wavelength in Air (cm) | Dielectric Constant $\epsilon_H$ | Conductivity $\sigma_H$ (mho/m) | Wavelength $\lambda_H$ (cm) | Depth of Penetration (cm) | Reflection Coefficient Air-Muscle Interface | | Reflection Coefficient Muscle-Fat Interface | |
|---|---|---|---|---|---|---|---|---|---|
| | | | | | | r | ø | r | ø |
| 1 | 30000 | 2000 | 0.400 | 436 | 91.3 | 0.982 | +179 | | |
| 10 | 3000 | 160 | 0.625 | 118 | 21.6 | 0.956 | +178 | | |
| 27.12 | 1106 | 113 | 0.612 | 68.1 | 14.3 | 0.925 | +177 | 0.651 | −11.13 |
| 40.68 | 738 | 97.3 | 0.693 | 51.3 | 11.2 | 0.913 | +176 | 0.652 | −10.21 |
| 100 | 300 | 71.7 | 0.889 | 27 | 6.66 | 0.881 | +175 | 0.650 | −7.96 |
| 200 | 150 | 56.5 | 1.28 | 16.6 | 4.79 | 0.844 | +175 | 0.612 | −8.06 |
| 300 | 100 | 54 | 1.37 | 11.9 | 3.89 | 0.825 | +175 | 0.592 | −8.14 |
| 433 | 69.3 | 53 | 1.43 | 8.76 | 3.57 | 0.803 | +175 | 0.562 | −7.06 |
| 750 | 40 | 52 | 1.54 | 5.34 | 3.18 | 0.779 | +176 | 0.532 | −5.69 |
| 915 | 32.8 | 51 | 1.60 | 4.46 | 3.04 | 0.772 | +177 | 0.519 | −4.32 |
| 1500 | 20 | 49 | 1.77 | 2.81 | 2.42 | 0.761 | +177 | 0.506 | −3.66 |

TABLE 6-continued

Properties of Electromagnetic Waves in Biological Media:
Muscle, Skin, and Tissues with High Water Content

| Frequency (MHz) | Wavelength in Air (cm) | Dielectric Constant $\epsilon H$ | Conductivity $\sigma H$ (mho/m) | Wavelength $\lambda H$ (cm) | Depth of Penetration (cm) | Reflection Coefficient Air-Muscle Interface | | Muscle-Fat Interface | |
|---|---|---|---|---|---|---|---|---|---|
| | | | | | | r | ø | r | ø |
| 2450 | 12.2 | 47 | 2.21 | 1.76 | 1.70 | 0.754 | +177 | 0.500 | −3.88 |
| 3000 | 10 | 46 | 2.26 | 1.45 | 1.61 | 0.751 | +178 | 0.495 | −3.20 |
| 5000 | 6 | 44 | 3.92 | 0.89 | 0.788 | 0.749 | +177 | 0.502 | −4.95 |
| 5800 | 5.17 | 43.3 | 4.73 | 0.775 | 0.720 | 0.746 | +177 | 0.502 | −4.29 |
| 8000 | 3.75 | 40 | 7.65 | 0.578 | 0.413 | 0.744 | +176 | 0.513 | −6.65 |
| 10000 | 3 | 39.9 | 10.3 | 0.464 | 0.343 | 0.743 | +176 | 0.518 | −5.95 |

TABLE 7

Properties of Electromagnetic Waves in Biological Media:
Fat, Bone, and Tissues with Low Water Content

| Frequency (MHz) | Wavelength in Air (cm) | Dielectric Constant $\epsilon L$ | Conductivity $\sigma L$ (mmho/m) | Wavelength $\lambda L$ (cm) | Depth of Penetration (cm) | Reflection Coefficient Air-Fat Interface | | Fat-Muscle Interface | |
|---|---|---|---|---|---|---|---|---|---|
| | | | | | | r | ø | r | ø |
| 1 | 30000 | | | | | | | | |
| 10 | 3000 | | | | | | | | |
| 27.12 | 1106 | 20 | 10.9-43.2 | 241 | 159 | 0.660 | +174 | 0.651 | +169 |
| 40.68 | 738 | 14.6 | 12.6-52.8 | 187 | 118 | 0.617 | +173 | 0.652 | +170 |
| 100 | 300 | 7.45 | 19.1-75.9 | 106 | 60.4 | 0.511 | +168 | 0.650 | +172 |
| 200 | 150 | 5.95 | 25.8-94.2 | 59.7 | 39.2 | 0.458 | +168 | 0.612 | +172 |
| 300 | 100 | 5.7 | 31.6-107 | 41 | 32.1 | 0.438 | +169 | 0.592 | +172 |
| 433 | 69.3 | 5.6 | 37.9-118 | 28.8 | 26.2 | 0.427 | +170 | 0.562 | +173 |
| 750 | 40 | 5.6 | 49.8-138 | 16.8 | 23 | 0.415 | +173 | 0.532 | +174 |
| 915 | 32.8 | 5.6 | 55.6-147 | 13.7 | 17.7 | 0.417 | +173 | 0.519 | +176 |
| 1500 | 20 | 5.6 | 70.8-171 | 8.41 | 13.9 | 0.412 | +174 | 0.506 | +176 |
| 2450 | 12.2 | 5.5 | 96.4-213 | 5.21 | 11.2 | 0.406 | +176 | 0.500 | +176 |
| 3000 | 10 | 5.5 | 110-234 | 4.25 | 9.74 | 0.406 | +176 | 0.495 | +177 |
| 5000 | 6 | 5.5 | 162-309 | 2.63 | 6.67 | 0.393 | +176 | 0.502 | +175 |
| 5900 | 5.17 | 5.05 | 186-338 | 2.29 | 5.24 | 0.388 | +176 | 0.502 | +176 |
| 8000 | 3.75 | 4.7 | 255-431 | 1.73 | 4.61 | 0.371 | +176 | 0.513 | +173 − |
| 10000 | 3 | 4.5 | 324-549 | 1.41 | 3.39 | 0.363 | +175 | 0.518 | +174, − |

The pulse train mode of energy delivery has a distinct advantage over a single pulse or gradual mode of energy delivery, as far as the activation of remedial HSPs and the facilitation of protein repair is concerned. There are two considerations that enter into this advantage. First, a big advantage for HSP activation and protein repair in an SDM energy delivery mode comes from producing a spike temperature of the order of 10° C. This large rise in temperature has a big impact on the Arrhenius integrals that describe quantitatively the number of HSPs that are activated and the rate of water diffusion into the proteins that facilitates protein repair. This is because the temperature enters into an exponential that has a big amplification effect.

It is important that the temperature rise not remain at the high value (10° C. or more) for long, because then it would violate the FDA and FCC requirements that over periods of minutes the average temperature rise must be less than 1° C.

An SDM mode of energy delivery uniquely satisfies both of these foregoing considerations by judicious choice of the power, pulse time, pulse interval, and the volume of the target region to be treated. The volume of the treatment region enters because the temperature must decay from its high value of the order of 10° C. fairly rapidly in order for the long term average temperature rise not to exceed the long term FDA/FCC limit of 1° C. or less for electromagnetic radiation energy sources.

Figure 11:
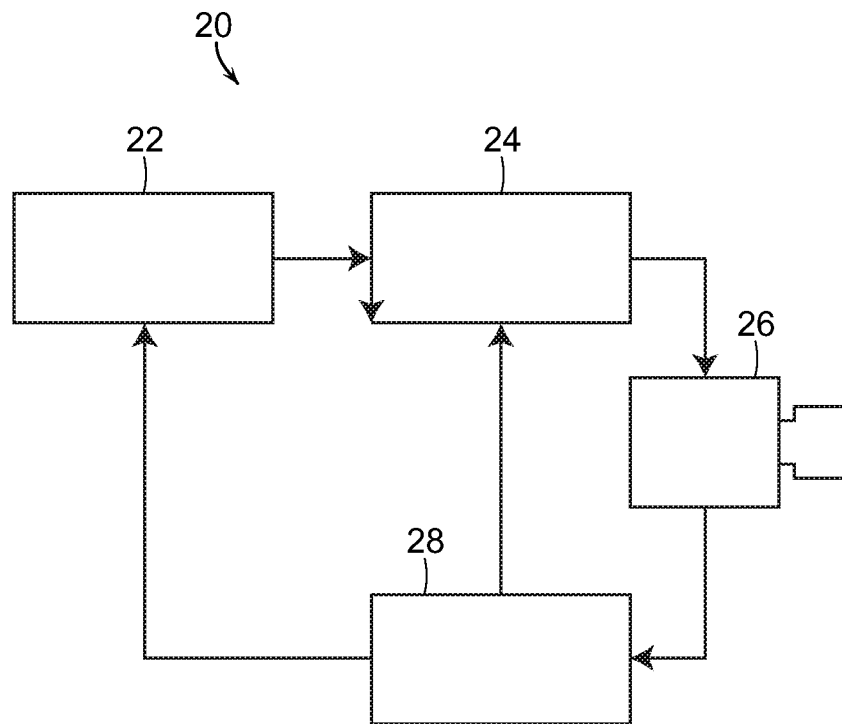
FIG. 11 is a diagrammatic view illustrating a system used to generate a laser light beam, in accordance with the present invention.

With reference now to FIG. 11, a schematic diagram is shown of a system for generating electromagnetic energy radiation, such as laser light, embodying SDM. The system, generally referred to by the reference number 20, includes a treatment radiation generator 22, such as for example the 810 nm near infrared micropulsed diode laser in the preferred embodiment. It will be understood that the treatment radiation may comprise electromagnetic radiation having a wavelength between 570 nm and 1300 nm, and as such may comprise coherent or non-coherent light beams. However, a coherent laser beam is particularly preferred and used in the description herein as an example.

The laser generates a laser light beam which is passed through optics, such as an optical lens and/or mask or a plurality of optical lenses and/or masks 24, as needed. The laser projector optics 24 pass the shaped light beam to a delivery device 26, for projecting the laser beam light onto the target tissue of the patient. It will be understood that the box labeled 26 can represent both the laser beam projector or delivery device as well as a viewing system/camera, such as an endoscope, or comprise two different components in use. The viewing system/camera 26 provides feedback to a display monitor 28, which may also include the necessary computerized hardware, data input and controls, etc. for manipulating the laser 22, the optics 24, and/or the projection/viewing components 26.

Figure 12:
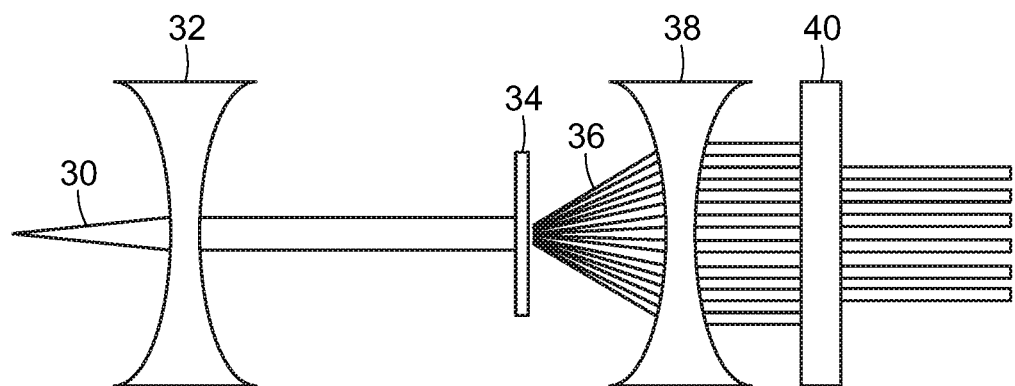
FIG. 12 is a diagrammatic view of optics used to generate a laser light geometric pattern, in accordance with the present invention.

With reference now to FIG. 12, in one embodiment, a plurality of radiation light beams are generated, each of which has parameters selected so that a target tissue temperature may be controllably raised to therapeutically treat the target tissue without destroying or permanently damaging the target tissue. This may be done, for example, by passing the laser light beam 30 through optics which diffract or otherwise generate a plurality of laser light beams from the single laser light beam 30 having the selected parameters. For example, the laser light beam 30 may be passed through a collimator lens 32 and then through a mask 34. In a particularly preferred embodiment, the mask 34 comprises a diffraction grating. The mask/diffraction grating 34 produces a geometric object, or more typically a geometric pattern of simultaneously produced multiple laser spots or other geometric objects. This is represented by the multiple laser light beams labeled with reference number 36. Alternatively, the multiple laser spots may be generated by a plurality of fiber optic waveguides.

Either method of generating laser spots allows for the creation of a large number of laser spots simultaneously over a very wide treatment field. In fact, a very high number of laser spots, perhaps numbering in the dozens or hundreds or more could be simultaneously generated to cover a given area of the target tissue, or possibly even the entirety of the target tissue. The present invention can use a plurality of simultaneously generated and applied therapeutic light beams or spots, such as numbering in the dozens or even hundreds, as the parameters and methodology of the present invention create therapeutically effective yet non-destructive and non-permanently damaging treatment. A wide array of simultaneously applied small separated laser spot applications may be desirable as such avoids certain disadvantages and treatment risks known to be associated with large laser spot applications.

Using optical features with a feature size on par with the wavelength of the laser employed, for example using a diffraction grating, it is possible to take advantage of quantum mechanical effects which permits simultaneous application of a very large number of laser spots for a very large target area. The individual spots produced by such diffraction gratings are all of a similar optical geometry to the input beam, with minimal power variation for each spot. The result is a plurality of laser spots with adequate irradiance to produce harmless yet effective treatment application, simultaneously over a large target area. The present invention also contemplates the use of other geometric objects and patterns generated by other diffractive optical elements.

The laser light passing through the mask 34 diffracts, producing a periodic pattern a distance away from the mask 34, shown by the laser beams labeled 36 in FIG. 12. The single laser beam 30 has thus been formed into dozens or even hundreds of individual laser beams 36 so as to create the desired pattern of spots or other geometric objects. These laser beams 36 may be passed through additional lenses, collimators, etc. 38 and 40 in order to convey the laser beams and form the desired pattern. Such additional lenses, collimators, etc. 38 and 40 can further transform and redirect the laser beams 36 as needed.

Arbitrary patterns can be constructed by controlling the shape, spacing and pattern of the optical mask 34. The pattern and exposure spots can be created and modified arbitrarily as desired according to application requirements by experts in the field of optical engineering. Photolithographic techniques, especially those developed in the field of semiconductor manufacturing, can be used to create the simultaneous geometric pattern of spots or other objects.

Although hundreds or even thousands of simultaneous laser spots could be generated and created and formed into patterns to be simultaneously applied to the tissue, due to the requirements of not overheating the tissue, there are constraints on the number of treatment spots or beams which can be simultaneously used in accordance with the present invention. Each individual laser beam or spot requires a minimum average power over a train duration to be effective. However, at the same time, tissue cannot exceed certain temperature rises without becoming damaged. For example, using an 810 nm wavelength laser, the number of simultaneous spots generated and used could number from as few as 1 and up to approximately 100 when a 0.04 (4%) duty cycle and a total train duration of 0.3 seconds (300 milliseconds) is used. The water absorption increases as the wavelength is increased. For shorter wavelengths, e.g., 577 nm, the laser power can be lower. For example, at 577 nm, the power can be lowered by a factor of 4 for the invention to be effective. Accordingly, there can be as few as a single laser spot or up to approximately 400 laser spots when using the 577 nm wavelength laser light, while still not harming or damaging the tissue.

Typically, the system of the present invention incorporates a guidance system to ensure complete and total retinal treatment with retinal photostimulation. Fixation/tracking/registration systems consisting of a fixation target, tracking mechanism, and linked to system operation can be incorporated into the present invention. In a particularly preferred embodiment, the geometric pattern of simultaneous laser spots is sequentially offset so as to achieve confluent and complete treatment of the surface.

Figure 13:
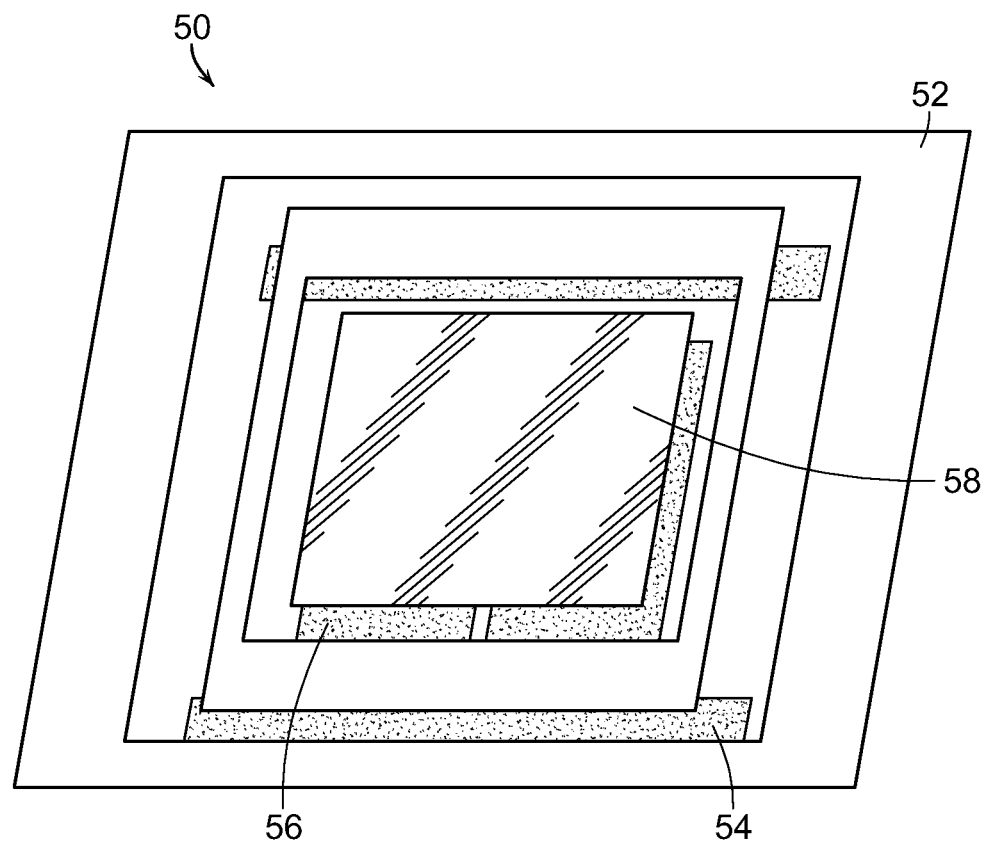
FIG. 13 is a top plan view of an optical scanning mechanism, used in accordance with the present invention.
Figure 14:
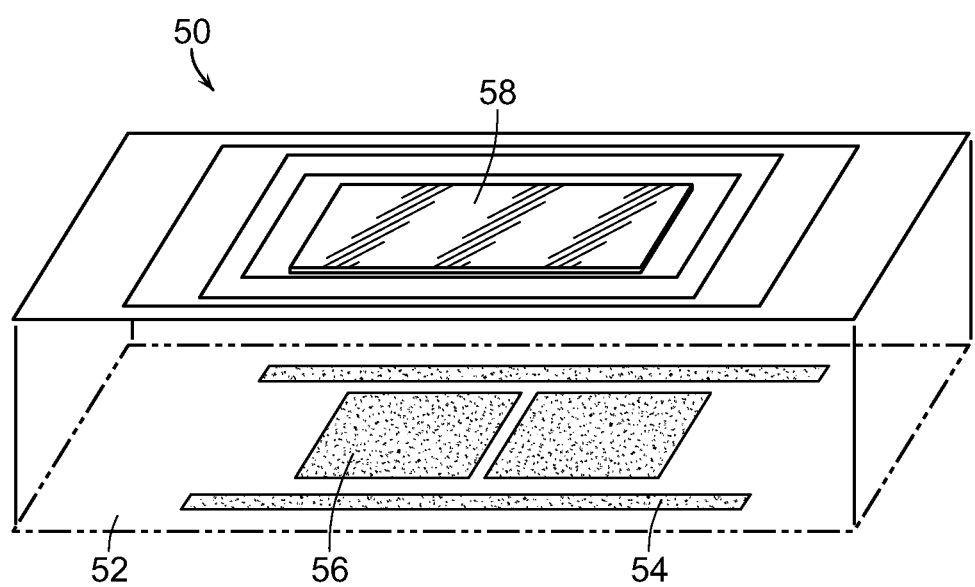
FIG. 14 is a partially exploded view of the optical scanning mechanism of FIG. 13, illustrating the various component parts thereof.

This can be done in a controlled manner using an optical scanning mechanism 50. FIGS. 13 and 14 illustrate an optical scanning mechanism 50 in the form of a MEMS mirror, having a base 52 with electronically actuated controllers 54 and 56 which serve to tilt and pan the mirror 58 as electricity is applied and removed thereto. Applying electricity to the controller 54 and 56 causes the mirror 58 to move, and thus the simultaneous pattern of laser spots or other geometric objects reflected thereon to move accordingly on the retina of the patient. This can be done, for example, in an automated fashion using electronic software program to adjust the optical scanning mechanism 50 until complete coverage of the retina, or at least the portion of the retina desired to be treated, is exposed to the phototherapy. The optical scanning mechanism may also be a small beam diameter scanning galvo mirror system, or similar system, such as that distributed by Thorlabs. Such a system is capable of scanning the lasers in the desired offsetting pattern.

Figure 15:
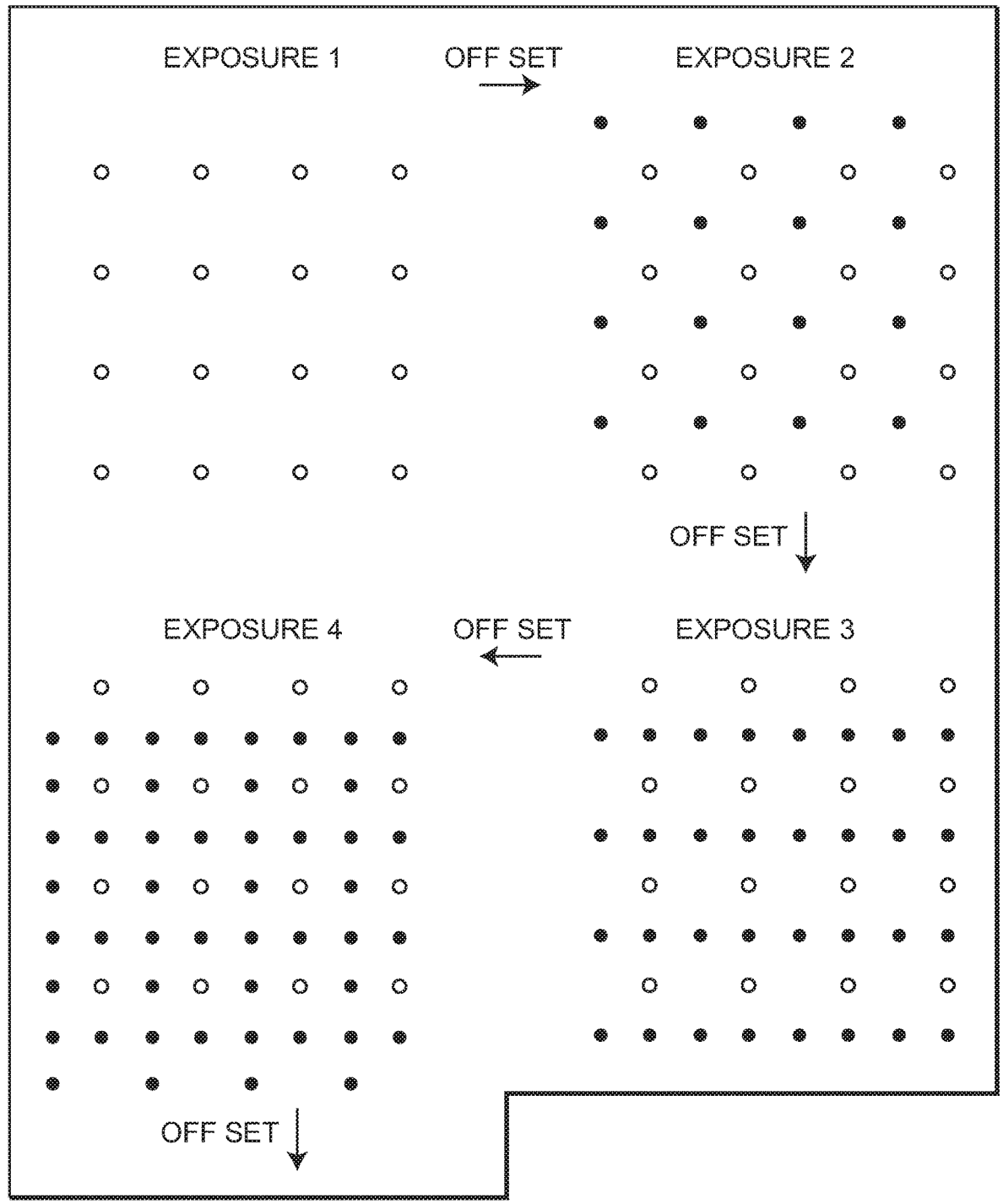
FIG. 15 illustrates controlled offsets of exposure of an exemplary geometric pattern grid of laser spots to treat the target tissue, in accordance with an embodiment of the present invention.

The pattern of spots are offset at each exposure so as to create space between the immediately previous exposure to allow heat dissipation and prevent the possibility of heat damage or tissue destruction. Thus, as illustrated in FIG. 15, the pattern, illustrated for exemplary purposes as a grid of sixteen spots, is offset each exposure such that the laser spots occupy a different space than previous exposures. It will be understood that the diagrammatic use of circles or empty dots as well as filled dots are for diagrammatic purposes only to illustrate previous and subsequent exposures of the pattern of spots to the area, in accordance with the present invention. The spacing of the laser spots prevents overheating and damage to the tissue. Typically, the treatment spots are spaced apart from one another by a distance of at least one-half diameter of the treatment spot, and more preferably between at least one and two diameters away from one another to prevent overheating and damage. It will be understood that this occurs until the entire target tissue to be treated has received phototherapy, or until the desired effect is attained. This can be done, for example, by applying electrostatic torque to a micromachined mirror, as illustrated in FIGS. 13 and 14. By combining the use of small laser spots separated by exposure free areas, prevents heat accumulation, and grids with a large number of spots per side, it is possible to atraumatically and invisibly treat large target areas with short exposure durations far more rapidly than is possible with current technologies.

By rapidly and sequentially repeating redirection or offsetting of the entire simultaneously applied grid array of spots or geometric objects, complete coverage of the target, can be achieved rapidly without thermal tissue injury. This offsetting can be determined algorithmically to ensure the fastest treatment time and least risk of damage due to thermal tissue, depending on laser parameters and desired application.

The following has been modeled using the Fraunhoffer Approximation. With a mask having a nine by nine square lattice, with an aperture radius 9 μm, an aperture spacing of 600 μm, using a 890 nm wavelength laser, with a mask-lens separation of 75 mm, and secondary mask size of 2.5 mm by 2.5 mm, the following parameters will yield a grid having nineteen spots per side separated by 133 μm with a spot size radius of 6 μm. The number of exposures "m" required to treat (cover confluently with small spot applications) given desired area side-length "A", given output pattern spots per square side "n", separation between spots "R", spot radius "r" and desired square side length to treat area "A", can be given by the following formula:

$$m = \frac{A}{nR} \text{floor}\left(\frac{R}{2r}\right)^2$$

With the foregoing setup, one can calculate the number of operations m needed to treat different field areas of exposure. For example, a 3 mm×3 mm area, which is useful for treatments, would require 98 offsetting operations, requiring a treatment time of approximately thirty seconds. Another example would be a 3 cm×3 cm area, representing the entire human retinal surface. For such a large treatment area, a much larger secondary mask size of 25 mm by 25 mm could be used, yielding a treatment grid of 190 spots per side separated by 133 μm with a spot size radius of 6 μm. Since the secondary mask size was increased by the same factor as the desired treatment area, the number of offsetting operations of approximately 98, and thus treatment time of approximately thirty seconds, is constant.

Of course, the number and size of spots produced in a simultaneous pattern array can be easily and highly varied such that the number of sequential offsetting operations required to complete treatment can be easily adjusted depending on the therapeutic requirements of the given application.

Furthermore, by virtue of the small apertures employed in the diffraction grating or mask, quantum mechanical behavior may be observed which allows for arbitrary distribution of the laser input energy. This would allow for the generation of any arbitrary geometric shapes or patterns, such as a plurality of spots in grid pattern, lines, or any other desired pattern. Other methods of generating geometric shapes or patterns, such as using multiple fiber optical fibers or microlenses, could also be used in the present invention. Time savings from the use of simultaneous projection of geometric shapes or patterns permits the treatment fields of novel size, such as the 1.2 cm² area to accomplish whole-retinal treatment, in a single clinical setting or treatment session.

Figure 16:
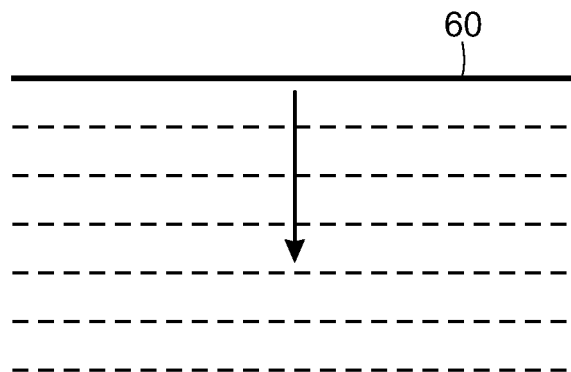
FIG. 16 is a diagrammatic view illustrating the use of a geometric object in the form of a line or bar controllably scanned to treat an area of the target tissue.

With reference now to FIG. 16, instead of a geometric pattern of small laser spots, the present invention contemplates use of other geometric objects or patterns. For example, a single line 60 of laser light, formed by the continuously or by means of a series of closely spaced spots, can be created. An offsetting optical scanning mechanism can be used to sequentially scan the line over an area, illustrated by the downward arrow in FIG. 16.

Figure 17:
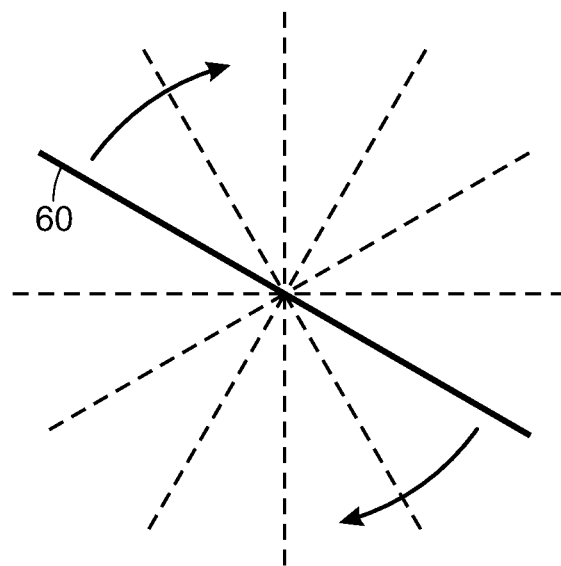
FIG. 17 is a diagrammatic view similar to FIG. 16, but illustrating the geometric line or bar rotated to treat the target tissue.

With reference now to FIG. 17, the same geometric object of a line 60 can be rotated, as illustrated by the arrows, so as to create a circular field of phototherapy. The potential negative of this approach, however, is that the central area will be repeatedly exposed, and could reach unacceptable temperatures. This could be overcome, however, by increasing the time between exposures, or creating a gap in the line such that the central area is not exposed.

The field of photobiology reveals that different biologic effects may be achieved by exposing target tissues to lasers of different wavelengths. The same may also be achieved by consecutively applying multiple lasers of either different or the same wavelength in sequence with variable time periods of separation and/or with different irradiant energies. The present invention anticipates the use of multiple laser, light or radiant wavelengths (or modes) applied simultaneously or in sequence to maximize or customize the desired treatment effects. This method also minimizes potential detrimental effects. The optical methods and systems illustrated and described above provide simultaneous or sequential application of multiple wavelengths.

Figure 18:
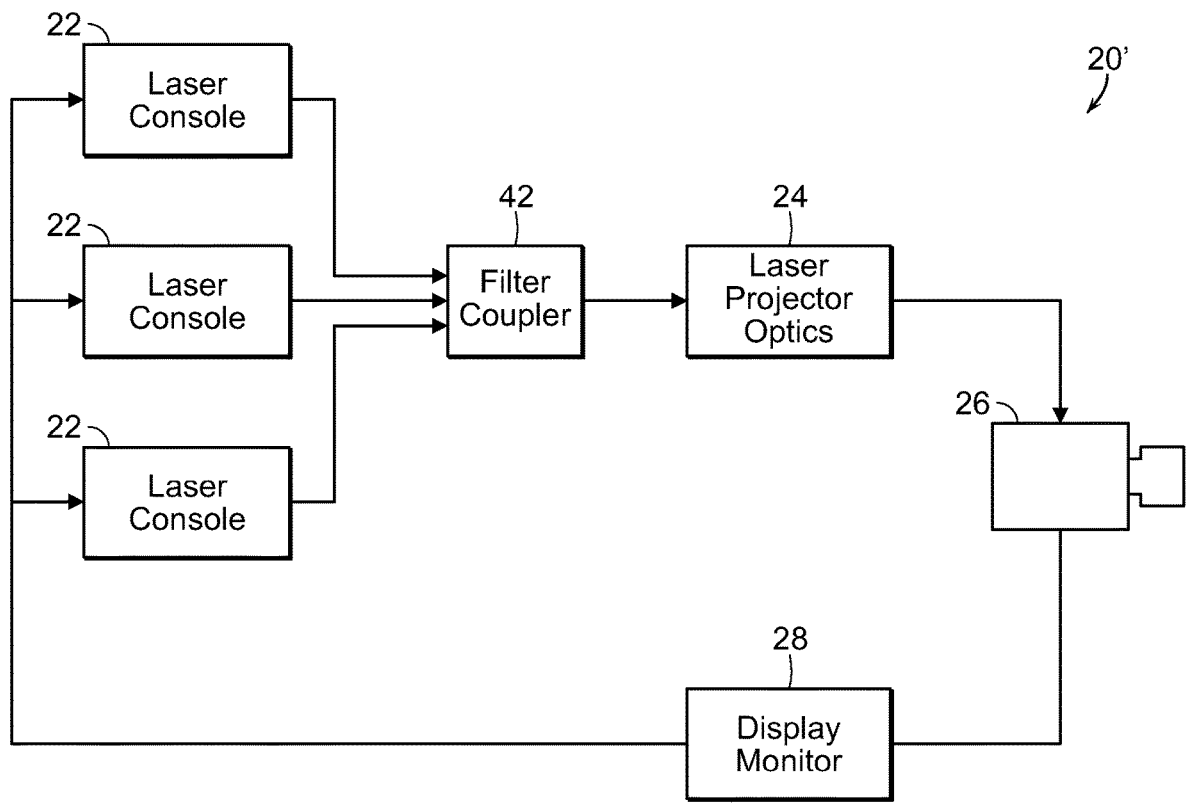
FIG. 18 is a diagrammatic view illustrating an alternate embodiment of the system used to generate laser light beams for treating tissue, in accordance with the present invention.

FIG. 18 illustrates diagrammatically a system which couples multiple treatment light sources into the pattern-generating optical subassembly described above. Specifically, this system 20' is similar to the system 20 described in FIG. 11 above. The primary differences between the alternate system 20' and the earlier described system 20 is the inclusion of a plurality of laser consoles, the outputs of which are each fed into a fiber coupler 42. Each laser console may supply a laser light beam having different parameters, such as of a different wavelength. The fiber coupler produces a single output that is passed into the laser projector optics 24 as described in the earlier system. The coupling of the plurality of laser consoles 22 into a single optical fiber is achieved with a fiber coupler 42 as is known in the art. Other known mechanisms for combining multiple light sources are available and may be used to replace the fiber coupler described herein.

In this system 20' the multiple light sources 22 follow a similar path as described in the earlier system 20, i.e., collimated, diffracted, recollimated, and directed to the projector device and/or tissue. However, the diffractive element functions differently than described earlier depending upon the wavelength of light passing through, which results in a slightly varying pattern. The variation is linear with the wavelength of the light source being diffracted. In general, the difference in the diffraction angles is small enough that the different, overlapping patterns may be directed along the same optical path through the projector device 26 to the tissue for treatment.

Since the resulting pattern will vary slightly for each wavelength, a sequential offsetting to achieve complete coverage will be different for each wavelength. This sequential offsetting can be accomplished in two modes. In the first mode, all wavelengths of light are applied simultaneously without identical coverage. An offsetting steering pattern to achieve complete coverage for one of the multiple wavelengths is used. Thus, while the light of the selected wavelength achieves complete coverage of the tissue, the application of the other wavelengths achieves either incomplete or overlapping coverage of the tissue. The second mode sequentially applies each light source of a varying wavelength with the proper steering pattern to achieve complete coverage of the tissue for that particular wavelength. This mode excludes the possibility of simultaneous treatment using multiple wavelengths, but allows the optical method to achieve identical coverage for each wavelength. This avoids either incomplete or overlapping coverage for any of the optical wavelengths.

These modes may also be mixed and matched. For example, two wavelengths may be applied simultaneously with one wavelength achieving complete coverage and the other achieving incomplete or overlapping coverage, followed by a third wavelength applied sequentially and achieving complete coverage.

Figure 19:
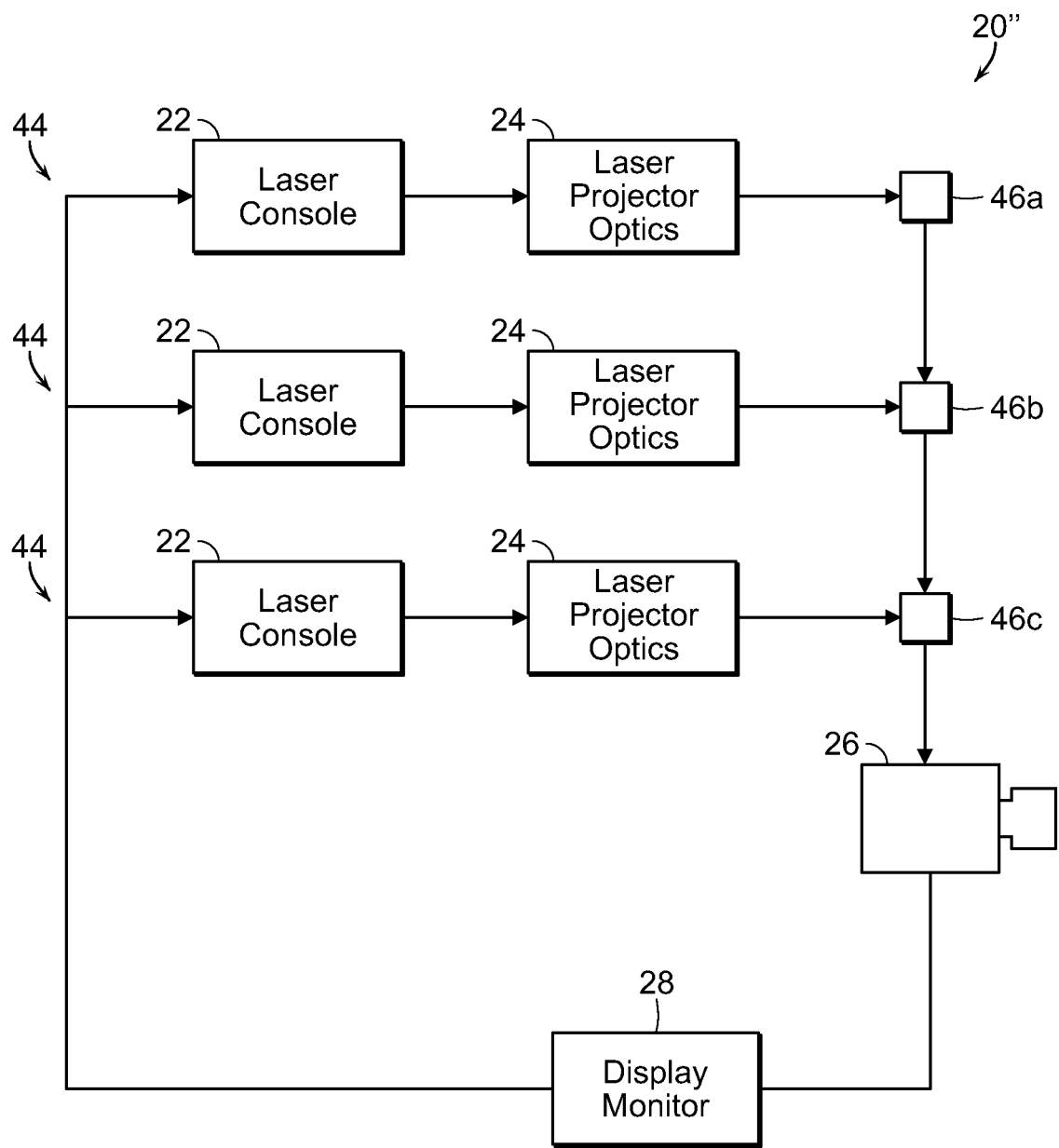
FIG. 19 is a diagrammatic view illustrating yet another embodiment of a system used to generate laser light beams to treat tissue in accordance with the present invention.

FIG. 19 illustrates diagrammatically yet another alternate embodiment of the inventive system 20". This system 20" is configured generally the same as the system 20 depicted in FIG. 11. The main difference resides in the inclusion of multiple pattern-generating subassembly channels tuned to a specific wavelength of the light source. Multiple laser consoles 22 are arranged in parallel with each one leading directly into its own laser projector optics 24. The laser projector optics of each channel 44a, 44b, 44c comprise a collimator 32, mask or diffraction grating 34 and recollimators 38, 40 as described in connection with FIG. 12 above—the entire set of optics tuned for the specific wavelength generated by the corresponding laser console 22. The output from each set of optics 24 is then directed to a beam splitter 46 for combination with the other wavelengths. It is known by those skilled in the art that a beam splitter used in reverse can be used to combine multiple beams of light into a single output. The combined channel output from the final beam splitter 46c is then directed through the projector device 26.

In this system 20" the optical elements for each channel are tuned to produce the exact specified pattern for that channel's wavelength. Consequently, when all channels are combined and properly aligned a single steering pattern may be used to achieve complete coverage of the tissue for all wavelengths. The system 20" may use as many channels 44a, 44b, 44c, etc. and beam splitters 46a, 46b, 46c, etc. as there are wavelengths of light being used in the treatment.

Implementation of the system 20" may take advantage of different symmetries to reduce the number of alignment constraints. For example, the proposed grid patterns are periodic in two dimensions and steered in two dimensions to achieve complete coverage. As a result, if the patterns for each channel are identical as specified, the actual pattern of each channel would not need to be aligned for the same steering pattern to achieve complete coverage for all wavelengths. Each channel would only need to be aligned optically to achieve an efficient combination.

In system 20", each channel begins with a light source 22, which could be from an optical fiber as in other embodiments of the pattern-generating subassembly. This light source 22 is directed to the optical assembly 24 for collimation, diffraction, recollimation and directed into the beam splitter which combines the channel with the main output.

It will be understood that the laser light generating systems illustrated in FIGS. 11-19 are exemplary. Other devices and systems can be utilized to generate a source of SDM light which can be operably passed through to a projector device.

The proposed treatment with a train of electromagnetic pulses has two major advantages over earlier treatments that incorporate a single short or sustained (long) pulse. First, the short (preferably subsecond) individual pulses in the train activate cellular reset mechanisms like HSP activation with larger reaction rate constants than those operating at longer (minute or hour) time scales. Secondly, the repeated pulses in the treatment provide large thermal spikes (on the order of 10,000) that allow the cell's repair system to more rapidly surmount the activation energy barrier that separates a dysfunctional cellular state from the desired functional state. The net result is a "lowered therapeutic threshold" in the sense that a lower applied average power and total applied energy can be used to achieve the desired treatment goal.

Power limitations in current micropulsed diode lasers require fairly long exposure duration. The longer the exposure, the more important the center-spot heat dissipating ability toward the unexposed tissue at the margins of the laser spot. Thus, the micropulsed laser light beam of an 810 nm diode laser should have an exposure envelope duration of 500 milliseconds or less, and preferably approximately 300 milliseconds. Of course, if micropulsed diode lasers become more powerful, the exposure duration should be lessened accordingly.

Aside from power limitations, another parameter of the present invention is the duty cycle, or the frequency of the train of micropulses, or the length of the thermal relaxation time between consecutive pulses. It has been found that the use of a 10% duty cycle or higher adjusted to deliver micropulsed laser at similar irradiance at similar MPE levels significantly increase the risk of lethal cell injury. However, duty cycles of less than 10%, and preferably 5% or less demonstrate adequate thermal rise and treatment at the level of the MPE cell to stimulate a biological response, but remain below the level expected to produce lethal cell injury. The lower the duty cycle, however, the exposure envelope duration increases, and in some instances can exceed 500 milliseconds.

Each micropulse lasts a fraction of a millisecond, typically between 50 microseconds to 100 microseconds in duration. Thus, for the exposure envelope duration of 300-500 milliseconds, and at a duty cycle of less than 5%, there is a significant amount of wasted time between micropulses to allow the thermal relaxation time between consecutive pulses. Typically, a delay of between 1 and 3 milliseconds, and preferably approximately 2 milliseconds, of thermal relaxation time is needed between consecutive pulses. For adequate treatment, the cells are typically exposed or hit between 50-200 times, and preferably between 75-150 at each location, and with the 1-3 milliseconds of relaxation or interval time, the total time in accordance with the embodiments described above to treat a given area which is being exposed to the laser spots is usually less than one second, such as between 100 milliseconds and 600 milliseconds on average. The thermal relaxation time is required so as not to overheat the cells within that location or spot and so as to prevent the cells from being damaged or destroyed. While time periods of 100-600 milliseconds do not seem long, given the small size of the laser spots and the need to treat a relatively large area of the target tissue, treating the entire target tissue take a significant amount of time, particularly for a patient who is undergoing treatment.

Accordingly, the present invention may utilize the interval between consecutive applications to the same location to apply energy to a second treatment area, or additional areas, of the target tissue that is spaced apart from the first treatment area. The pulsed energy is returned to the first treatment location, or previous treatment locations, within the predetermined interval of time so as to provide sufficient thermal relaxation time between consecutive pulses, yet also sufficiently treat the cells in those locations or areas properly by sufficiently increasing the temperature of those cells over time by repeatedly applying the energy to that location in order to achieve the desired therapeutic benefits of the invention.

It is important to return to a previously treated location within a predetermined amount of time to allow the area to cool down sufficiently during that time, but also to treat it within the necessary window of time. In the case of the light pulsed energy applications, the light is returned to the previously treated location within multi-milliseconds, such as one to three milliseconds, and preferably approximately two milliseconds. One cannot wait one or two seconds and then return to a previously treated area that has not yet received the full treatment necessary, as the treatment will not be as effective or perhaps not effective at all. However, during that interval of time, typically approximately 2 milliseconds, at least one other area, and typically multiple areas, can be treated with a laser light application as the laser light pulses are typically 50 seconds to 100 microseconds in duration. This is referred to herein as microshifting. The number of additional areas which can be treated is limited only by the micropulse duration and the ability to controllably move the light beams from one area to another.

Currently, approximately four additional areas which are sufficiently spaced apart from one another can be treated during the thermal relaxation intervals beginning with a first treatment area. Thus, multiple areas can be treated, at least partially, during the 200-500 millisecond exposure envelope for the first area. Thus, in a single interval of time, instead of only 100 simultaneous light spots being applied to a treatment area, approximately 500 light spots can be applied during that interval of time in different treatment areas. This would be the case, for example, for a laser light beam having a wavelength of 810 nm. For shorter wavelengths, such as 572 nm, even a greater number of individual locations can be exposed to the laser beams to create light spots. Thus, instead of a maximum of approximately 400 simultaneous spots, approximately 2,000 spots could be covered during the interval between micropulse treatments to a given area or location. Typically each location has between 50-200, and more typically between 75-150, light applications applied thereto over the course of the exposure envelope duration (typically 200-500 milliseconds) to achieve the desired treatment. In accordance with an embodiment of the present invention, the light would be reapplied to previously treated areas in sequence during the relaxation time intervals for each area or location. This would occur repeatedly until a predetermined number of laser light applications to each area to be treated have been achieved.

The pulsed energy could be reapplied to a previously treated area in sequence during the relaxation time intervals for each area or location until a desired number of applications has been achieved to each treatment area. The treatment areas must be separated by at least a predetermined minimum distance to enable thermal relaxation and heat dissipation and avoid thermal tissue damage. The pulsed energy and application parameters are selected so as to raise the target tissue temperature up to 11° C., such as between approximately 6°–11° C., during application of the pulsed energy source to the target tissue to achieve a therapeutic effect, such as by stimulating HSP production within the cells. However, the cells of the target tissue must be given a period of time to dissipate the heat such that the average temperature rise of the tissue over several minutes is maintained at or below a predetermined level, 1° C. or less over several minutes, so as not to permanently damage the target tissue.

Figure 20A:
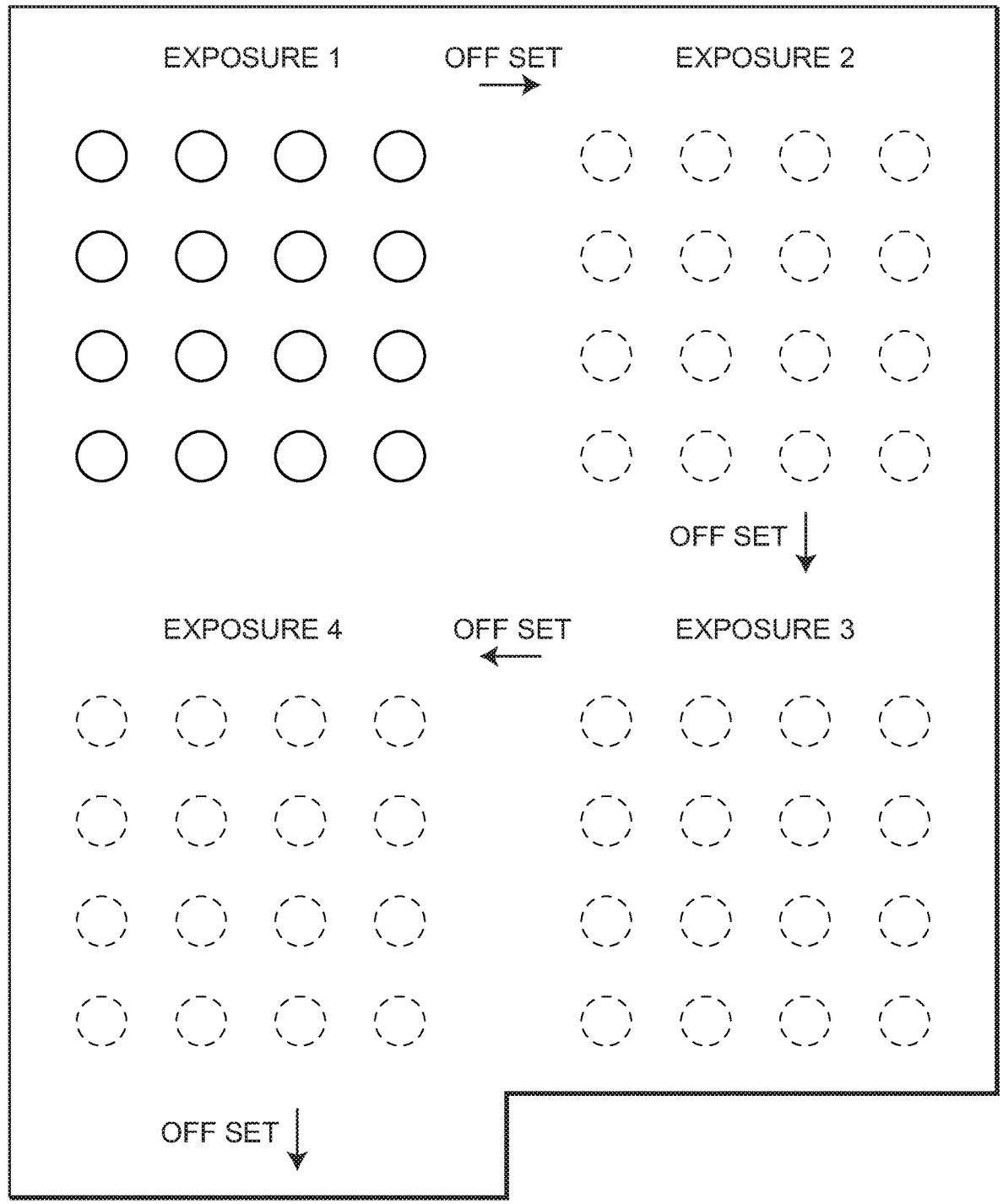
FIGS. 20A-20D are diagrammatic views illustrated in the application of micropulsed energy to different treatment areas during a predetermined interval of time, within a single treatment session, and reapplying the energy to previously treated areas, in accordance with the present invention.
Figure 20B:
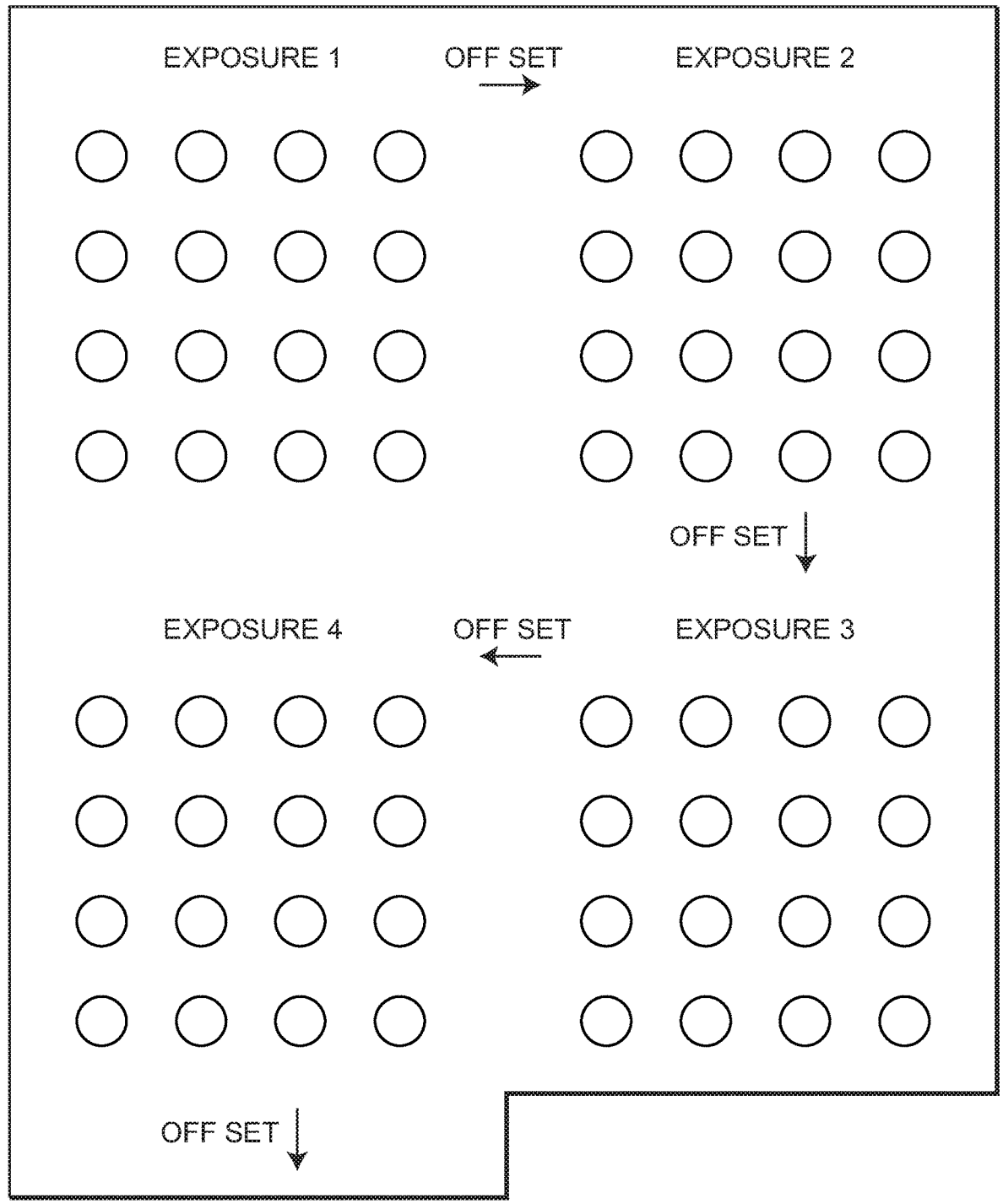
Figure 20C:
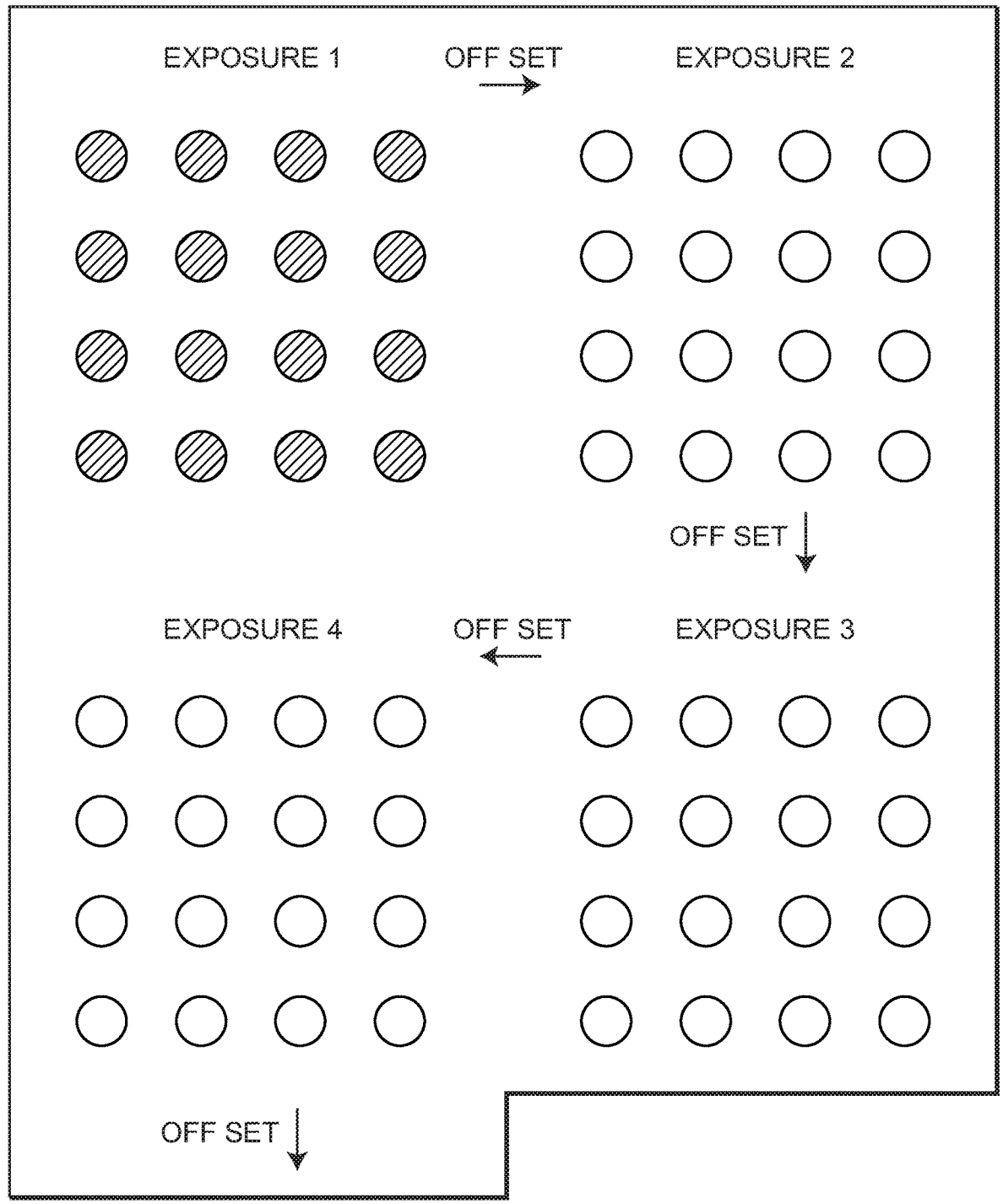
Figure 20D:
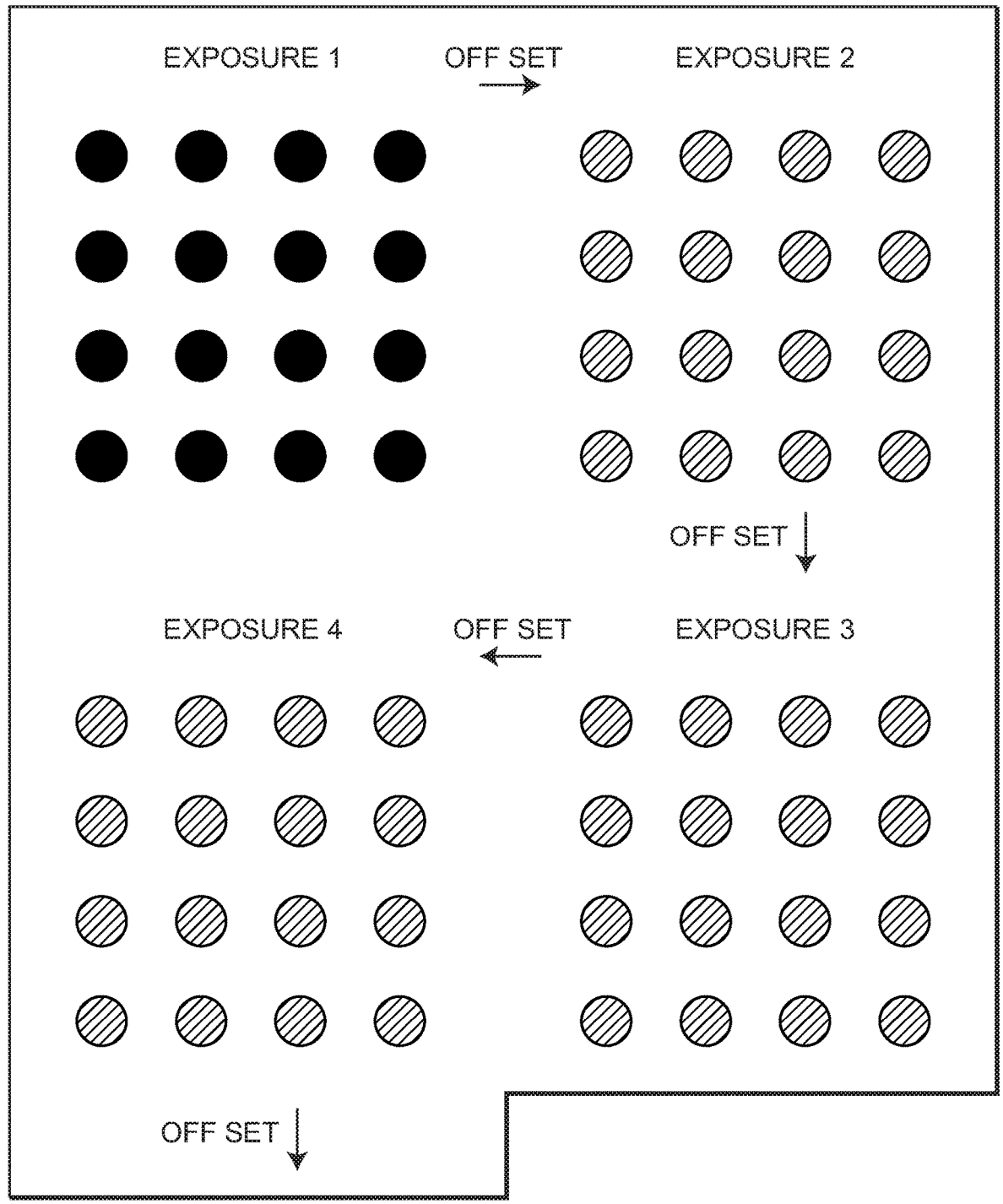

This is diagrammatically illustrated in FIGS. 20A-20D. FIG. 20A illustrates with solid circles a first area having energy beams, such as laser light beams, applied thereto as a first application. The beams are controllably offset or microshifted to a second exposure area, followed by a third exposure area and a fourth exposure area, as illustrated in FIG. 20B, until the locations in the first exposure area need to be re-treated by having beams applied thereto again within the thermal relaxation time interval. The locations within the first exposure area would then have energy beams reapplied thereto, as illustrated in FIG. 20C. Secondary or subsequent exposures would occur in each exposure area, as illustrated in FIG. 20D by the increasingly shaded dots or circles until the desired number of exposures or hits or applications of energy to the target tissue area has been achieved to therapeutically treat these areas, diagrammatically illustrated by the blackened circles in exposure area 1 in FIG. 20D. When a first or previous exposure area has been completed treated, this enables the system to add an additional exposure area, which process is repeated until the entire area to be treated has been fully treated. It should be understood that the use of solid circles, broken line circles, partially shaded circles, and fully shaded circles are for explanatory and illustration purposes only, as in fact the exposure of the energy or laser light in accordance with the present invention is invisible and non-detectable to both the human eye as well as known detection devices and techniques.

Adjacent exposure areas must be separated by at least a predetermined minimum distance to avoid thermal tissue damage. Such distance is at least 0.5 diameter away from the immediately preceding treated location or area, and more preferably between 1-2 diameters away. Such spacing relates to the actually treated locations in a previous exposure area. It is contemplated by the present invention that a relatively large area may actually include multiple exposure areas therein which are offset in a different manner than that illustrated in FIG. 20. For example, the exposure areas could comprise the thin lines illustrated in FIGS. 16 and 17, which would be repeatedly exposed in sequence until all of the necessary areas were fully exposed and treated. In accordance with the present invention, the time required to treat that area to be treated is significantly reduced, such as by a factor of 4 or 5 times, such that a single treatment session takes much less time for the medical provider and the patient need not be in discomfort for as long of a period of time.

Figure 21:
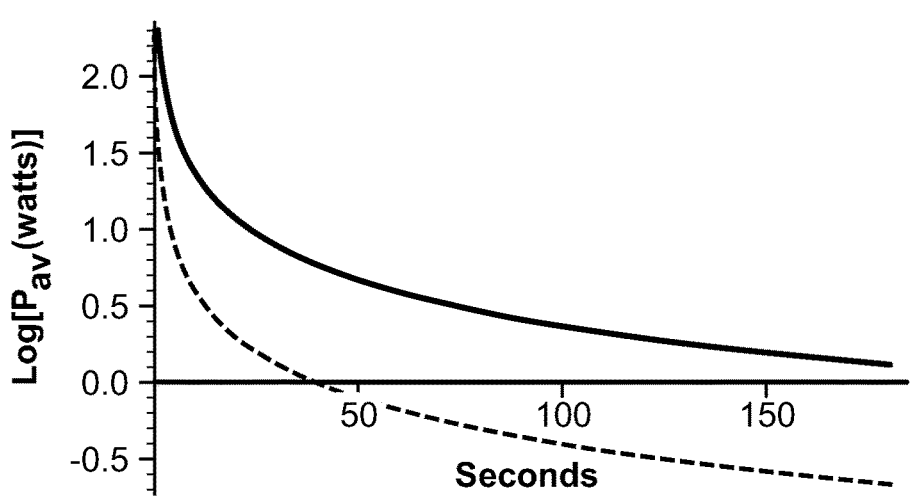
FIGS. 21-23 are graphs depicting the relationship of treatment power and time in accordance with the embodiments of the present invention.
Figure 22:
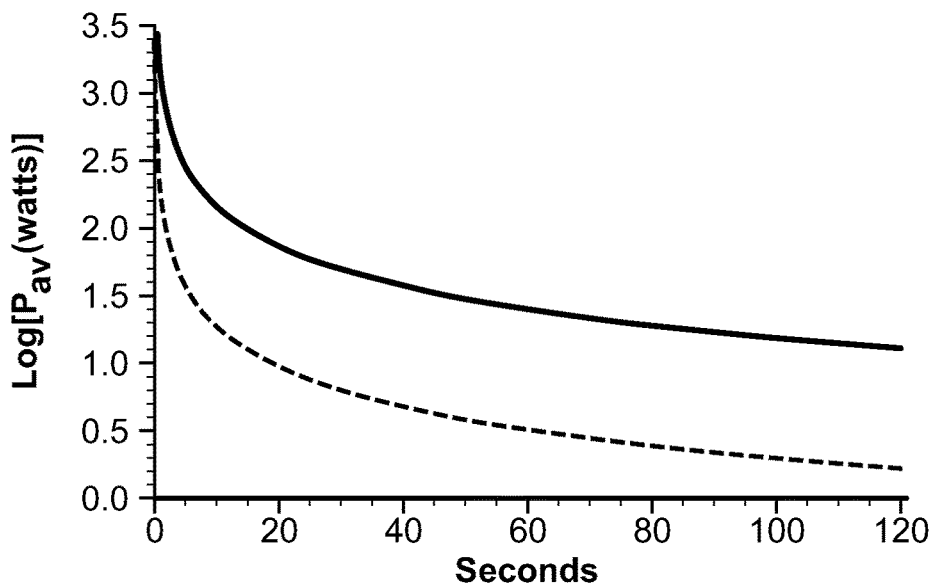
Figure 23:
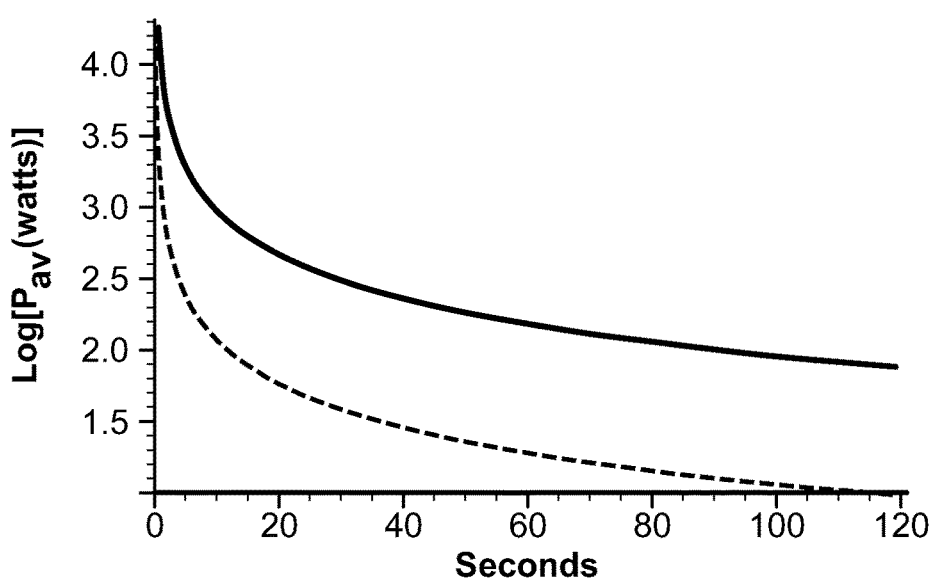

In accordance with this embodiment of the invention of applying one or more treatment beams at once, and moving the treatment beams to a series of new locations, then bringing the beams back to re-treat the same location or area repeatedly has been found to also require less power compared to the methodology of keeping the beams in the same locations or area during the entire exposure envelope duration. With reference to FIGS. 21-23, there is a linear relationship between the pulse length and the power necessary, but there is a logarithmic relationship between the heat generated.

With reference to FIG. 21, a graph is provided wherein the x-axis represents the Log of the average power in watts of a laser and the y-axis represents the treatment time, in seconds. The lower curve is for panmacular treatment and the upper curve is for panretinal treatment. This would be for a laser light beam having a micropulse time of 50 microseconds, a period of 2 milliseconds of time between pulses, and duration of train on a spot of 300 milliseconds. The areas of each retinal spot are 100 microns, and the laser power for these 100 micron retinal spots is 0.74 watts. The panmacular area is $0.55^2$, requiring 7,000 panmacular spots total, and the panretinal area is $3.30^2$, requiring 42,000 laser spots for full coverage. Each RPE spot requires a minimum energy in order for its reset mechanism to be adequately activated, in accordance with the present invention, namely, 38.85 joules for panmacular and 233.1 joules for panretinal. As would be expected, the shorter the treatment time, the larger the required average power. However, there is an upper limit on the allowable average power, which limits how short the treatment time can be.

As mentioned above, there are not only power constraints with respect to the laser light available and used, but also the amount of power that can be applied to the eye without damaging eye tissue. For example, temperature rise in the lens of the eye is limited, such as approximately 4° C. so as not to overheat and damage the lens, such as causing cataracts. Thus, an average power of 7.52 watts could elevate the lens temperature to approximately 4° C. This limitation in power increases the minimum treatment time.

However, with reference to FIG. 22, the total power per pulse required is less in the microshift case of repeatedly and sequentially moving the laser spots and returning to prior treated locations, so that the total energy delivered and the total average power during the treatment time is the same. FIGS. 22 and 23 show how the total power depends on treatment time. This is displayed in FIG. 22 for panmacular treatment, and in FIG. 23 for panretinal treatment. The upper, solid line or curve represents the embodiment where there are no microshifts taking advantage of the thermal relaxation time interval, such as described and illustrated in FIG. 15, whereas the lower dashed line represents the situation for such microshifts, as described and illustrated in FIG. 20. FIGS. 21 and 22 show that for a given treatment time, the peak total power is less with microshifts than without microshifts. This means that less power is required for a given treatment time using the microshifting embodiment of the present invention. Alternatively, the allowable peak power can be advantageously used, reducing the overall treatment time.

Thus, in accordance with FIGS. 21-23, a log power of 1.0 (10 watts) would require a total treatment time of 20 seconds using the microshifting embodiment of the present invention, as described herein. It would take more than 2 minutes of time without the microshifts, and instead leaving the micropulsed light beams in the same location or area during the entire treatment envelope duration. There is a minimum treatment time according to the wattage. However, this treatment time with microshifting is much less than without microshifting. As the laser power required is much less with the microshifting, it is possible to increase the power in some instances in order to reduce the treatment time for a given desired retinal treatment area. The product of the treatment time and the average power is fixed for a given treatment area in order to achieve the therapeutic treatment in accordance with the present invention. This could be implemented, for example, by applying a higher number of therapeutic laser light beams or spots simultaneously at a reduced power. Of course, since the parameters of the laser light are selected to be therapeutically effective yet not destructive or permanently damaging to the cells, no guidance or tracking beams are required, only the treatment beams as all areas can be treated in accordance with the present invention.

Although the present invention is described for use in connection with a micropulsed laser, theoretically a continuous wave laser could potentially be used instead of a micropulsed laser. However, with the continuous wave laser, there is concern of overheating as the laser is moved from location to location in that the laser does not stop and there could be heat leakage and overheating between treatment areas. Thus, while it is theoretically possible to use a continuous wave laser, in practice it is not ideal and the micropulsed laser is preferred.

While the information provided in connection with graphs 21-23 is derived from observations and calculations of light beams as the energy source applied to retinal eye tissue, it is believed that applying such pulsed light to other tissue will achieve similar results in that moving the treatment beams to a series of new locations, then bringing the beams back to re-treat the same location or area repeatedly will not only save time but also require less power compared to the methodology of keeping the beams in the same location or area during the entire exposure envelope duration.

In accordance with the microshifting technique described above, the shifting or steering of the pattern of light beams may be done by use of an optical scanning mechanism, such as that illustrated and described in connection with FIGS. 13 and 14.

Steering for energy sources may be done by use of multiple sources which provide an "array". The basic idea for steering the illumination radiation pattern of an array is constructive (and destructive) interference between the radiation from the individual members of the array of sources.

As mentioned above, the controlled manner of applying energy to the target tissue is intended to raise the temperature of the target tissue to therapeutically treat the target tissue without destroying or permanently damaging the target tissue. It is believed that such heating activates HSPs and that the thermally activated HSPs work to reset the diseased tissue to a healthy condition, such as by removing and/or repairing damaged proteins. It is believed by the inventors that maximizing such HSP activation improves the therapeutic effect on the targeted tissue. As such, understanding the behavior and activation of HSPs and HSP system species, their generation and activation, temperature ranges for activating HSPs and time frames of the HSP activation or generation and deactivation can be utilized to optimize the heat treatment of the biological target tissue.

As mentioned above, the target tissue is heated by the pulsed energy for a short period of time, such as ten seconds or less, and typically less than one second, such as between 100 milliseconds and 600 milliseconds. The time that the energy is actually applied to the target tissue is typically much less than this in order to provide intervals of time for heat relaxation so that the target tissue does not overheat and become damaged or destroyed. For example, as mentioned above, laser light pulses may last on the order of microseconds with several milliseconds of intervals of relaxed time.

Thus, understanding the sub-second behaviors of HSPs can be important to the present invention. The thermal activation of the HSPs in SDM is typically described by an associated Arrhenius integral, $$\Omega = \int dt A \exp[-E/k_B T(t)] \quad [1]$$

where the integral is over the treatment time and
  A is the Arrhenius rate constant for HSP activation
  E is the activation energy
  T(t) is the temperature of the thin RPE layer, including the laser-induced temperature rise The laser-induced temperature rise—and therefore the activation Arrhenius integral—depends on both the treatment parameters (e.g., laser power, duty cycle, total train duration) and on the RPE properties (e.g., absorption coefficients, density of HSPs). It has been found clinically that effective SDM treatment is obtained when the Arrhenius integrals is of the order of unity.

The Arrhenius integral formalism only takes into account a forward reaction, i.e. only the HSP activation reaction): It does not take into account any reverse reactions in which activated HSPs are returned to their inactivated states. For the typical subsecond durations of SDM treatments, this appears to be quite adequate. However, for longer periods of time (e.g. a minute or longer), this formalism is not a good approximation: At these longer times, a whole series of reactions occurs resulting in much smaller effective HSP activation rates. This is the case during the proposed minute or so intervals between SDM applications in the present invention disclosure.

In the published literature, the production and destruction of heat shock proteins (HSPs) in cells over longer durations is usually described by a collection of 9-13 simultaneous mass-balance differential equations that describe the behavior of the various molecular species involved in the life cycle of an HSP molecule. These simultaneous equations are usually solved by computer to show the behavior in time of the HSPs and the other species after the temperature has been suddenly raised.

These equations are all conservation equations based on the reactions of the various molecular species involved in the activity of HSPs. To describe the behavior of the HSPs in the minute or so intervals between repeated applications of SDM, we shall use the equations described in M. Rybinski, Z. Szymanska, S. Lasota, A. Gambin (2013) Modeling the efficacy of hyperthermia treatment. Journal of the Royal Society Interface 10, No. 88, 20130527 (Rybinski et al (2013)). The species considered in Rybinski et al (2013) are shown in Table 8.

TABLE 8

HSP system species in Rybinski et al (2013) description:

| | |
|---|---|
| HSP | ubiquitous heat shock protein of molecular weight 70 Da (in free, activated state) |
| HSF | heat shock (transcription) factor that has no DNA binding capability |
| $HSF_3$ | (trimer) heat shock factor capable of binding to DNA, formed from HSF |
| HSE | heat shock element, a DNA site that initiates transcription of HSP when bound to $HSF_3$ |
| mRNA | messenger RNA molecule for producing HSP |
| S | substrate for HSP binding: a damaged protein |
| P | properly folded protein |
| HSP•HSF | a complex of HSP bound to HSF (unactivated HSPs) |
| $HSF_3$•HSE | a complex of $HSF_3$ bound to HSE, that induces transcription and the creation of a new HSP mRNA molecule |
| HSP•S | a complex of HSP attached to damaged protein (HSP actively repairing the protein) |

The coupled simultaneous mass conservation equations for these 10 species are summarized below as eqs. [2]-[11]:

$$d[HSP]/dt = (l_1 + k_{10})[HSPS] + l_2[HSPHSF] + k_4[mRNA] - k_1[S][HSP] - k_2[HSP][HSF] - l_3[HSP][HSF_3] - k_9[HSP] \quad [2]$$

$$d\{HSF\}/dt = l_2[HSPHSF] + 2l_3[HSP][HSF_3] + k_6[HSPHSF][S] - k_2[HSP][HSF] - 3k_3[HSF]^3 - l_6[HSPS][HSF] \quad [3]$$

$$d[S]/dt = k_{11}\{[P] + l_1[HSPS] + l_6[SPS][HSF] - k_1[S][HSP] - k_6[HSPHSF][S] \quad [4]$$

$$d[HSPHSF]/dt = k_2[HSP][HSF] + l_6[HSPS][HSF] + l_3[HSP][HSF_3] - l_2[HSPHSF] - k_6[HSPHSF][S] \quad [5]$$

$$d[HSPS]/dt = k_1[S][HSP] + k_6[HSPHSF][S] - (l_1 + k_{10})[HSPS] - l_6[HSPS][HSF] \quad [6]$$

$$d[HSF_3]/dt = k_3[HSF]^3 + l_7[HSF_3][HSE] - l_3[HSP][HSF_3] - k_7[HSF_3][HSE] \quad [7]$$

$$d[HSE]/dt = l_7[HSF_3][HSE] - k_7[HSF_3][HSE] \quad [8]$$

$$d[HSF_3HSE]/dt = k_7[HSF_3][HSE] - l_7[HSF_3][HSE] \quad [9]$$

$$d[mRNA]/dt = k_8[HSF_3HSE] - k_5[mRNA] \quad [10]$$

$$d[P]/dt = k_{10}[HSPS] - k_{11}[P] \quad [11]$$

In these expressions, [ ] denotes the cellular concentration of the quantity inside the bracket. For Rybinski et al (2013), the initial concentrations at the equilibrium temperature of 310 K are given in Table 9.

TABLE 9

Initial values of species at 310K for a typical cell in arbitrary units [Rybinski et al (2013)]. The arbitrary units are chosen by Rybinski et al for computational convenience: to make the quantities of interest in the range of 0.01-10.

| | |
|---|---|
| [HSP(0)] | 0.308649 |
| [HSF(0)] | 0.150836 |
| [S(0)] | 0.113457 |
| [HSPHSF(0)] | 2.58799 |
| [HSPS(0)] | 1.12631 |
| [$HSF_3$(0)] | 0.0444747 |
| [HSE(0)] | 0.957419 |
| [$HSF_3$HSE(0)] | 0.0425809 |
| [mRNA(0)] | 0.114641 |
| [P(0)] | 8.76023 |

The Rybinski et al (2013) rate constants are shown in Table 10.

TABLE 10

Rybinski et al (2013) rate constants giving rates in $min^{-1}$ for the arbitrary concentration units of the previous table.

| |
|---|
| $l_1$ = 0.0175 |
| $k_1$ = 1.47 |
| $l_2$ = 0.0175 |
| $k_2$ = 1.47 |
| $l_3$ = 0.020125 |
| $k_3$ = 0.0805 |
| $k_4$ = 0.1225 |
| $k_5$ = 0.0455 |
| $k_6$ = 0.0805 |
| $l_6$ = 0.00126 |
| $l_7$ = 0.1225 |
| $l_7$ = 0.1225 |
| $k_8$ = 0.1225 |
| $k_9$ = 0.0455 |
| $k_{10}$ = 0.049 |

TABLE 10-continued

Rybinski et al (2013) rate constants giving rates in min$^{-1}$ for the arbitrary concentration units of the previous table.

$k_{11} = 0.00563271$

The initial concentration values of Table 9 and the rate constants of Table 10 were determined by Rybinski et al (2013) to correspond to experimental data on overall HSP system behavior when the temperature was increased on the order of 5° C. for several (e.g. 350) minutes.

Note that the initial concentration of HSPs is 100× 0.308649/(8.76023+0.113457+1.12631)}=3.09% of the total number of proteins present in the cell.

Although the rate constants of Table 10 are used by Rybinski et al for T=310+5+315K, it is likely that very similar rate constants exist at other temperatures. In this connection, the qualitative behavior of the simulations is similar for a large range of parameters. For convenience, we shall assume that the values of the rate constants in Table 10 are a good approximation for the values at the equilibrium temperature of T=310K.

Figure 24A:
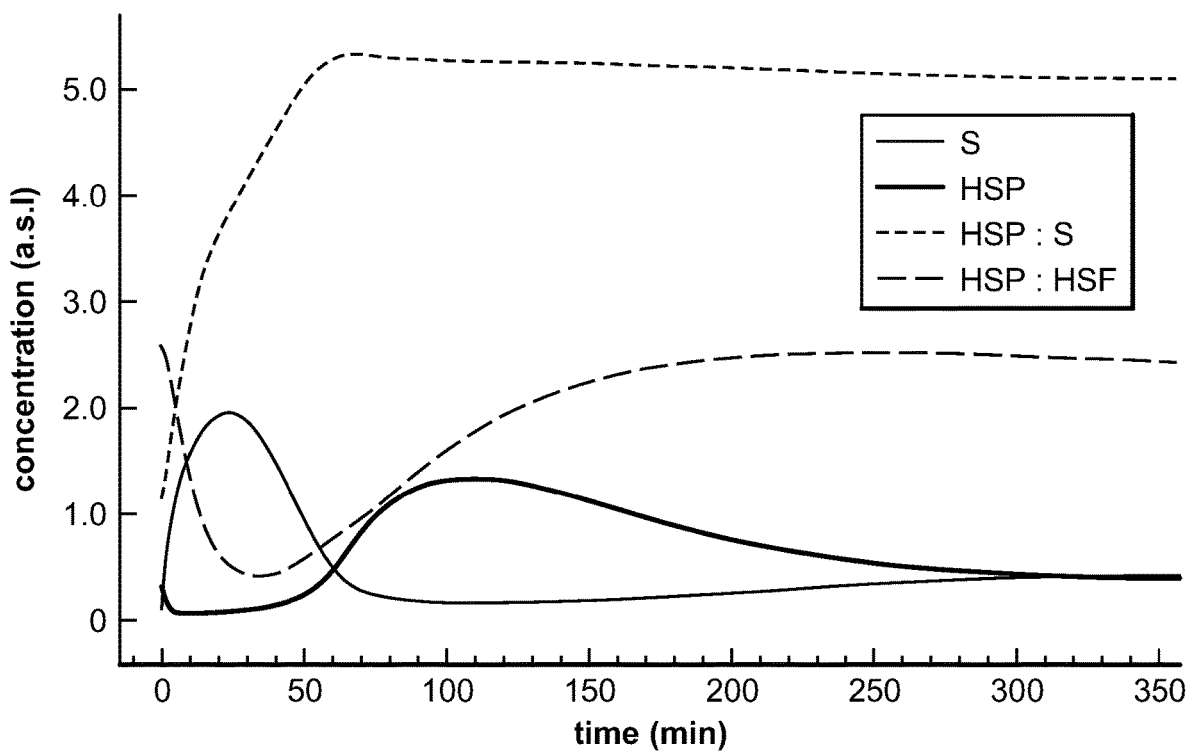
FIGS. 24A and 24B are graphs depicting the behavior of HSP cellular system components over time following a sudden increase in temperature.
Figure 24B:
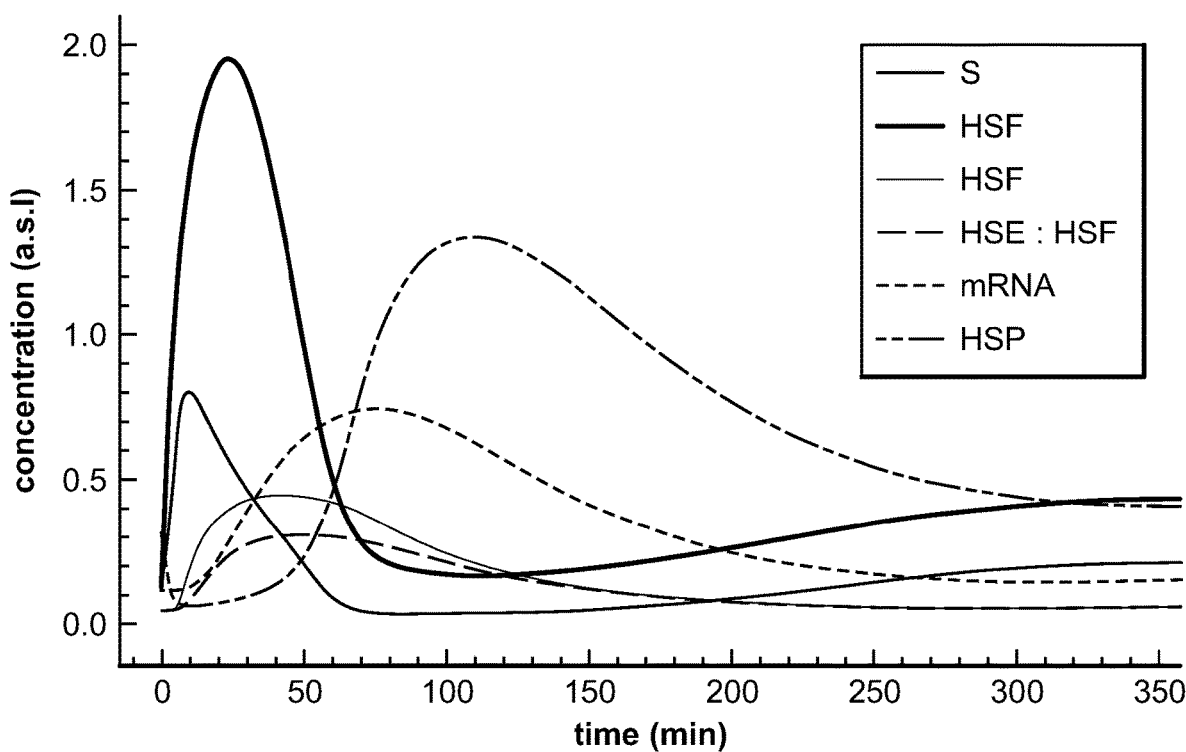
Figure 25A:
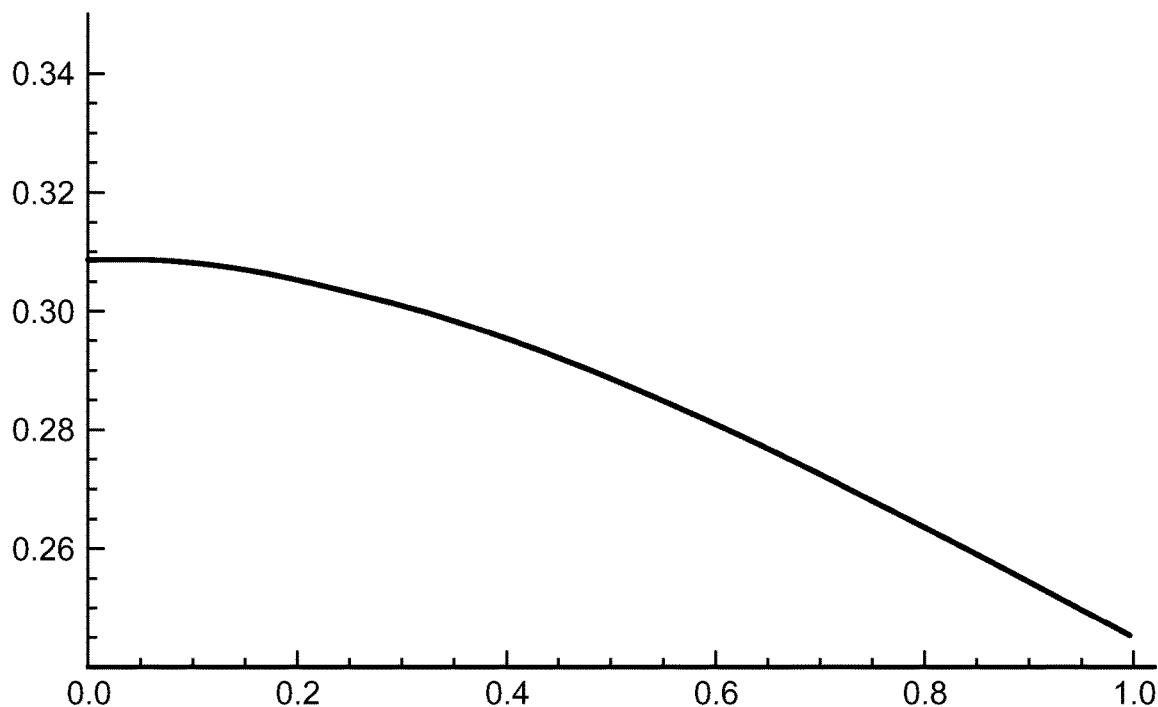
FIGS. 25A-25H are graphs depicting the behavior of HSP cellular system components in the first minute following a sudden increase in temperature.
Figure 25B:
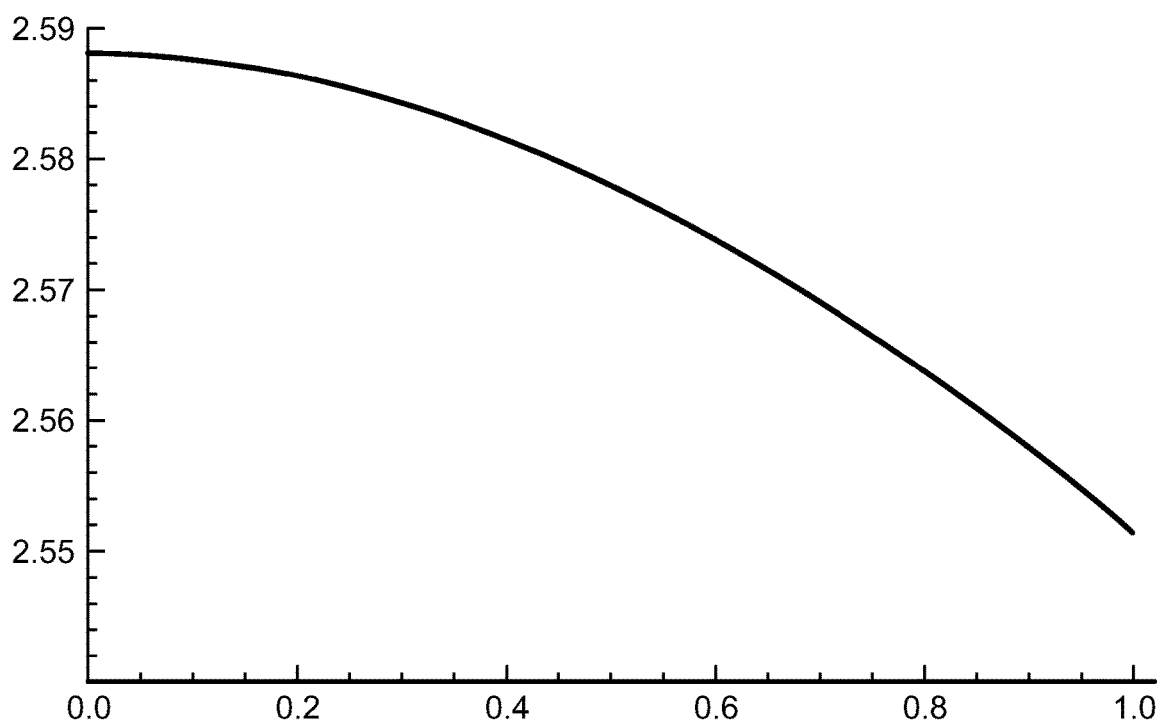
Figure 25C:
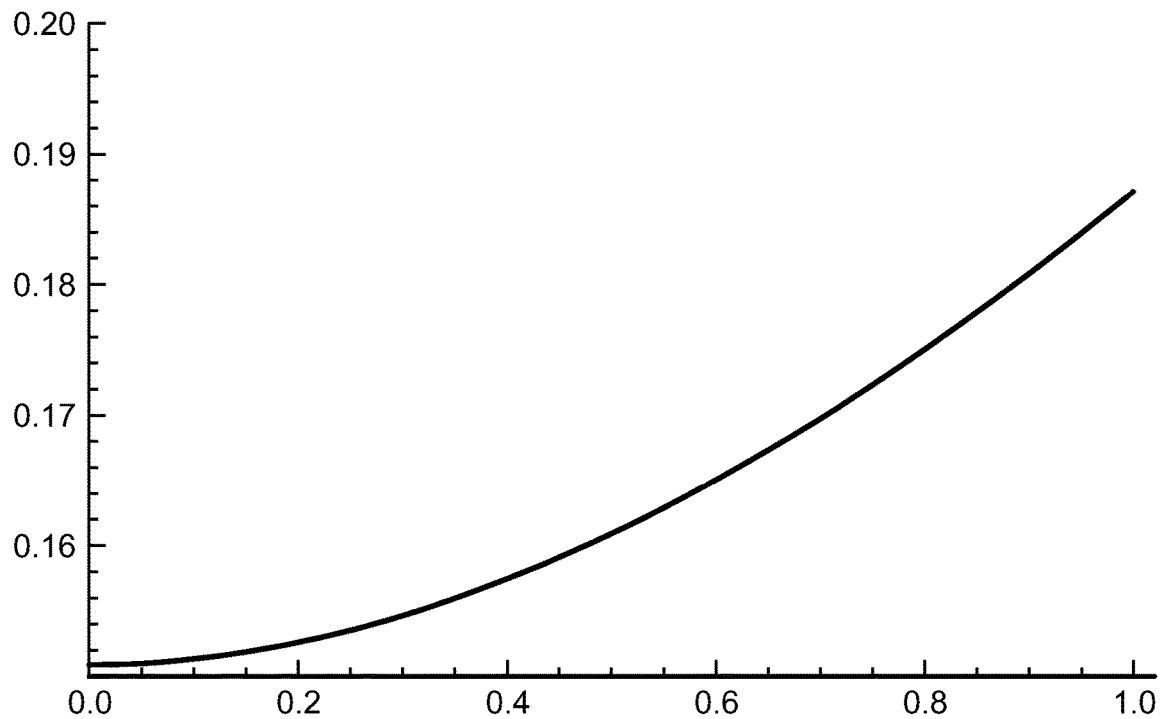
Figure 25D:
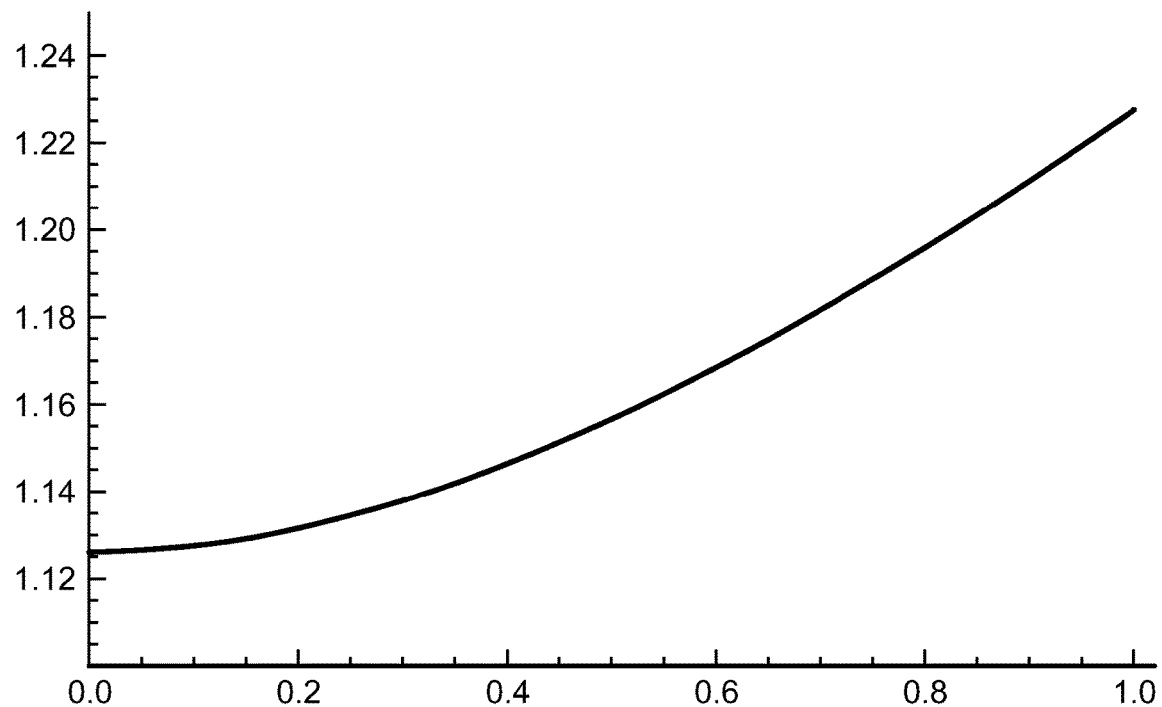
Figure 25E:
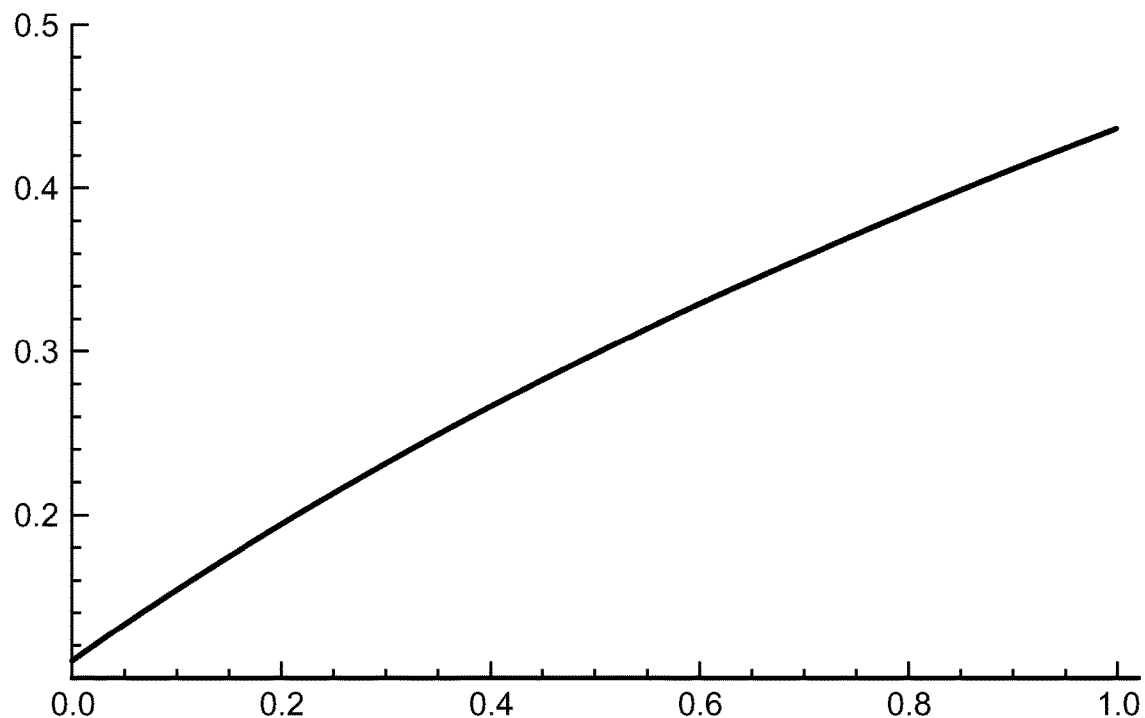
Figure 25F:
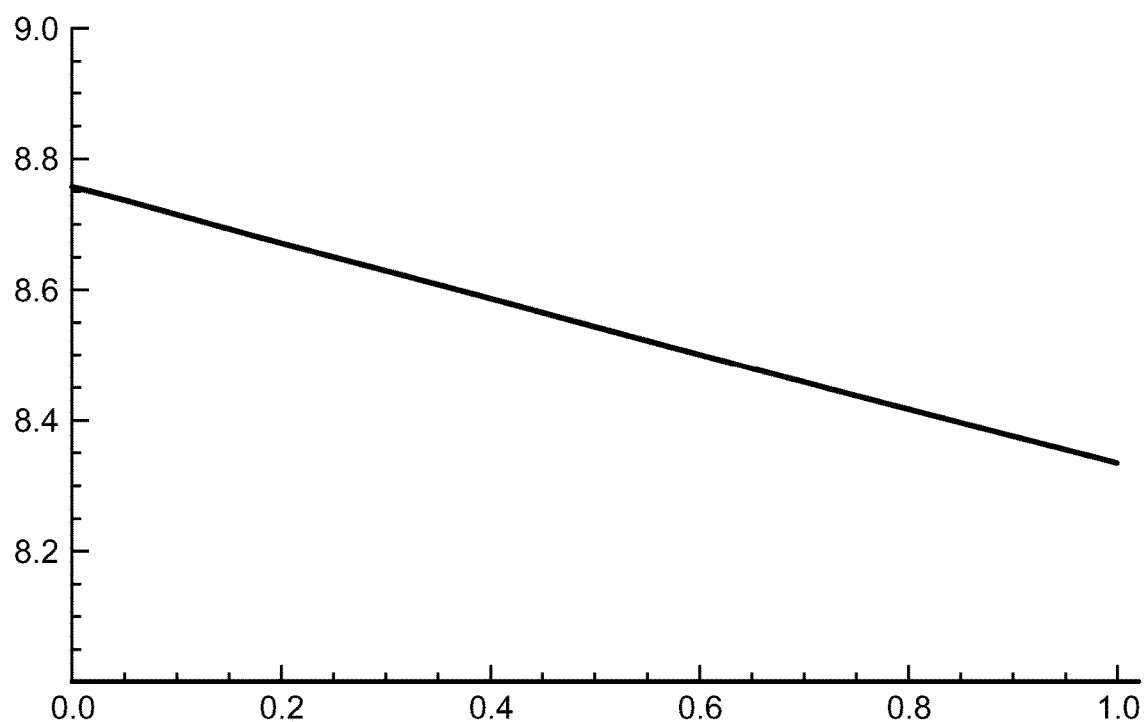
Figure 25G:
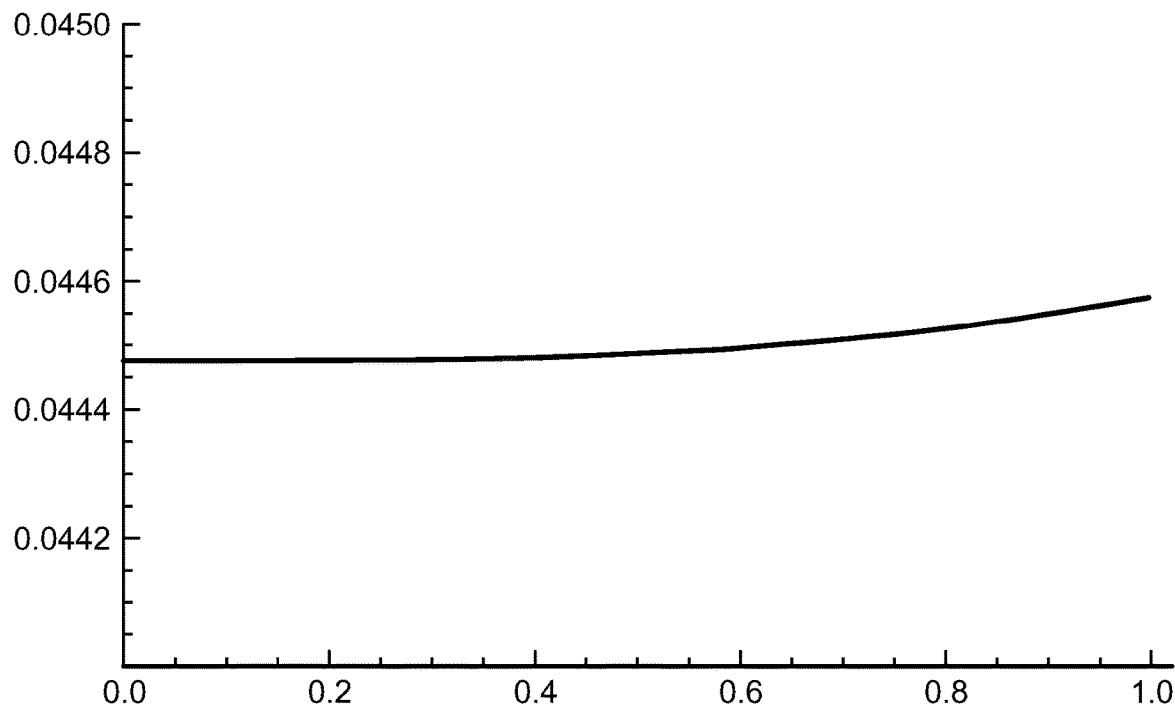
Figure 25H:
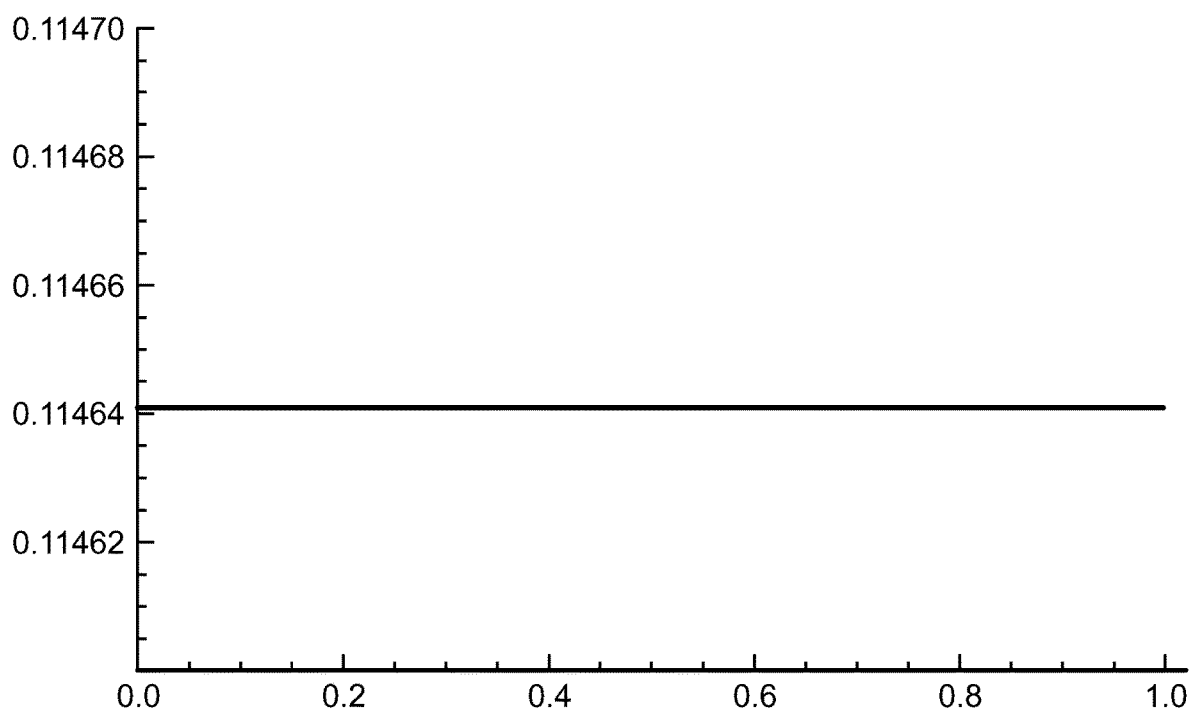

The behavior of the different components in the Rybinski et al cell is displayed in FIGS. 24A-24B for 350 minutes for the situation where the temperature is suddenly increased 5K at t=0 from an ambient 310K.

With continuing reference to FIGS. 24A-24B, the behavior of HSP cellular system components during 350 minutes following a sudden increase in temperature from 37° C. to 42° C. is shown.

Here, the concentrations of the components are presented in computationally convenient arbitrary units. S denotes denatured or damaged proteins that are as yet unaffected by HSPs; HSP denotes free (activated) heat shock proteins; HSP:S denotes activated HSPs that are attached to the damaged proteins and performing repair; HSP:HSF denotes (inactive) HSPs that are attached to heat shock factor monomers; HSF denotes a monomer of heat shock factor; $HSF_3$ denotes a trimer of heat shock factor that can penetrate the nuclear membrane to interact with a heat shock element on the DNA molecule; $HSE:HSF_3$ denotes a trimer of heat shock factor attached to a heat shock element on the DNA molecule that initiates transcription of a new mRNA molecule; mRNA denotes the messenger RNA molecule that results from the $HSE:HSF_3$, and that leads to the production of a new (activated) HSP molecule in the cell's cytoplasm.

FIG. 24 shows that initially the concentration of activated HSPs is the result of release of HSPs sequestered in the molecules HSPHSF in the cytoplasm, with the creation of new HSPs from the cell nucleus via mRNA not occurring until 60 minutes after the temperature rise occurs. FIG. 24 also shows that the activated HSPs are very rapidly attached to damaged proteins to begin their repair work. For the cell depicted, the sudden rise in temperature also results in a temporary rise in damaged protein concentration, with the peak in the damaged protein concentration occurring about 30 minutes after the temperature increase.

FIG. 24 shows what the Rybinski et al equations predict for the variation of the 10 different species over a period of 350 minutes. However, the present invention is concerned with SDM application is on the variation of the species over the much shorter O(minute) interval between two applications of SDM at any single retinal locus. It will be understood that the preferred embodiment of SDM in the form of laser light treatment is analyzed and described, but it is applicable to other sources of energy as well.

With reference now to FIGS. 25A-25H, the behavior of HSP cellular system components during the first minute following a sudden increase in temperature from 37° C. to 42° C. using the Rybinski et al. (2013) equations with the initial values and rate constants of Tables 9 and 10 are shown. The abscissa denotes time in minutes, and the ordinate shows concentration in the same arbitrary units as in FIG. 25.

FIG. 25 shows that the nuclear source of HSPs plays virtually no role during a 1 minute period, and that the main source of new HSPs in the cytoplasm arises from the release of sequestered HSPs from the reservoir of HSPHSF molecules. It also shows that a good fraction of the newly activated HSPs attach themselves to damaged proteins to begin the repair process.

The initial concentrations in Table 9 are not the equilibrium values of the species, i.e. they do not give d[ . . . ]/dt=0, as evidenced by the curves in FIGS. 24 and 25. The equilibrium values that give d[ . . . ]/dt=0 corresponding to the rate constants of Table 10 are found to be those listed in Table 11.

TABLE 11

Equilibrium values of species in arbitrary units [Rybinski et al (2013)] corresponding to the rate constants of Table 10. The arbitrary units are those chosen by Rybinski et al for computational convenience: to make the quantities of interest in the range of 0.01-10.

| | |
|---|---|
| [HSP(equil)] | 0.315343 |
| [HSF(equil)] | 0.255145 |
| [S(equil)] | 0.542375 |
| [HSPHSF(equil)] | 1.982248 |
| [HSPS(equil)] | 5.05777 |
| [$HSF_3$(equil)] | 0.210688 |
| [HSE(equil)] | 0.206488 |
| [$HSF_3HSE$(equil)] | 0.643504 |
| [mRNA(equil)] | 0.1171274 |
| [P(equil)] | 4.39986 |

Note that the equilibrium concentration of HSPs is 100× {0.315343/(4.39986+5.05777+0.542375)}=3.15% of the total number of proteins present in the cell. This Is comparable, but less than the anticipated 5%-10% total number of proteins found by other researchers. However, we have not attempted to adjust percentage upwards expecting that the general behavior will not be appreciably changed as Indicated by other researchers.

The inventors have found that a first treatment to the target tissue may be performed by repeatedly applying the pulsed energy (e.g., SDM) to the target tissue over a period of time so as to controllably raise a temperature of the target tissue to therapeutically treat the target tissue without destroying or permanently damaging the target tissue. A "treatment" comprises the total number of applications of the pulsed energy to the target tissue over a given period of time, such as dozens or even hundreds of light or other energy applications to the target tissue over a short period of time, such as a period of less than ten seconds, and more typically a period of less than one second, such as 100 milliseconds to 600 milliseconds. This "treatment" controllably raises the temperature of the target tissue to activate the heat shock proteins and related components.

What has been found, however, is that if the application of the pulsed energy to the target tissue is halted for an interval of time, such as an interval of time that exceeds the first period of time comprising the "first treatment", which may comprise several seconds to several minutes, such as three seconds to three minutes or more preferably ten seconds to ninety seconds, and then a second treatment is performed on the target tissue after the interval of time within a single treatment session or office visit, wherein the second treatment also entails repeatedly reapplying the pulsed energy to the target tissue so as to controllably raise the temperature of the target tissue to therapeutically treat the target tissue without destroying or permanently damaging the target tissue, the amount of activated HSPs and related components in the cells of the target tissue is increased resulting in a more effective overall treatment of the biological tissue. In other words, the first treatment creates a level of heat shock protein activation of the target tissue, and the second treatment increases the level of heat shock protein activation in the target tissue above the level due to the first treatment. Thus, performing multiple treatments to the target tissue of the patient within a single treatment session or office visit enhances the overall treatment of the biological tissue so long as the second or additional treatments are performed after an interval of time which does not exceed several minute but which is of sufficient length so as to allow temperature relaxation so as not to damage or destroy the target tissue.

This technique may be referred to herein as "stair-stepping" in that the levels of activated HSP production increase with the subsequent treatment or treatments within the same office visit treatment session. This "stair-stepping" technique may be described by a combination of the Arrhenius integral approach for subsecond phenomena with the Rybinski et al. (2013) treatment of intervals between repeated subsecond applications of the SDM or other pulsed energy.

For the proposed stair-stepping SDM (repetitive SDM applications) proposed in this invention disclosure, there are some important differences from the situation depicted in FIG. 24:

SDM can be applied prophylactically to a healthy cell, but oftentimes SDM will be applied to a diseased cell. In that case, the initial concentration of damaged proteins [S(0)] can be larger than given in Table 11. We shall not attempt to account for this, assuming that the qualitative behavior will not be changed.

The duration of a single SDM application is only subseconds, rather than the minutes shown in FIG. 24. The Rybinski et al rate constants are much smaller than the Arrhenius constants: the latter give Arrhenius integrals of the order of unity for subsecond durations, whereas the Rybinski et al rate constants are too small to do that. This is an example of the different effective rate constants that exist when the time scales of interest are different: The Rybinski et al rate constants apply to phenomena occurring over minutes, whereas the Arrhenius rate constants apply to subsecond phenomena.

Accordingly, to analyze what happens in the proposed stair-stepping SDM technique for improving the efficacy of SDM, we shall combine the Arrhenius integral treatment appropriate for the subsecond phenomena with the Rybinski et al (2013) treatment appropriate for the phenomena occurring over the order of a minute interval between repeated SDM applications:

SDM subsecond application described by Arrhenius integral formalism

Interval of O(minute) between SDM applications described by Rybinski et al (2013) equations Specifically, we consider two successive applications of SDM, each SDM micropulse train having a subsecond duration.

For the short subsecond time scale, we assume that the unactivated HSP's that are the source of the activated (free) HSP's are all contained in the HSPHSF molecules in the cytoplasm. Accordingly, the first SDM application is taken to reduce the cytoplasmic reservoir of unactivated HSPs in the initial HSPHSF molecule population from

[HSPHSF(equil)] to [HSPHSF(equil)]exp[$-\Omega$], and to increase the initial HSP molecular population from

[HSP(equil)] to [HSP(equil)]+[HSPHSF(equil)](1−exp[$-\Omega$])

as well as to increase the initial HSF molecular population from

[HSF(equil)] to [HSF(equil)]+[HSPHSF(equil)](1−exp[$-\Omega$])

The equilibrium concentrations of all of the other species will be assumed to remain the same after the first SDM application The Rybinski et al equations are then used to calculate what happens to [HSP] and [HSPHSF] in the interval $\lambda t$=O(minute) between the first SDM application and the second SDM application, with the initial values of HSP, HSF and HSPHSF after the first SDM application taken to be

[HSP(*SDM*1)]=[HSP(equil)]+[HSPHSF(equil)](1−exp[$-\Omega$])

[HSF(*SDM*1)]=[HSF(equil)]+[HSPHSF(equil)](1−exp[$-\Omega$])

and

[HSPHSF(*SDM*1)]=[HSPHSF(equil)]exp[$-\Omega$]

For the second application of SDM after the interval $\lambda t$, the values of [HSP], [HSF] and {HSPHSF} after the SDM will be taken to be

[HSP(*SDM*2)]=[HSP($\lambda t$)]+[HSPHSF($\lambda t$)](1−exp[$-\Omega$])

[HSF(*SDM*2)]=[HSF($\lambda t$)]+[HSPHSF($\lambda t$)](1−exp[$-\Omega$])

and

[HSPHSF(*SDM*2)]=[HSPHSF($\lambda t$)]exp[$-\Omega$]

where [HSP($\lambda t$)], [HSF($\lambda t$)], and [HSPHSF($\lambda t$)] are the values determined from the Rybinski et al (2013) equations at the time $\lambda t$.

Our present interest is in comparing [HSP(SDM2)] with [HSP(SDM1)], to see if the repeated application of SDM at an interval $\lambda t$ following the first application of SDM has resulted in more activated (free) HSP's in the cytoplasm. The ratio $\beta(\lambda t, \Omega)$=[HSP(SDM2)]/[HSP(SDM1)]={[{[HSP($\lambda t$)]+[HSPHSF($\lambda t$)](1−exp[$-\Omega$])}/{[HSP(0)]+[HSPHSF(0)](1−exp[$-\Omega$])} provides a direct measure of the improvement in the degree of HSP activation for a repeated application of SDM after an interval $\lambda t$ from the first SDM application.

The HSP and HSPHSF concentrations can vary quite a bit in the interval $\lambda t$ between SDM applications.

Figure 26A:
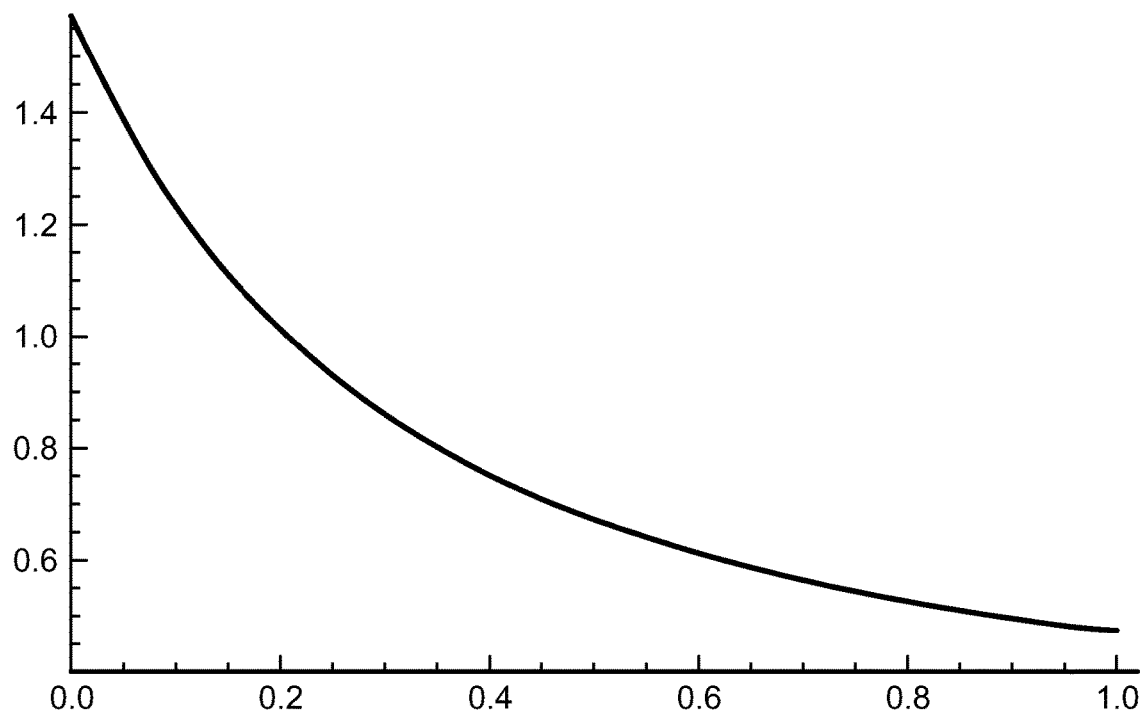
FIGS. 26A and 26B are graphs illustrating variation in the activated concentrations of HSP and inactivated HSP in the cytoplasmic reservoir over an interval of one minute, in accordance with the present invention.
Figure 26B:
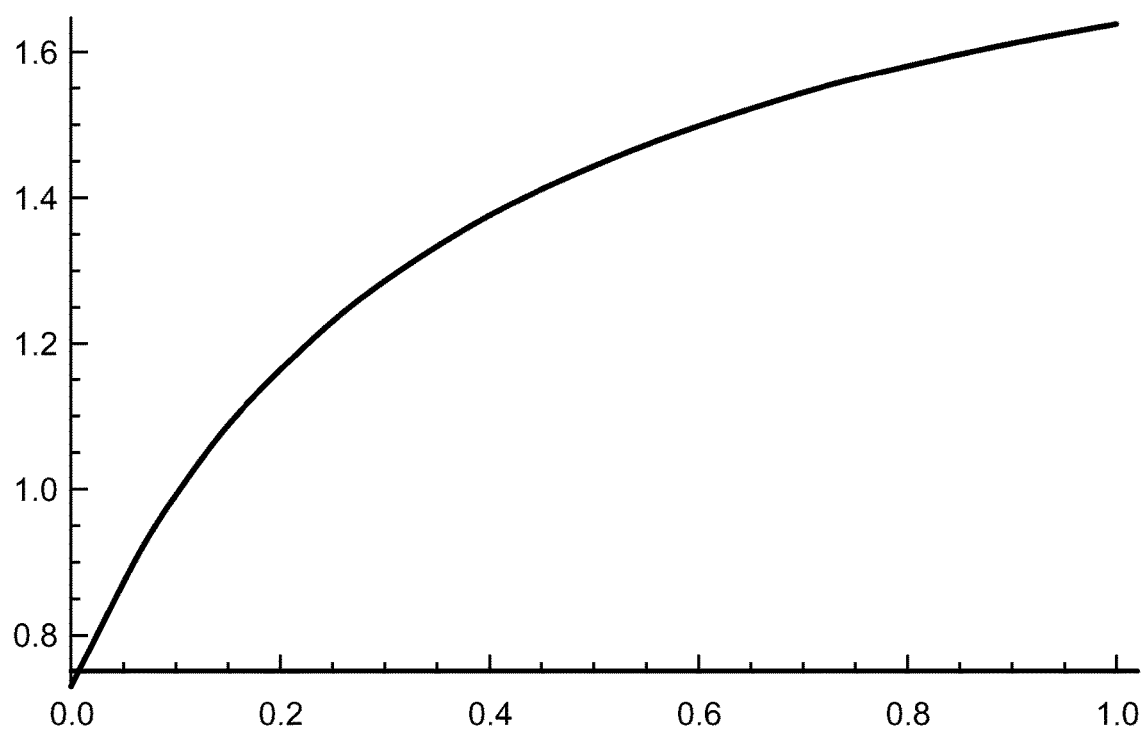

FIGS. 26A and 26B illustrate the variation in the activated concentrations [HSP] and the unactivated HSP in the cytoplasmic reservoir [HSPHSF] during an interval $\lambda t$=1 minute between SDM applications when the SDM Arrhenius integral O=1 and the equilibrium concentrations are as given in Table 11.

Although only a single repetition (one-step) is treated here, it is apparent that the procedure could be repeated to provide a multiple stair-stepping events as a means of improving the efficacy of SDM, or other therapeutic method involving activation of tissue HSPs.

Effects of varying the magnitude of the Arrhenius integral $\Omega$ and interval $\lambda t$ between two distinct treatments separated by an interval of time are shown by the following examples and results.

Nine examples generated with the procedure described above are presented in the following. All of the examples are of a treatment consisting of two SDM treatments, with the second occurring at a time $\lambda t$ following the first, and they explore:

The effect of different magnitude Arrhenius integrals $\Omega$ in the SDM treatments [Three different $\Omega$'s are considered: $\Omega$=0.2, 0.5 and 1.0]

The impact of varying the interval $\lambda t$ between the two SDM treatments [Three different $\lambda t$'s are considered: $\lambda t$=15 sec., 30 sec., and 60 sec.

As indicated above, the activation Arrhenius integral $\Omega$ depends on both the treatment parameters (e.g., laser power, duty cycle, total train duration) and on the RPE properties (e.g., absorption coefficients, density of HSPs).

Table 12 below shows the effect of different $\Omega$ ($\Omega$=0.2, 0.5, 1) on the HSP content of a cell when the interval between the two SDM treatments is $\lambda t$=1 minute. Here the cell is taken to have the Rybinski et al (2013) equilibrium concentrations for the ten species involved, given in Table 11.

Table 12 shows four HSP concentrations (in the Rybinski et al arbitrary units) each corresponding to four different times:

Before the first SDM treatment: [HSP(equil)]

Immediately after the first SDM application: [HSP(SDM1)]

At the end of the interval $\lambda t$ following the first SDM treatment: [HSP($\lambda t$)]

Immediately after the second SDM treatment at $\lambda t$: [HSP(SDM2)]

Also shown is the improvement factor over a single treatment: $\beta$=[HSP(SDM2)]/[HSP(SDM1)]

TABLE 12

HSP concentrations at the four times just described in the text:
Effect of varying the SDM $\Omega$ for two SDM applications on a
cell when the treatments are separated by
$\lambda t$ = 0.25 minutes = 15 seconds.

|  | [HSP (equil)] | [HSP (SDM1)] | [HSP ($\lambda t$)] | [HSP (SDM2)] | $\beta$ |
|---|---|---|---|---|---|
| $\Omega$ = 0.2 | 0.315 | 0.67 | 0.54 | 0.95 | 1.27 |
| $\Omega$ = 0.5 | 0.315 | 1.10 | 0.77 | 1.34 | 1.22 |
| $\Omega$ = 1.0 | 0.315 | 1.57 | 0.93 | 1.71 | 1.09 |

Table 13 is the same as Table 12, except that it is for an interval between SDM treatments of $\lambda t$=0.5 minutes=30 seconds.

TABLE 13

HSP concentrations at the four times described in the text:
Effect of varying the SDM $\Omega$ for two SDM treatments on a
cell when the treatments are separated by
$\lambda t$ = 0.5 minutes = 30 seconds.

|  | [HSP (equil)] | [HSP (SDM1)] | [HSP ($\lambda t$)] | [HSP (SDM2)] | $\beta$ |
|---|---|---|---|---|---|
| $\Omega$ = 0.2 | 0.315 | 0.67 | 0.44 | 0.77 | 1.14 |
| $\Omega$ = 0.5 | 0.315 | 1.10 | 0.58 | 1.18 | 1.08 |
| $\Omega$ = 1.0 | 0.315 | 1.57 | 0.67 | 1.59 | 1.01 |

Table 14 is the same as the Tables 12 and 13, except that the treatments are separated by one minute, or sixty seconds.

TABLE 14

HSP concentrations at the four times just described in the text:
Effect of varying the SDM $\Omega$ for two SDM treatments on a
normal (healthy) cell when the treatments are separated by
$\lambda t$ = 1 minute = 60 seconds.

|  | [HSP (equil)] | [HSP (SDM1)] | [HSP ($\lambda t$)] | [HSP (SDM2)] | $\beta$ |
|---|---|---|---|---|---|
| $\Omega$ = 0.2 | 0.315 | 0.67 | 0.30 | 0.64 | 0.95 |
| $\Omega$ = 0.5 | 0.315 | 1.10 | 0.37 | 1.06 | 0.96 |
| $\Omega$ = 1.0 | 0.315 | 1.57 | 0.48 | 1.51 | 0.96 |

Tables 12-14 show that:

The first treatment of SDM increases [HSP] by a large factor for all three $\Omega$'s, although the increase is larger the larger $\Omega$. Although not displayed explicitly in the tables, the increase in [HSP] comes at the expense of the cytoplasmic reservoir of sequestered (unactivated) HSP's: [HSPHSF(SDM1)] is much smaller than [HSPHSF(equil)]

[HSP] decreases appreciably in the interval $\lambda t$ between the two SDM treatments, with the decrease being larger the larger $\lambda t$ is. (The decrease in [HSP] is accompanied by an increase in both [HSPHSF]—as shown in FIG. 26 and in [HSPS] during the interval $\lambda t$—indicating a rapid replenishment of the cytoplasmic reservoir of unactivated HSP's and a rapid attachment of HSP's to the damaged proteins.)

For $\lambda t$ less than 60 seconds, there is an improvement in the number of activated (free) HSP's in the cytoplasm for two SDM treatments rather than a single treatment. The improvement increases as $\lambda t$ becomes smaller.

For $\lambda t$ becoming as large as 60 seconds, however, the ratio $\beta$=[HSP(SDM2)]/[HSP(SDM1)] becomes less than unity, indicating no improvement in two SDM treatments compared to a single SDM treatment although this result can vary depending on energy source parameters and tissue type that is treated.

The improvement for $\lambda t$<60 seconds is larger the smaller the SDM Arrhenius integral $\Omega$ is.

Figure 27:
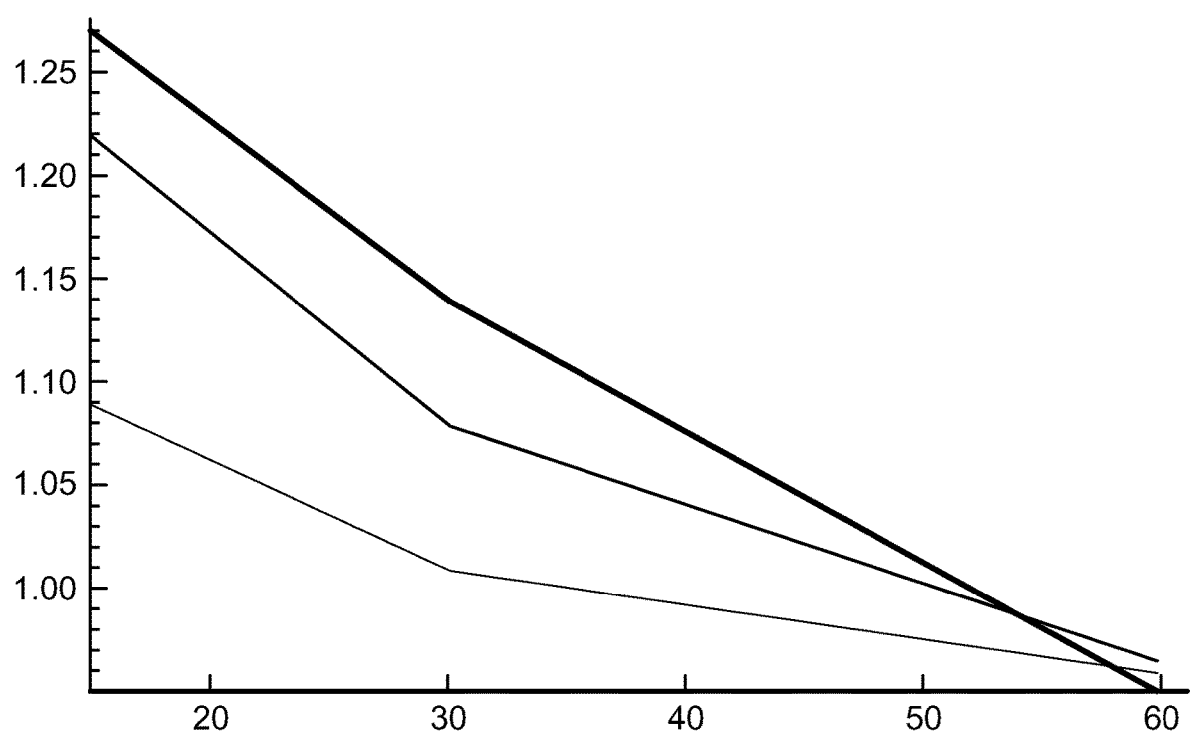
FIG. 27 is a graph depicting the improvement ratios versus interval between treatments, in accordance with the present invention.

The results for the improvement ratio $\beta$=[HSP(SDM2)]/[HSP(SDM1)] are summarized in FIG. 27, where the improvement ratio $\beta$=[HSP(SDM2)]/[HSP(SDM1)] vs. interval between SDM treatments $\lambda t$ (in seconds) for three values of the SDM Arrhenius integral Q, and for the three values of the interval $\lambda t$=15 sec, 30 sec, and 60 sec. The uppermost curve is for $\Omega$=0.2; the middle curve is for $\Omega$=0.5; and the bottom curve is for $\Omega$=1.0. These results are for the Rybinski et al (2013) rate constants of Table 10 and the equilibrium species concentrations of Table 11.

It should be appreciated that results of Tables 12-14 and FIG. 27 are for the Rybinski et al. (2013) rate constants of Table 10 and the equilibrium concentrations of Table 11. The actual concentrations and rate constants in a cell may differ from these values, and thus the number results in Tables 12-14 and FIG. 27 should be taken as representative rather than absolute. However, they are not anticipated to be significantly different. Thus, performing multiple intra-sessional treatments on a single target tissue location or area, such as a single retinal locus, with the second and subsequent treatments following the first after an interval anywhere from three seconds to three minutes, and preferably ten seconds to ninety seconds, should increase the activation of HSPs and related components and thus the efficacy of the overall treatment of the target tissue. The resulting "stair-stepping" effect achieves incremental increases in the number of heat shock proteins that are activated, enhancing the therapeutic effect of the treatment. However, if the interval of time between the first and subsequent treatments is too great, then the "stair-stepping" effect is lessened or not achieved.

The technique of the present invention is especially useful when the treatment parameters or tissue characteristics are such that the associated Arrhenius integral for activation is low, and when the interval between repeated applications is small, such as less than ninety seconds, and preferably less than a minute. Accordingly, such multiple treatments must be performed within the same treatment session, such as in a single office visit, where distinct treatments can have a window of interval of time between them so as to achieve the benefits of the technique of the present invention.

Although several embodiments have been described in detail for purposes of illustration, various modifications may be made without departing from the scope and spirit of the invention. Accordingly, the invention is not to be limited, except as by the appended claims.

What is claimed is:

1. A process for heat treating retinal tissue, comprising the steps of:
selecting a treatment radiation spot size having a diameter within a range of between 10-700 microns;
selecting a total pulsed treatment radiation train duration within a range of between 30-800 milliseconds;
generating pulsed treatment radiation comprising a plurality of light beams having a wavelength between 570nm and 1300nm and an average power selected within a range of between 1.0 to 37.5 watts;
simultaneously applying the plurality of treatment light beams to retinal tissue for a first period of time comprising 30-800 milliseconds such that a plurality of spaced apart treatment radiation spots are formed on the retinal tissue and the retinal tissue is heat stimulated sufficiently to create a therapeutic effect without permanently damaging or destroying the tissue and to stimulate heat shock protein activation in the tissue;
halting the application of the treatment radiation for an interval of time comprising between 10 to 90 seconds; and
re-applying the treatment radiation to the tissue after the interval of time within a single treatment session so as to controllably raise the temperature of the tissue without destroying the tissue to increase the level of heat shock protein activation in the tissue
wherein the average power of the treatment radiation is selected to be monotonically lower within its range when the treatment radiation spot size is selected to be smaller within its range and/or when the total pulsed treatment radiation train duration is selected to be higher within its range.

2. The process of claim 1, wherein the tissue is heated to between six and eleven degrees Celsius during the application of the treatment radiation to the tissue, but the average temperature rise of the tissue over six minutes or less is maintained at approximately one degree Celsius or less.

3. The process of claim 2, wherein the treatment radiation spot size, total pulsed treatment radiation train duration and average power are selected based on thermal properties of the retinal tissue being treated.

4. The process of claim 1, wherein the treatment radiation is applied to at least a portion of the fovea of the eye.

5. The process of claim 1, wherein the treatment radiation has a wavelength between 600nm-1100nm, an average power of between 1.0 and 6.94 watts, and forms at least one treatment spot having a diameter between 100-500 microns.

6. The process of claim 1, wherein during an interval of time, comprising less than one second, between pulses of treatment radiation applied to a first treatment area of the tissue, simultaneously applying the treatment radiation beams to a second treatment area of the tissue sufficiently spaced apart from the first treatment area of the tissue to avoid thermal tissue damage of the target tissue and repeatedly simultaneously applying, in an alternating manner during the same treatment session, the treatment radiation beams to each of the first and second treatment areas of the tissue until a predetermined number of applications to each of the first and second treatment areas of the tissue has been achieved.

7. The process of claim 1, wherein the light beams have a duty cycle between 2.5% and 5%.

8. A process for heat treating retinal tissue, comprising the steps of:
generating a pulsed treatment radiation comprising a plurality of light beams having a wavelength between 570nm and 1300nm and an average power selected from a range of between 1.0 to 37.5 watts;
simultaneously applying the treatment radiation light beams to retinal tissue, including at least a portion of the fovea, such that a plurality of spaced apart treatment spots each having a diameter selected from a range of between 100-700 microns is formed on the retinal tissue and for a total pulsed train duration selected from a range of between 30-800 milliseconds such that the retinal tissue is heated to between six and eleven degrees Celsius during the application of the treatment radiation to the retinal tissue while providing thermal relaxation periods between pulses such that the average temperature rise of the tissue over six minutes or less is maintained at approximately one degree Celsius or less, whereby a therapeutic effect is created without permanently damaging or destroying the tissue;
applying the treatment radiation to the tissue for a first period of time comprising the total pulsed train duration of between 30-800 milliseconds to stimulate heat shock protein activation in the tissue;
halting the application of the treatment radiation for an interval of time that exceeds the first period of time comprising 10 to 90 seconds; and
re-applying the treatment radiation to the tissue after the interval of time within a single treatment session so as to controllably raise the temperature of the tissue without destroying the tissue to increase the level of heat shock protein activation in the tissue.

9. The process of claim 8, wherein the treatment radiation has a wavelength between 600nm-1100nm, an average power of between 1.0 and 6.94 watts, and forms treatment spots having a diameter between 100-500 microns.

10. The process of claim 8, wherein during an interval of time, comprising less than one second, between pulses of treatment radiation applied to a first treatment area of the tissue, simultaneously applying the treatment radiation beams to a second treatment area of the tissue sufficiently spaced apart from the first treatment area of the tissue to avoid thermal tissue damage of the target tissue and repeatedly simultaneously applying, in an alternating manner during the same treatment session, the treatment radiation beams to each of the first and second treatment areas of the tissue until a predetermined number of applications to each of the first and second treatment areas of the tissue has been achieved.

11. The process of claim 8, wherein the average power of the treatment radiation is selected to be monotonically lower within its range when the treatment radiation spot size is selected to be smaller within its range and/or when the total pulsed treatment radiation duration is selected to be higher within its range.

12. The process of claim 8, wherein the treatment radiation spot size, total pulsed treatment radiation train duration and average power are selected based on thermal properties of the retinal tissue being treated.

13. The process of claim 8, wherein the light beams have a duty cycle between 2.5% and 5%.

14. A process for heat treating retinal tissue, comprising the steps of:
   generating a plurality of spaced apart pulsed treatment radiation beams having a wavelength between 600nm and 1100nm and an average power selected from a range of between 1.0 to 6.94 watts and a duty cycle between 2.5% and 5%;
   applying the treatment radiation beams to retinal tissue such that a plurality of treatment spots each having a diameter selected from a range of between 100-500 microns are formed in a treatment area of the retinal tissue for a duration selected from a range of between 30-800 milliseconds such that the retinal tissue is heated to between six and eleven degrees Celsius during the application of the treatment radiation beams to the retinal tissue while providing thermal relaxation periods between pulses such that the average temperature rise of the tissue over six minutes or less is maintained at approximately one degree Celsius or less, whereby a therapeutic effect is created without permanently damaging or destroying the tissue;
   applying the treatment radiation beams to the tissue for a first period of time comprising the selected total pulsed train duration of 30-800 milliseconds to stimulate heat shock protein activation in the tissue;
   halting the application of the treatment radiation beams for an interval of time that exceeds the first period of time comprising 10 to 90 seconds; and
   re-applying the treatment radiation beams to the tissue after the interval of time within a single treatment session so as to controllably raise the temperature of the tissue without destroying the tissue to increase the level of heat shock protein activation in the tissue;
   wherein the average power of the treatment radiation is selected to be monotonically lower within its range when the treatment radiation spot size is selected to be smaller within its range and/or when the total pulsed treatment radiation duration is selected to be higher within its range.

15. The process of claim 14, wherein the treatment radiation beams are applied to at least a portion of the fovea of the eye.

16. The process of claim 14, wherein during an interval of time, comprising less than one second, between pulses of the treatment radiation beams applied to the first treatment area of the tissue, including the steps of:
   simultaneously applying the treatment radiation beams to a second treatment area of the tissue sufficiently spaced apart from the first treatment area of the tissue to avoid thermal tissue damage of the target tissue and repeatedly simultaneously applying, in an alternating manner during the same treatment session, the treatment radiation beams to each of the first and second treatment areas of the tissue until a predetermined number of applications to each of the first and second treatment areas of the tissue has been achieved.

17. The process of claim 14, wherein the treatment radiation spot size, total pulsed treatment radiation train duration and average power are selected based on thermal properties of the retinal tissue being treated.

* * * * *